United States Patent
Youngbull et al.

(10) Patent No.: US 12,350,672 B2
(45) Date of Patent: Jul. 8, 2025

(54) SYSTEMS AND METHODS RELATED TO CONTINUOUS FLOW DROPLET REACTION

(71) Applicant: ARIZONA BOARD OF REGENTS ON BEHALF OF ARIZONA STATE UNIVERSITY, Scottsdale, AZ (US)

(72) Inventors: Cody Youngbull, Tempe, AZ (US); Andrew Hatch, Tempe, AZ (US); Andrew Larsen, Scottsdale, AZ (US); Tathagata Ray, Tempe, AZ (US); Matthew Underhill, Gilbert, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 18/597,605

(22) Filed: Mar. 6, 2024

(65) Prior Publication Data

US 2024/0342721 A1 Oct. 17, 2024

Related U.S. Application Data

(60) Continuation of application No. 18/111,342, filed on Feb. 17, 2023, now abandoned, which is a (Continued)

(51) Int. Cl.
*B01L 3/00* (2006.01)
*B01F 33/302* (2022.01)
(Continued)

(52) U.S. Cl.
CPC ........... *B01L 3/502784* (2013.01); *B01L 7/52* (2013.01); *B01L 7/525* (2013.01); *C12Q 1/6848* (2013.01);
(Continued)

(58) Field of Classification Search
CPC ...... B01L 3/502784; B01L 7/52; B01L 7/525; B01L 2200/0673; B01L 2200/16;
(Continued)

(56) References Cited

U.S. PATENT DOCUMENTS

| | | | |
|---|---|---|---|
| 6,143,496 | A | 11/2000 | Brown et al. |
| 6,767,706 | B2 | 7/2004 | Quake et al. |
| 6,960,437 | B2 | 11/2005 | Enzelberger et al. |
| 6,977,145 | B2 | 12/2005 | Fouillet et al. |
| 7,129,091 | B2 | 10/2006 | Ismagilov et al. |

(Continued)

FOREIGN PATENT DOCUMENTS

| | | |
|---|---|---|
| CN | 104114282 A | 10/2014 |
| EP | 1574586 B1 | 11/2012 |

(Continued)

OTHER PUBLICATIONS

Chabert et al.: Droplet fusion by alternating current (AC) field electrocoalescence in microchannels. Electrophoresis 26(19):3706-3715 (2005).

(Continued)

*Primary Examiner* — Jennifer Wecker
*Assistant Examiner* — Oyeleye Alexander Alabi
(74) *Attorney, Agent, or Firm* — WILSON SONSINI GOODRICH & ROSATI

(57) ABSTRACT

Described herein are systems relating to a continuous-flow instrument that includes all necessary components for digital droplet quantification without the need to introduce key reagents or collect and transfer droplets between stages of instrument operation. Digital quantification can proceed without any additional fluid or consumable handling and without exposing fluids to risk of external contamination.

20 Claims, 39 Drawing Sheets

Related U.S. Application Data continuation of application No. 17/827,614, filed on May 27, 2022, now Pat. No. 11,607,689, which is a division of application No. 16/413,416, filed on May 15, 2019, now Pat. No. 11,413,616, which is a continuation of application No. PCT/US2017/063293, filed on Nov. 27, 2017.

(60) Provisional application No. 62/439,814, filed on Dec. 28, 2016, provisional application No. 62/427,086, filed on Nov. 28, 2016.

(51) Int. Cl.
- B01F 33/3033 (2022.01)
- B01L 7/00 (2006.01)
- C12Q 1/6848 (2018.01)
- C12Q 1/686 (2018.01)

(52) U.S. Cl.
CPC ....... B01F 33/3021 (2022.01); B01F 33/3033 (2022.01); B01L 2200/0673 (2013.01); B01L 2200/16 (2013.01); B01L 2300/0867 (2013.01); B01L 2300/16 (2013.01); B01L 2300/161 (2013.01); B01L 2300/18 (2013.01); B01L 2400/0415 (2013.01); C12Q 1/686 (2013.01)

(58) Field of Classification Search
CPC ......... B01L 2300/0867; B01L 2300/16; B01L 2300/161; B01L 2300/18; B01L 2400/0415; C12Q 1/6848; C12Q 1/686; B01F 33/3021; B01F 33/3033
See application file for complete search history.

(56) References Cited

U.S. PATENT DOCUMENTS

| | | |
|---|---|---|
| 7,268,167 B2 | 9/2007 | Higuchi et al. |
| 7,294,503 B2 | 11/2007 | Quake et al. |
| 7,622,081 B2 | 11/2009 | Chou et al. |
| 7,772,287 B2 | 8/2010 | Higuchi et al. |
| RE41,780 E | 9/2010 | Anderson et al. |
| RE43,365 E | 5/2012 | Anderson et al. |
| 8,278,071 B2 | 10/2012 | Brown et al. |
| 8,304,193 B2 | 11/2012 | Ismagilov et al. |
| 8,329,407 B2 | 12/2012 | Ismagilov et al. |
| 8,399,198 B2 | 3/2013 | Hiddessen et al. |
| 8,591,419 B2 | 11/2013 | Tyler |
| 8,633,015 B2 | 1/2014 | Ness et al. |
| 8,709,762 B2 | 4/2014 | Hindson |
| 8,730,479 B2 | 5/2014 | Ness et al. |
| 8,771,747 B2 | 7/2014 | O'Hagan et al. |
| 8,822,148 B2 | 9/2014 | Ismagliov et al. |
| 8,841,093 B2 | 9/2014 | Takahashi et al. |
| 8,858,440 B2 | 10/2014 | Tyler |
| 8,871,444 B2 | 10/2014 | Griffiths et al. |
| 8,889,083 B2 | 11/2014 | Ismagilov et al. |
| 8,951,732 B2 | 2/2015 | Pollack et al. |
| 8,969,255 B2 | 3/2015 | Johnston et al. |
| 9,012,390 B2 | 4/2015 | Holtze et al. |
| 9,029,083 B2 | 5/2015 | Griffiths et al. |
| 9,056,289 B2 | 6/2015 | Weitz et al. |
| 9,074,242 B2 | 7/2015 | Larson et al. |
| 9,127,310 B2 | 9/2015 | Larson et al. |
| 9,132,394 B2 | 9/2015 | Makarewicz, Jr. et al. |
| 9,156,010 B2 | 10/2015 | Colston et al. |
| 9,181,375 B2 | 11/2015 | Tian et al. |
| 9,216,392 B2 | 12/2015 | Hindson et al. |
| 9,222,115 B2 | 12/2015 | Marble et al. |
| 9,243,288 B2 | 1/2016 | Ness et al. |
| 9,248,417 B2 | 2/2016 | Hindson et al. |
| 9,273,308 B2 | 3/2016 | Link et al. |
| 9,366,632 B2 | 6/2016 | Link et al. |
| 9,403,038 B2 | 8/2016 | Tyler et al. |
| 9,441,266 B2 | 9/2016 | Larson et al. |
| 9,492,797 B2 | 11/2016 | Makarewicz et al. |
| 9,498,761 B2 | 11/2016 | Holtze et al. |
| RE46,322 E | 2/2017 | Anderson et al. |
| 9,562,837 B2 | 2/2017 | Link |
| 9,597,026 B2 | 3/2017 | Meldrum et al. |
| 9,709,558 B2 | 7/2017 | Johnston et al. |
| 9,752,141 B2 | 9/2017 | Link et al. |
| 9,968,933 B2 | 5/2018 | Ismagilov et al. |
| 9,970,932 B2 | 5/2018 | Woodbury et al. |
| 10,006,919 B2 | 6/2018 | Woodbury et al. |
| 10,046,293 B2 | 8/2018 | Woodbury et al. |
| 10,422,793 B2 | 9/2019 | Johnston et al. |
| 10,427,125 B2 | 10/2019 | Woodbury et al. |
| 10,578,623 B2 | 3/2020 | Woodbury |
| 10,900,975 B2 | 1/2021 | Johnston |
| 11,123,740 B2 | 9/2021 | Youngbull et al. |
| 11,413,616 B2 | 8/2022 | Youngbull et al. |
| 11,607,689 B2 | 3/2023 | Youngbull et al. |
| 11,618,030 B2 | 4/2023 | Youngbull et al. |
| 2005/0227264 A1 | 10/2005 | Nobile et al. |
| 2006/0257893 A1 | 11/2006 | Takahashi et al. |
| 2008/0014589 A1 | 1/2008 | Link et al. |
| 2011/0052446 A1 | 3/2011 | Hirano et al. |
| 2011/0086780 A1 | 4/2011 | Colston, Jr. et al. |
| 2011/0165037 A1 | 7/2011 | Ismagilov et al. |
| 2012/0115738 A1 | 5/2012 | Zhou et al. |
| 2012/0194805 A1 | 8/2012 | Ness et al. |
| 2012/0231533 A1 | 9/2012 | Holl et al. |
| 2012/0301913 A1 | 11/2012 | Youngbull et al. |
| 2012/0302448 A1* | 11/2012 | Hutchison .............. C12Q 1/686 506/9 |
| 2014/0045712 A1 | 2/2014 | Link et al. |
| 2014/0193800 A1 | 7/2014 | Aguanno et al. |
| 2014/0199730 A1 | 7/2014 | Agresti et al. |
| 2014/0199731 A1 | 7/2014 | Agresti et al. |
| 2014/0202546 A1 | 7/2014 | Ismagilov et al. |
| 2014/0208832 A1 | 7/2014 | Hansen et al. |
| 2015/0018236 A1 | 1/2015 | Green et al. |
| 2016/0177375 A1 | 6/2016 | Abate et al. |
| 2017/0144116 A1 | 5/2017 | Ness et al. |
| 2021/0262020 A1 | 8/2021 | Link |
| 2023/0086845 A1 | 3/2023 | Larson et al. |
| 2023/0201835 A1 | 6/2023 | Youngbull et al. |
| 2023/0211347 A1 | 7/2023 | Youngbull et al. |

FOREIGN PATENT DOCUMENTS

| | | |
|---|---|---|
| EP | 1735458 B1 | 7/2013 |
| WO | WO-2010009141 A1 | 1/2010 |
| WO | WO-2010022391 A2 | 2/2010 |
| WO | WO-2010036352 A1 | 4/2010 |
| WO | WO-2010062654 A2 | 6/2010 |
| WO | WO-2010148365 A2 | 12/2010 |
| WO | WO-2010148365 A3 | 5/2011 |
| WO | WO-2011057028 A1 | 5/2011 |
| WO | WO-2012061442 A1 | 5/2012 |
| WO | WO-2012112440 A2 | 8/2012 |
| WO | WO-2012154594 A1 | 11/2012 |
| WO | WO-2013165748 A1 | 11/2013 |
| WO | WO-2014008381 A2 | 1/2014 |
| WO | WO-2014039718 A1 | 3/2014 |
| WO | WO-2014062981 A1 | 4/2014 |
| WO | WO-2014144383 A1 | 9/2014 |
| WO | WO-2014145123 A2 | 9/2014 |
| WO | WO-2014210207 A1 | 12/2014 |
| WO | WO-2014036312 A3 | 5/2015 |
| WO | WO-2017004250 A1 | 1/2017 |
| WO | WO-2018098438 A1 | 5/2018 |
| WO | WO-2020198690 A1 | 10/2020 |
| WO | WO-2023173043 A1 | 9/2023 |

OTHER PUBLICATIONS

Eow, et al. Electrostatic Enhancement of Coalescence of Water Droplets in Oil: a Review of the Current Understanding. Chemical engineering Journal 84 (3):173-192 (Dec. 15, 2001).

(56) References Cited

OTHER PUBLICATIONS

Han et al.: An active microfluidic system packaging technology. Sensors and Actuators B Chemical 122(1):337-346 doi:10.1016/j.snb.2006.06.028 (2007).
Hatch, Andrew et al. Continuous flow real-time PCR device using multi-channel fluorescence excitation and detection. Lab on a Chip, 14(3):562-568 (Nov. 19, 2013).
International Application No. PCT/US2016/040172 International Search Report and Written Opinion Mailed Oct. 20, 2016.
International Application No. PCT/US2017/063293 International Search Report and Written Opinion Mailed Jan. 18, 2018.
Mazutis, et al. Single-Cell Analysis and Sorting Using Droplet-Based Microfluidics. Nat Protoc. 8(5): 870-891 (May 2013).
Moscovici et al.: Electrical power free, low dead vol. pressure-driven pumping for microfluidic applications. Biomicrofluidics. Oct. 13, 2010;4(4):46501:1-10 doi:10.1063/1.3499939 (2010).
Tathagata, Ray et al. Low Power, High Throughput Continuous Flow PCR Instruments for Environmental Applications. (Retrieved from the Internet: Jan. 10, 2018) Dec. 1, 2013, pp. 1-181.
U.S. Appl. No. 16/413,416 Final Office Action dated Jul. 26, 2021.
U.S. Appl. No. 16/413,416 Non-Final Office Action Dec. 22, 2020.
U.S. Appl. No. 16/413,416 Notice of Allowance Apr. 8, 2022.
U.S. Appl. No. 17/827,614 Notice of Allowance Nov. 22, 2022.
U.S. Appl. No. 18/111,342 Office Action dated Sep. 7, 2023.

\* cited by examiner

SYSTEMS AND METHODS RELATED TO CONTINUOUS FLOW DROPLET REACTION

CROSS-REFERENCE

This application is a continuation of U.S. application Ser. No. 18/111,342 filed on Feb. 17, 2023, which is a continuation of U.S. application Ser. No. 17/827,614 filed on May 27, 2022, now U.S. Pat. No. 11,607,689, issued on Mar. 21, 2023, which is a divisional of U.S. application Ser. No. 16/413,416 filed on May 15, 2019, now U.S. Pat. No. 11,413,616, issued on Aug. 16, 2022, which is a continuation of International Application No. PCT/US2017/063293, filed on Nov. 27, 2017, which claims the benefit of U.S. Provisional Application No. 62/439,814 filed on Dec. 28, 2016 and U.S. Provisional Application No. 62/427,086 filed on Nov. 28, 2016, each of which is incorporated herein by reference in its entirety.

BACKGROUND

The quantitation of nucleic acids is an indispensable technique in medical and biological applications. New methods for detecting and quantitating nucleic acids, such as emulsion-based digital nucleic acid amplification, including emulsion-based polymerase change reaction (PCR), provide greater accuracy and convenience as compared to traditional nucleic acid amplification, such as traditional polymerase chain reaction (PCR) methods. Specifically emulsion-based digital nucleic acid amplification allows for absolute quantification of nucleic acid sequences in samples that is highly accurate. Performing emulsion-based digital nucleic acid amplification in most systems, however, still requires preparation of samples in which nucleic acid is combined with primers or probes before analysis by emulsion-based digital nucleic acid amplification.

SUMMARY

Provided herein are systems, and related methods, for detecting and quantitating nucleic acids using a continuous-flow instrument. An analysis system as described herein can be a continuous-flow instrument comprising all components for a desired chemical reaction, such as nucleic acid amplification, including at least one of PCR and reverse transcription PCR (RT-PCR), and detection of products of the desired chemical reaction.

Systems, devices and related methods herein facilitate rapid, reliable, accurate point of contact analysis of samples. Samples are analyzed using minimal pre-input processing, so as to facilitate analysis under field conditions or when a sample preparation environment is not feasibly laboratory non-lab conditions. Substantial sample processing is internal to the device, such that a 'blood-in data-out' workflow is achievable having minimal external sample processing. Streamlined sample processing allows data acquisition to occur rapidly at a point of care such as a clinical environment, or at a point of sample acquisition such as a field site or epidemic site. Because sample processing is minimal, there is in some cases no need for samples to be sent to a lab for processing prior to applying samples to the device. Cost, processing time, level of expertise of the user, risk of human error in sample processing, and risk to a lab technician in processing an infectious or otherwise hazardous sample is dramatically reduced.

Some analysis systems herein configured are to perform emulsion-based digital nucleic acid amplification. Analysis systems often comprise storage areas configured to store all reagents used for chemical reactions performed on-board the system, and include all device components for the chemical reactions on-board the system. Thus, a user may provide a sample comprising target nucleic acids to the system, and the system can perform emulsion-based digital nucleic acid amplification without further reagent input from the user. In some embodiments, the system can be configured to include reagents for pre-processing a sample containing target nucleic acids, such as reagents for nucleic acid purification and/or extraction (e.g., cell lysis). For example, cells, blood, respiratory fluid, and/or urine can be pre-processed by the system to extract DNA or RNA without having to use a different tool for the pre-processing. Often systems as described herein are portable. Systems as described herein allow for processing of target nucleic acid samples without exposing the samples to external contamination. The system can be configured to provide accurate and automated injection of desired volumes of sample nucleic acids and/or reagents for the process flow. Accurate and automated injection of desired quantities of sample nucleic acids and reagents provided by the systems enable compact, portable, continuous-flow processing of the sample nucleic acids on-demand in the field and/or as a desktop tool in hospitals and research laboratories.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Figure 1:
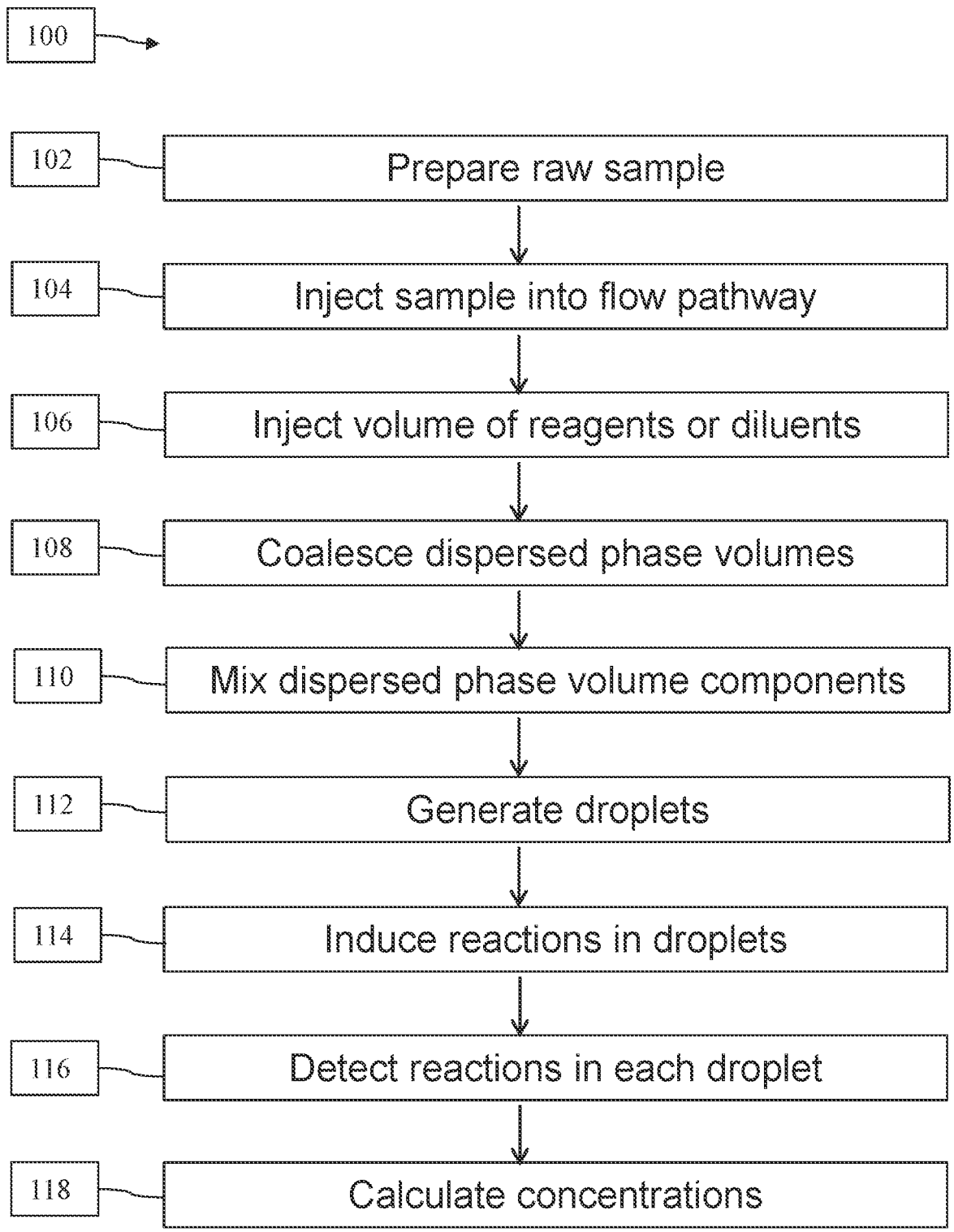
FIG. 1 depicts a process workflow.

Provided herein are systems and related methods for performing continuous-flow emulsion based chemical reactions. In some embodiments, one or more systems described herein are configured to perform desired chemical reactions in droplets, including chemical reactions for analysis of target analyte, such as nucleic acids, in samples provided to the systems, and/or for chemical synthesis, including chemical synthesis of drug compounds. In some embodiments, one or more systems described herein are configured to perform chemical reactions for processing a fluid sample comprising analyte of interest. Systems as described herein can be configured to perform chemical reactions to extract or to quantify the analyte of interest without providing analysis of the analyte. Systems as described herein can be configured to perform a lysis reaction to extract target nucleic acids from cells, without performing analysis of the target nucleic acids. Systems as described herein can be configured to further perform analysis of the target nucleic acids. For example, the system may be configured to perform nucleic acid amplification of the target nucleic acids. Systems as described herein can be configured to perform chemical reactions to synthesize target chemical compounds, including synthesis of target drug compounds.

Detection and quantification of nucleic acids by nucleic acid amplification is useful in a variety of research and medical applications. There is a need to be able to detect and quantify nucleic acids rapidly and accurately. Emulsion-based digital nucleic acid amplification allows for higher sensitivity as compared to traditional nucleic acid amplification, such as traditional PCR methods. However, emulsion-based digital nucleic acid amplification often involves manual preparation of target nucleic acid samples and/or reagents, as well as stabilization and transport of droplets across a system.

Provided herein are systems, and related methods, for detecting and quantitating nucleic acids using a continuous-flow instrument in which all components for emulsion-based digital nucleic acid amplification, such as PCR, are self-contained within the system. In some embodiments, an analysis system configured for emulsion-based digital nucleic acid amplification is configured to include all reagents for emulsion-based digital nucleic acid amplification on-board the system. In some embodiments, the system can be configured to include reagents for performing reactions other than emulsion-based digital nucleic acid amplification, including for example reagents for sample nucleic acid purification and/or extraction (e.g., cell lysis). Often systems as described herein are portable. Analysis systems as described herein provide all necessary components for emulsion-based digital nucleic acid amplification without user interference during different stages of system operation. For example, a user can supply to a system as described herein a sample comprising target nucleic acids, and analysis of the sample can proceed in a continuous workflow without any additional fluid and/or consumable handling by a user. Systems as described herein allow for processing of target nucleic acid samples without exposing the samples to external contamination. In some instances, a sample such as water containing cells, blood, respiratory fluid, and/or urine does not need to be pre-processed to extract DNA or RNA before being processed for analysis in a system as described herein.

A sample containing the target nucleic acids can be processed simultaneously for parallel-multiplex detection or processed sequentially for serial-multiplex detection. An analysis system may comprise at least one zero-dead volume injector configured for automatic and accurate injection of the sample nucleic acids and/or reagents. As will be described in further details herein, a zero-dead volume injector may comprise an injection valve such as one with zero-dead volume such that fluids for reaction in the system can be automatically and precisely metered without user interference. The sample of nucleic acids, and reagents, such as primers, probes, polymerase enzymes, and/or free nucleotides can be supplied from a cassette, on-board reservoir, or sample inlets, and can be combined within the system to form droplets, such as reaction droplets, containing sample nucleic acids and reagents for a desired chemical reaction. In some instances, droplets containing sample nucleic acids and droplets containing reagents are supplied to a coalescer where a droplet containing the sample and a droplet containing the reagents are combined to form a reaction droplet containing sample nucleic acids and reagents for a nucleic acid amplification reaction, including PCR, such as whole genome PCR and reverse-transcription PCR (RT-PCR) for RNA. In some embodiments, reaction droplets are flowed from the coalescer to a droplet generator. The droplet generator may fractionate each reaction droplet into multiple droplets, for example to provide droplets of a desired volume. In some embodiments, the droplets can then pass through a reactor in which the chemical reaction is induced within the droplets. For example, the droplets can pass through a thermocycler to amplify a target molecule by a set of primers and probes. In some embodiments, reaction droplets can be flowed from the coalescer to the thermocycler without passing through a droplet generator. The analysis system may comprise one or more detectors downstream of the reactor configured to provide desired analysis of the reaction products within droplets. For example, droplets containing reaction products, or product droplets, can be flowed through one or more detector components such that the contents of the product droplets can be analyzed.

In some embodiments, the detector can be used to determine concentration of reaction products within droplets. Concentration can be analyzed using a Poisson distribution. For example, a droplet comprising at least one copy of a target molecule will fluoresce during detection and count as a digital 1 whereas a droplet that does not fluoresce is counted as a digital 0. A ratio of 1's to total droplets can then be calculated and corrected for Poisson statistics and injected volume to give an absolute concentration.

As described herein, in some embodiments, an analysis system can be configured to provide multiplexing. Multiplexing allows for a single sample to be analyzed multiple times, which can be useful for diagnostic purposes. As described herein are systems that allow for multiplexing are configured to enable detection for targets in serial and/or in parallel from a single initial sample. In some instances, the analysis system is configured for detection of target nucleic acids in parallel such that multiple targets in a sample are analyzed simultaneously. For example, in parallel multiplexing, the system may comprise a detector comprising more than 1 photodetector configured to measure more than one emission frequency from a target nucleic acid and/or emission frequency from more than one target nucleic acid. In some instances, serial multiplexing comprises analyzing multiple targets sequentially. Sometimes, serial multiplexing is performed using multiple detectors in a series in a flow pathway. A sample that is analyzed by parallel multiplexing and/or serial multiplexing can be further analyzed by serial and/or parallel sample multiplexing. In some embodiments, the initial sample can be sub-sampled for serial multiplexing. Serial sample multiplexing can be used to analyze multiple targets in a first aliquot, and then based on results analyze different targets in a second aliquot. For example, a first aliquot of a sample could be analyzed for some common set of targets. If negative for those targets, the system can be configured to inject a second aliquot of sample to detect for presence of a second set of less common targets. The process can progress with additional aliquots and additional tests. In some instances, serial sample multiplexing is accomplished by combining multiple sets of primers and probes. In some instances, systems described herein use multicolor detection to analyze a sample. Systems and methods as described herein can save labor cost and time while being able to assay for a number of targets from a single sample.

Described herein are systems of quantitating nucleic acids that are more robust and have a wider dynamic range than previous systems. Use of previous systems often required manual dilution, calculation of concentration, and/or re-assaying. Systems as described herein include one or more components which enable automated analysis. In some embodiments, a system can include a controller can be used to control one or more of timing and volume of injections, application of external source to a coalescer, parameters for a reactor including reaction time, and processing of signals from a detector. For example, a controller can adjust an amount of diluent added to a dispersed phase. In some cases, a controller is a state machine. A controller can allow for multiple volumes of a dispersed phase to serially traverse a reaction flow pathway. In some instances systems are automated to allow for detection and quantification to be accomplished using an internal feedback loop. For example, if a first aliquot of sample is outside a detectable range, the system would automatically adjust parameters such as quantity and concentration and would inject a second aliquot.

As compared to traditional emulsion-based digital nucleic acid amplification systems, systems described herein can allow a reaction to occur with little or no contamination. This is important for providing biological assays which can demonstrate desired accuracy and/or reliability, including biological assays used for research and/or clinical diagnoses.

In addition to nucleic acid amplification, systems and methods as described herein can be used for automated drug synthesis. For example, a first drug precursor in a first volume of dispersed phase is combined with a second drug precursor in a second volume of dispersed phase in a coalescer.

Systems and methods described herein can enable automated continuous flow reactions without or substantially without manual measurement and/or pipetting of samples and/or reagents for the chemical reactions. The systems may be pre-loaded with reagents compatible with the samples for the chemical reactions. The systems may be configured to automate pre-processing of the samples and accurate measurement of reagents for the chemical reactions. For example, a sample comprising target nucleic acids can be provided to the systems and the systems can perform all processes to achieve the desired chemical reactions, and/or to provide the desired analysis of the sample. The chemical reactions can be performed without or substantially without manual sample quantification and/or manipulation.

Automated Dynamic Ranging of the Device

Digital PCR typically suffers from a low overall dynamic range relative to real-time PCR. One reason for this is that it is difficult to obtain a proper sample input concentration so as to obtain an appropriate distribution of analytes among droplets to be analyzed.

Analytes often e exhibit a Poisson distribution in the droplets into which they are subdivided. Quantification of the concentration of a specific sequence of DNA in a sample is determined by correlating the ratio of unfilled partitions to total partitions to the underlying Poisson distribution. Because partitions filled with one, two, or more molecules of DNA are indistinguishable due to the digital nature of the quantification (that is, they all quantify to "one," or to "present"), only unfilled partitions can give a measure of the central parameter in the Poisson distribution and, from that, the original concentration of a specific sequence of DNA in the sample of interest. If the original concentration is too high relative to the number of partitions generated, all or most of the partitions will quantify as "one", which complicates quantification and may render it impossible.

The automated nature of this invention allows for the dynamic range of measurement to be much larger than in typical digital PCR. In particular, samples are applied to the device, an aliquot is processed, and the resulting data is analyzed. If sample analytes are present at too high a density, a second aliquot of the sample, already in the device in some cases, is diluted and processed, so as to reduce the number of droplets having multiple analyte molecules in a single droplet, hindering analysis. Alternately, if sample analytes are present at too low a concentration in an aliquot, as evidenced by too high a number of 'droplets empty of sample or signal, then a more concentrated aliquot of the sample in the device is processed in a following iteration, so as to come to an optimal or improved analyte concentration for downstream analysis.

In a high dynamic range example, a first aliquot of sample is drawn into the instrument, automatically mixed with reagents such as PCR reagents, partitioned, thermocycled, and measured. An automatic controller then determines the next step. If the average number of molecules per partition is in an acceptable error range for the downstream analysis such as digital PCR, the measurement is accepted. This acceptable range is between 0.0001 and 5 molecules per partition in many applications, such as some PCR applications. If the average number of molecules per partition is greater than that in the acceptable error range, the error of measurement will either be high or the sample will be unquantifiable (that is, all or too many partitions or droplets are measured as "one" or as "present" for an analyte even when multiple analytes are in a single partition).

A second aliquot of sample is drawn, and the system will automatically mix with both analysis or reaction reagents, such as PCR reagents, and dilution water or other suitable diluent from an onboard reservoir. The amount of dilution is selected automatically so as to bring the average number of molecules per partition back into an acceptable or analytically meaningful range. In some cases, the dilution amount will dilute the sample to between a fraction of 0.1 and 0.5 of an original or prior concentration. The second aliquot of sample is then partitioned, thermocycled or otherwise subjected to reaction conditions, and measured in the resulting partitions. If the average number of molecules per partition is in an acceptable error range, the measurement is accepted; if the average number of molecules per partition is still too high, the process is repeated. If the average number of molecules per partition is too low, then a lower dilution factor is selected. Alternatively, for the first aliquot, if the number of partitions measuring "one" is zero, it is possible that the concentration was too low so as to induce sampling error (that is, the aliquot injected did not contain any of the target molecule, although the sample did have small amounts of the target molecule). In this case, the system can reinject a second aliquot of sample of larger volume than the first, so as to increase the probability that, if the target molecule were to be in the sample, it would be detected. In this way, the dynamic range of the device for a given reaction, such as digital PCR or other molecular reaction or analysis, can be automatically expanded well beyond the boundaries of instruments available in the art, up to and beyond the dynamic range of real-time PCR.

Manually achieving a comparable result in other digital PCR instruments can be achieved, by manually mixing together a first aliquot of sample and PCR reagents, manually running the instrument to determine the average number of target molecules per partition, and, if too high for accurate quantification, manually diluting the sample so as to achieve an acceptable average number of target molecules per partition. However, manually achieving a comparable result requires a significantly higher amount of manual interface and labor with the instrument. This introduces the possibility of human error and variability, both in the calculation and measurement of the dilution amounts as well as the introduction of contamination. An increased amount of manual manipulation also decreases the range of locations in which the device can be deployed, as an increase in manual manipulation often corresponds with an increased need for a suitable laboratory environment, which may be inconsistent with direct, immediate point of care analysis or with sample analysis in the field or at the site of collection. This device eliminates or dramatically reduces the amount of manual manipulation, thus reducing the possibility of manual error, risk to user, time to result and variability, and outside contamination.

Automated aliquoting adds additional utility to the devices and methods disclosed herein. For example, there are added benefits in cases where one is considering measurements for multiple targets where a first set of one or more targets is at a substantially different concentration, such as much rarer, than a second set of one or more targets. In these situations, it is often beneficial to test for the most likely or more abundant targets first so as to reduce cost and interpretation expense. For example, in a diagnostic situation a hospital laboratory may have a patient with respiratory symptoms; it would make sense to test for normal cold and flu viruses before progressing to testing for rarer illnesses, such as bacterial meningitis. This is particularly so if the rarer illness is likely to be caused by or associated with an analyte that is present at a lower or much lower concentration in a patient sample.

To achieve this, the system injects a first aliquot of sample and automatically mixes it with detection reagents such as PCR reagents, including in some cases up to four or more primer and probe pairs associated with up to four or more targets from the first set. The first aliquot is partitioned, thermocycled, and measured, or other reaction and detection approaches are taken. If the concentration of at least one target in the first set is above a first threshold, then a diagnosis is made of the condition associated with that target, or steps can be taken to independently investigate the presence of a disorder associated with the detected analyte. If no target is above a concentration threshold associated with that target, then the system injects a second aliquot and mixes it with PCR reagents, including up to four or more primer and probe pairs associated with up to four or more targets from the second set. The second aliquot is partitioned, thermocycled, and measured, or other reaction and detection approaches are taken. If the concentration of at least one target in the second set is above a second threshold associated with that target, then a diagnosis is made of the condition associated with that target, or steps can be taken to independently investigate the presence of a disorder associated with the detected analyte. This process can be extended or iteratively performed, including progressively rarer targets from a third set, a fourth set, and so on, so as to reduce the time to diagnose common targets as well as the cost associated with complex and comprehensive assays. A benefit of this approach is that a panel of diseases or disorders or ailments can be assayed for from a single sample in succession rather than in parallel, such that more likely diseases or disorders are assayed for first, and reagents for the detection of rarer disorders are expended only when the initial, more likely disorders have been ruled out because of the failure to detect an associated analyte in the sample. That is, a single sample is analyzed in series rather than in parallel, in some cases for markers such as nucleic acid markers of successively rarer disorders, and only until an analyte associated with a likely cause of a disorder or otherwise a marker of a disorder is detected in a sample. As the system is automated, this is done with a minimum of manual labor in sample processing, and so as to reduce or minimize the amount of reagent used, because reagents for the detection of analytes associated with rare or unlikely disorders are consumed only when more common or more likely disorders have been assayed for and found not to be present.

Systems and Methods

FIG. 1 depicts an exemplary work flow 100 of detecting and/or quantifying target nucleic acids using one or more analysis systems described herein. In some cases, a concentration of the target nucleic acids is unknown. Referring to FIG. 1, in block 102, a raw sample can be prepared. In some embodiments, preparation of the raw sample can be performed on-board the system. For example, the system can include one or more components be configured to store reagents for the preparation of the raw sample. A raw sample, such as blood, urine, serum, lymph, saliva, and/or perspiration, containing target nucleic acids can be directly provided to the analysis system for processing. In block 104, a sample including the target nucleic acids can be injected into flow pathway of the analysis system. In some embodiments, the system can comprise a zero-dead volume injector configured to inject a desired volume of the sample into the flow pathway. The zero-dead volume injector may be configured to form an emulsion comprising the sample nucleic acids in a dispersed phase. In some embodiments, the injector can be configured to form a first population of droplets comprising the sample nucleic acids in a continuous phase. In block 106, a volume of reagents and/or diluents can be injected into the pathway of the analysis system. In some embodiments, the system can comprise a zero-dead volume injector configured to inject a desired volume of the reagents into the flow pathway. The zero-dead volume injector may be configured to form an emulsion comprising reagents in a dispersed phase. In some embodiments, the injector can be configured to form a second population of droplets comprising reagents in a continuous phase. The continuous phase may be the same as that of the first population of droplets comprising the sample nucleic acids. The zero-dead volume injector may the same as or different from that used for the sample.

In block 108, dispersed phase volumes can be coalesced. For example, a first dispersed phase and a second dispersed phase can be coalesced. In some embodiments, the system comprises a coalescer configured to merge components of at least one dispersed phase to provide a merged droplet. In some embodiments, the merged droplet contains nucleic acids and reagents suited for a desired chemical reaction (e.g., nucleic acid amplification, including PCR). For example, a droplet from the first population can be merged with a droplet of the second population. In block 110, dispersed phase volume components can be mixed. In some embodiments, mixing within the merged droplets can be induced to facilitate desired distribution of reagents and/or sample nucleic acids within the droplets. In some embodiments, mixing is performed to facilitate uniform distribution of reagents and/or nucleic acids within the droplets. In block 112, droplets can be generated. In some embodiments, multiple droplets can be generated from a merged droplet, such as to provide droplets of desired volumes for downstream processing in the system. Each of the multiple droplets may have the nucleic acids and reagents for a desired chemical reaction (e.g., nucleic acid amplification, including PCR). In block 114, reaction within the droplets can be induced. For example, droplets containing nucleic acids and reagents can be flowed through a reactor of the analysis system such that reaction within the droplets can be induced. In some embodiments, the reactor comprises a thermocycler. For example, droplets can be flowed through the thermocycler to induce desired nucleic acid amplification reaction within the droplets. In block 116, detections of products of the reactions can be performed. Droplets containing products of the reaction can be flowed through the detector such that the products within the droplets can be sensed. In block 118, a concentration can be calculated. The concentration of reaction products within droplets can be calculated based on information provided by the detector.

In some instances, a target molecule is a nucleic acid. For example, a target molecule is deoxyribonucleic acid (DNA) or ribonucleic acid (RNA). Target nucleic acids processed by one or more systems as described herein can be free-floating or contained within a living organism or non-living organism. In some embodiments, one or more systems as described herein can be configured to extract target nucleic acids containing within a living or non-living organism. For example, the one or more systems can be configured to perform a lysis reaction. In some cases, lysis is performed on-board the system. In some instances, the one or more systems can include a reservoir containing a lysis agent. Lysis can be performed mechanically, enzymatically, chemically, thermally, sonically, ultrasonically, or some combination thereof. For example, a chemical lysis agent is used to decompose proteins, lipids, and/or other non-nucleic acid materials in the system. Subsequent to the lysis reaction, a filtration step can be performed within the system for filtering products of the lysis reaction such that the nucleic acids of interest can be retained for further processing within the system.

In some cases, lysis is performed in an off-board system. In some cases, components of a lysis system can be disposable. Alternately or in combination, lysis is performed by a user such as by a laboratory personnel.

In some instances, the target nucleic acids are separated from cells, viruses, or microbes. In some instances, target nucleic acids are isolated from bodily fluids of a subject (e.g., blood, urine, serum, lymph, saliva, and/or perspiration). In some cases, target nucleic acids are isolated from tissue. In some embodiments, target nucleic acids are isolated from cells by lysis and subsequent filtration as described herein.

In some embodiments, the isolated nucleic acids can be encapsulated within an aqueous fluid. The encapsulated nucleic acids in some instances are then mixed with an immiscible fluid to form an emulsion. For example, isolated nucleic acids can be contained in the disperse phase of the emulsion. In some instances, an immiscible fluid is oil. Exemplary oils are fluorinated oils, silicone oils, hydrocarbon oils, and/or mineral oils. In some cases, the immiscible fluid comprises oil and one or more surfactants. In some cases, differential density of the immiscible fluid and the aqueous fluid allows separation of the two fluids by gravity.

Injector

Figure 2:
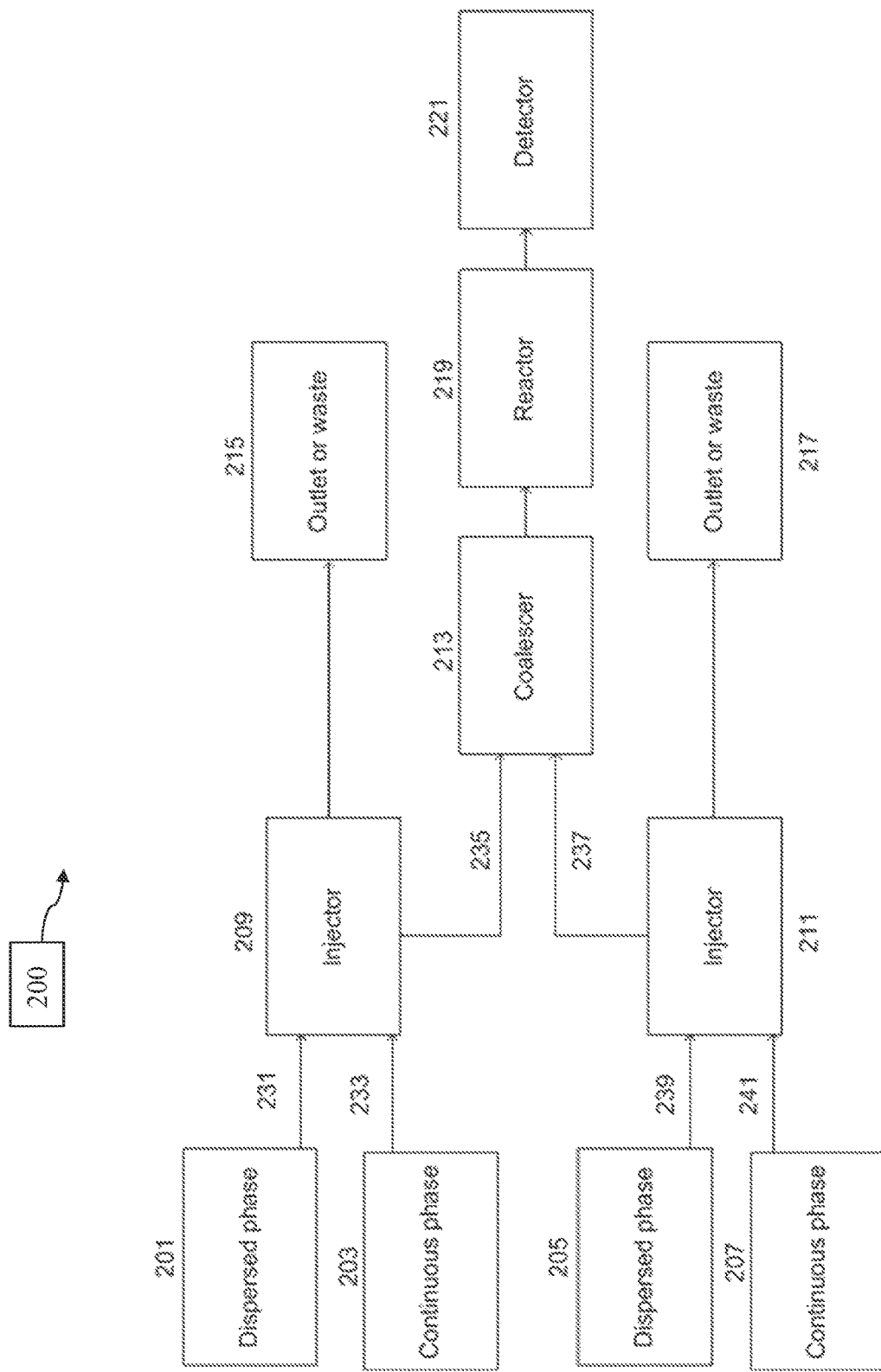
FIG. 2 depicts an exemplary arrangement of components of a system.

Samples containing DNA or RNA in most cases are introduced into systems as described herein through an injector valve. FIG. 2 depicts a schematic diagram of an exemplary system 200, according to some embodiments. The system 200 includes a reservoir for a first dispersed phase 201, a reservoir for a first continuous phase 203, a reservoir for a second dispersed phase 205, a reservoir for a second continuous phase 207, a zero-dead volume injector 209, a second zero-dead volume injector 211, a coalescer 213, a reactor 219, and a detector 221.

The reservoir for the first dispersed phase 201 and the reservoir for the first continuous phase 203 are configured to supply the first dispersed phase and first continuous phase, respectively, to the first zero-dead volume injector 209. The reservoir for the second dispersed phase 205 and the reservoir for the second continuous phase 207 are configured to supply the second dispersed phase and the second continuous phase, respectively, to the second zero-dead volume injector 211. In some embodiments, the first dispersed phase and the second dispersed phase can be an aqueous solution comprising nucleic acids for analysis by the system 200 and/or reagents for chemical reactions to enable analysis of the nucleic acids. In some embodiments, the first continuous phase and the second continuous phase may comprise one or more oils and/or one or more surfactants.

Referring to FIG. 2, a first inlet 231 of the first zero-dead volume injector 209 is in fluid communication with an outlet of the reservoir of the first dispersed phase 201 and a second inlet 233 of the first zero-dead volume injector 209 is in fluid communication with an outlet of the reservoir of the first continuous phase 203. The first zero-dead volume injector 209 comprises a first dispersed phase and a first continuous phase. The first dispersed phase and first continuous phase formed by the zero-dead volume injector 209 can leave through an outlet 235 of the zero-dead volume injector 209 for further processing within the system 200.

The zero-dead volume injector 209 can be in fluid communication with the coalescer 213 and/or a first outlet or waste 215. In some embodiments, at least a portion of the first dispersed phase and continuous phase formed by the first zero-dead volume injector 209 is supplied to the coalescer 213. In some embodiments, at least a portion of a first dispersed phase and a first continuous phase formed by the first zero-dead volume injector 209 is supplied to the first outlet or waste 215. Sometimes a connection is a tee-junction. In some instances, a first dispersed phase and first continuous phase from the first outlet or waste 215 is collected in a waste reservoir or discarded. In some instances, the first dispersed phase and first continuous phase from the first outlet or waste 215 can be recycled to be used again. In some cases, the first outlet or waste 215 comprises tubing and a pump. In some embodiments, a dispersed phase is recycled to a dispersed phase container. This dispersed phase container can be a source of dispersed phase 201. Alternately or in combination, a dispersed phase container is removable to allow for further reactions or assays to be done on samples contained in a dispersed phase container.

Referring to FIG. 2, the second dispersed phase can comprise a second component of a chemical reaction. A first inlet 239 of the second zero-dead volume injector 211 can be configured to receive the second dispersed phase from the reservoir for the second dispersed phase 205. In some embodiments, a second inlet 241 of the second zero-dead volume injector 211 is configured to receive the second continuous phase from the reservoir for the second continuous phase 207. In some instances, the first continuous phase and the second continuous phase can be stored in the same reservoir. As will be described in further details herein, the second zero-dead volume injector 211 can be configured to form a second dispersed phase and a second continuous phase. The second zero-dead volume injector 211 can comprise an outlet 237 configured to supply at least a portion of a second dispersed phase and a second continuous phase to the coalescer 213. In some embodiments, the system 200 can be configured to supply at least a portion of a second dispersed phase and a second continuous phase to an outlet or waste 217. The outlet or waste 217 may be in fluid communication with that is connected to waste, is recycled, or is connected to a storage container.

As will be described in further details herein, the coalescer 213 can be configured to coalesce dispersed phase volumes, such as droplets of dispersed phases. The coalescer 213 can be in fluid communication with the reactor 219. The reactor 219 can be configured to induce chemical reaction. The reactor 219 can be in fluid communication with the detector 221 such that products of the chemical reaction induced by the reactor 219 can be observed and/or analyzed by the detector 221.

A reaction flow pathway can be comprised of various materials. In some instances, a reaction flow pathway comprises a microbore tube constructed of polymers such as silicone or polyvinyl chloride (PVC). A diameter of a tube can be at least 0.05, 0.10, 0.15, 0.20, 0.25, 0.50, 0.75, 1.0, 1.5, 2.0, 2.5, 3.0, or more than 3.0 mm. In some instances, a diameter of a tube is at most 0.05, 0.10, 0.15, 0.20, 0.25, 0.50, 0.75, 1.0, 1.5, 2.0, 2.5, 3.0, or more than 3.0 mm. A diameter of a tube can be about or within a range spanning 0.05, 0.10, 0.15, 0.20, 0.25, 0.50, 0.75, 1.0, 1.5, 2.0, 2.5, or 3.0 mm. A reaction flow pathway in some cases comprises a set of flow channels milled or etched into a material. Materials can include glass, silicon, metal, ceramic, or other materials, and channels, for example, are created by at least one of ablation, etching, molding, drilling, or poking. In some instances, a reaction flow pathway comprises segments of tubing and segments of flow channels formed into a material.

In some instances, the reservoir of the first continuous phase 203 and the reservoir of the second continuous phase 205 can comprise at least one of a syringe, and/or container, including a single-dose container or a refillable container. In some embodiments, a pressure source is used to inject a continuous phase through the system 200. A pressure source can be a pump, such as a syringe, diaphragm, a peristaltic, a reciprocating, a centrifugal, and/or a vacuum pump. In some instances, the system 200 includes a controller configured to control operation of one or more components the system 200, including for example refilling one or more of the reservoirs 201, 203, 205, and 207. For example, the controller may be configured to control a pump such that a reservoir is automatically refilled, such as when there is a low level in a syringe pump, for example following a completed injection, and/or following a completed reaction.

Figure 3:
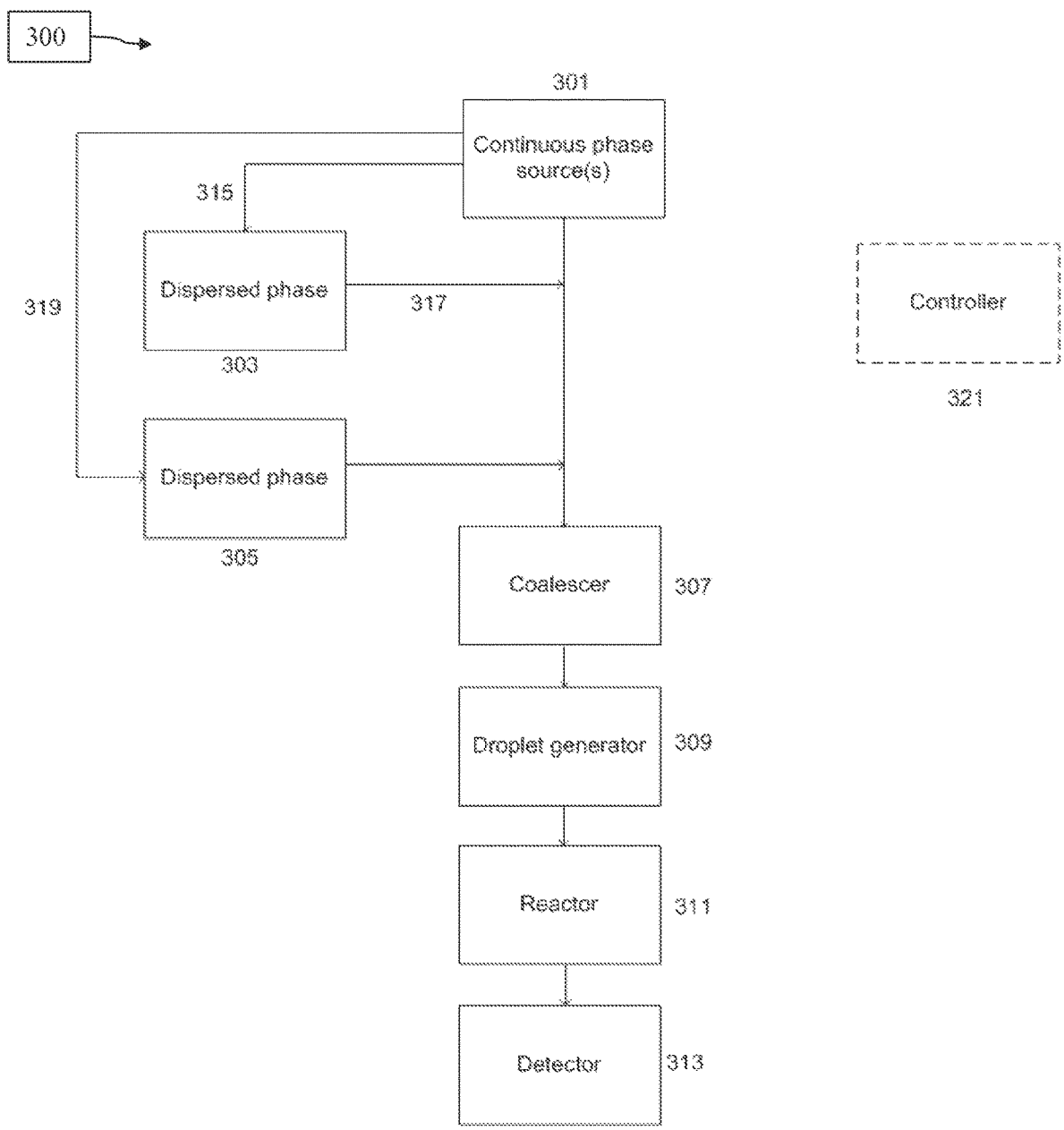
FIG. 3 depicts an exemplary arrangement of a system for conducting an assay, the system comprising a coalescer, droplet generator, reactor, detector, and a controller.

FIG. 3 is a schematic diagram of an exemplary system 300, according to some embodiments. In some embodiments, a system performs reaction assays according to a Poisson distribution. As shown in FIG. 3, the system 300 can include a continuous phase source 301, a first dispersed phase source 303, a second dispersed phase source 305, a coalescer 307, a droplet generator 309, a reactor 311 and a detector 313. In some embodiments, the continuous phase source 301 can be configured to be in fluid communication with an inlet of the first dispersed phase source 303, such as via fluid channel 315. A first dispersed phase and a first continuous phase can be combined. In some embodiments, the continuous phase source 301 can be configured to be in fluid communication with an inlet of the second dispersed phase source 305, such as via fluid channel 319. In some instances, a second dispersed phase and a second continuous phase are combined. An emulsion comprising a first and second dispersed phase and a first and second continuous phase can be supplied to the coalescer 307. The first and second continuous phases can have the same composition. For example, the first and second dispersed phase may be in a common continuous phase. The coalescer 307 can be in fluid communication with the droplet generator 309. The droplet generator 309 can be in fluid communication with the reactor 311. The reactor 311 can be in fluid communication with the detector 313.

The system 300 may include a controller 321 configured to control operation of one or more components of the system 300, such as one or more of the first continuous phase source 301, first dispersed phase source 303, second dispersed phase source 305, coalescer 307, droplet generator 309, reactor 311 and detector 313.

Figure 4:
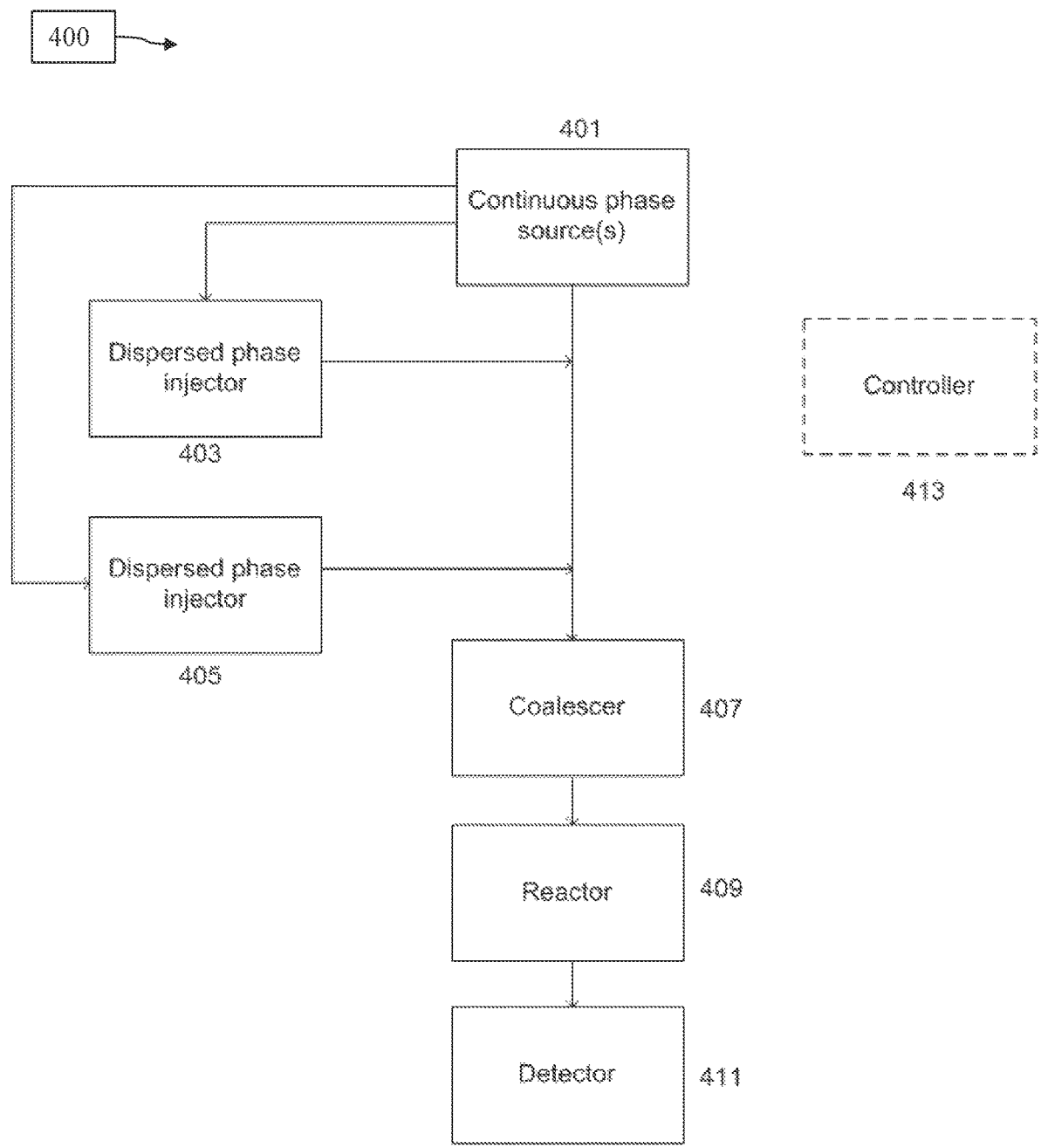
FIG. 4 depicts an exemplary arrangement of a system comprising a coalescer, reactor, detector, and controller.

FIG. 4 is a schematic diagram of another exemplary system 400, according to some embodiments. In some embodiments, a system performs reactions on dispersed phases not partitioned into droplets. The system 400 can include a continuous phase source 401, a first dispersed phase source 403, a second dispersed phase source 405, a coalescer 407, a reactor 409 and a detector 411. The flow pathway of the system 400 is similar to that of system 300 as described with reference to FIG. 3, except that the flow pathway does not include a droplet generator. Fluid flows from the coalescer 407 to the reactor 409 without flowing through a droplet generator. The system 400 can include a controller 413 to control operation of one or more of its components.

Figure 5:
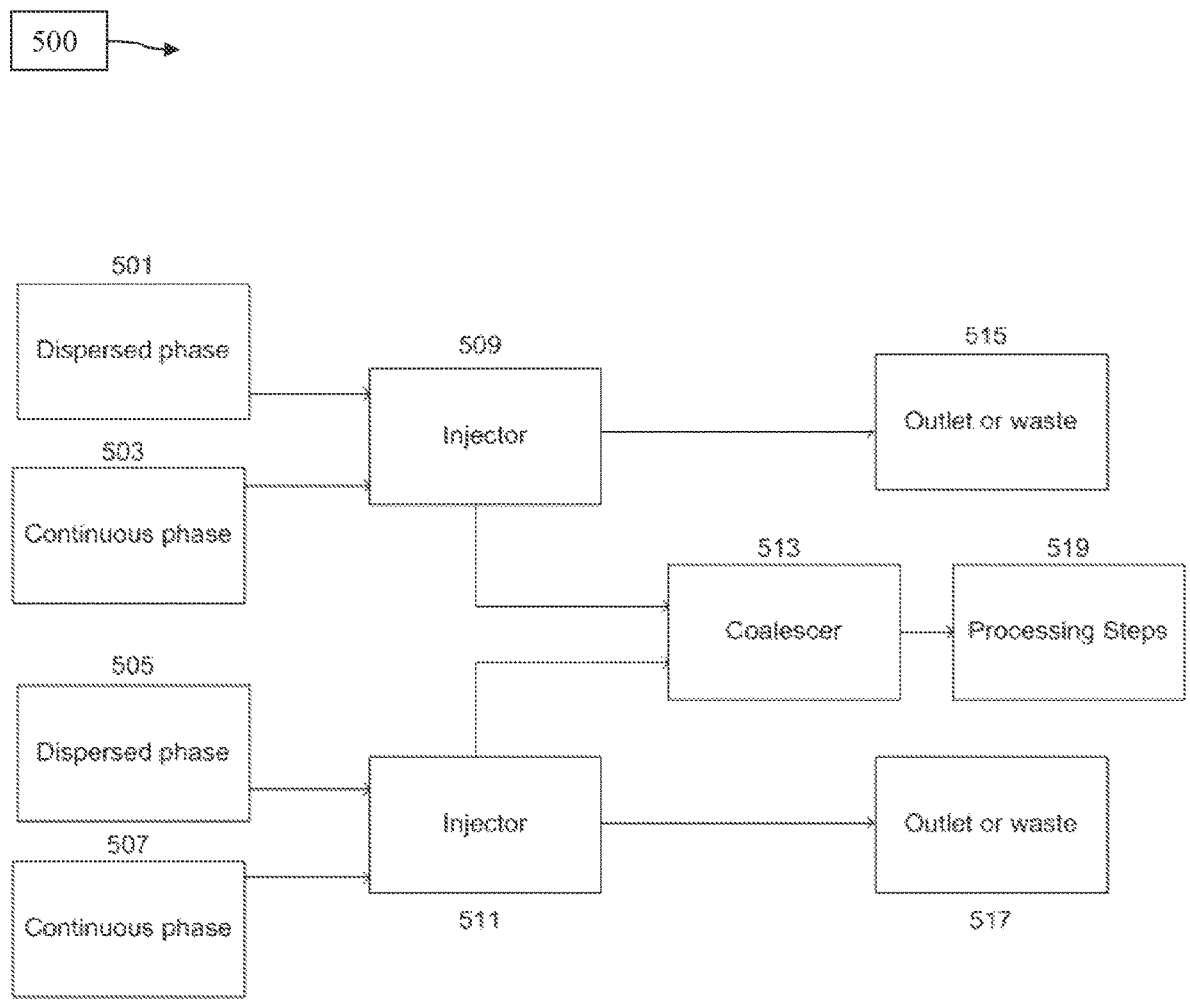
FIG. 5 depicts an injector arrangement comprising independent injectors.

In some embodiments, a system can have independent injectors for forming a desired emulsion. For example, injectors can be arranged independently as in FIG. 5.

Figure 6:
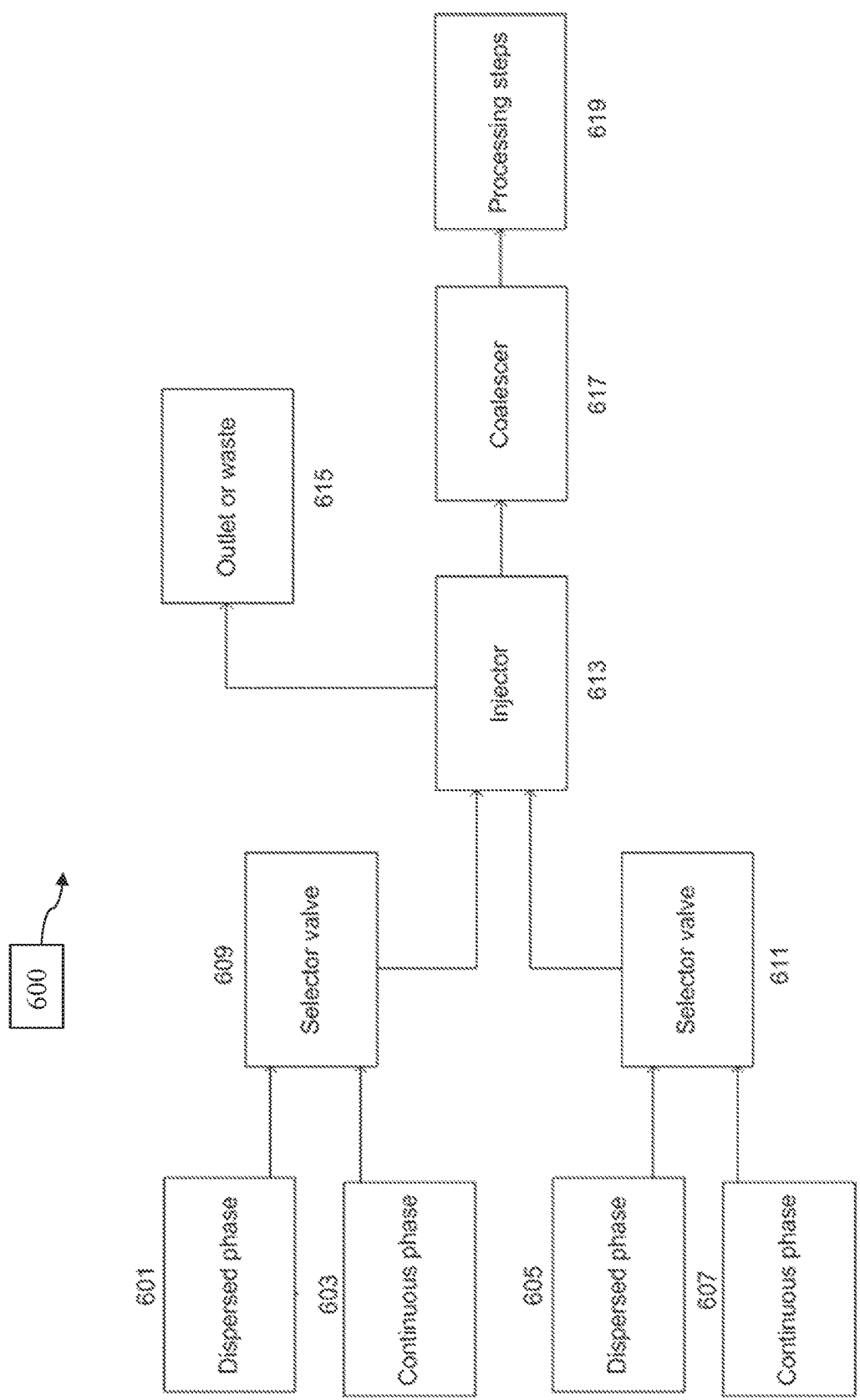
FIG. 6 depicts an injector arrangement comprising a same injector with switching.
Figure 7:
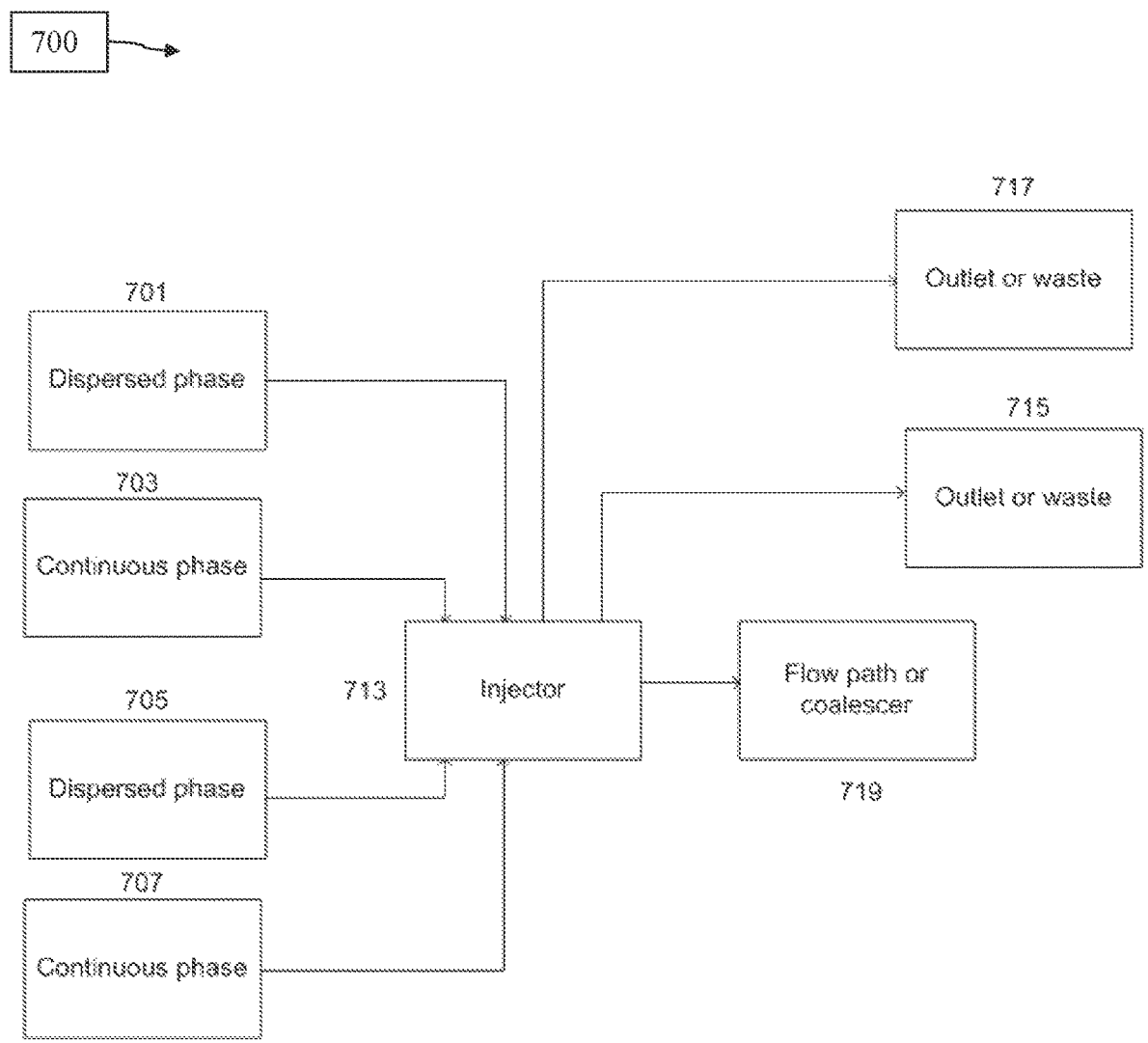
FIG. 7 depicts an injector arrangement comprising an injector with multiple ports.

In some embodiments, one injector can be used to inject more than one dispersed phase. In some embodiments, as shown in FIG. 6, a system can include selector valves configured to control flow into the one injector. In some cases, a system can include an injector having multiple ports, such as shown in FIG. 7. Sometimes there is at least 1, 2, 3, 4, 5, 6, 7, 8, or more than 8 injectors. In some cases, there is at least 1, 2, 3, 4, 5, 6, 7, 8, 9, 10, or more than 10 ports. Sometimes there is at least, about, at most, or within a range spanning 1, 2, 3, 4, 5, 6, 7, or 8 injectors. In some cases, there is at least, about, at most, or within a range spanning 1, 2, 3, 4, 5, 6, 7, 8, 9, or 10 ports.

Injector

A zero-dead volume injector, such as the zero-dead volume injectors as described above, can have multiple flow paths therethrough. A flow path can contain at least one inlet and at least one outlet. In some instances, an inlet allows for a volume of fluid, such as a volume of fluid comprising sample nucleic acids and/or reagents, to be introduced into the system from an external source. For example, a source for the sample nucleic acids and/or reagents can be external to the system. In some embodiments, the inlet allows for sample nucleic acids and/or reagents to be transferred from a reservoir on-board the system to one or more downstream components of the system. Alternately or in combination, an outlet is for waste. In some cases, one or more pumps can be used to load the sample nucleic acids and/or reagents into the injector and/or to flow the sample nucleic acids and/or reagents into a downstream component. For example, sample nucleic acids can be loaded in an inlet of the injector using an introduction pump.

In some instances, multiple flow paths are used at the same time. In some instances, an injector has at least 1, 2, 3, 4, 5, 6, 7, or 8 flow paths. In some instances, an injector has up to 1, 2, 3, 4, 5, 6, 7, or 8 flow paths. In some instances, an injector has about or within a range spanning 1, 2, 3, 4, 5, 6, 7, or 8 flow paths. Exemplary flow paths allow for sample to be loaded or injected.

A flow path in some instances is selected manually. In some cases, a flow path is selected automatically. In some cases, software is used to automatically or manually select a flow path. A flow path may be selected based in part on the desired volume of the fluid to be injected into the system. Sometimes software contains information to adjust for injection volume based on pre-loaded formulas. In some cases, a user does not provide additional input after the sample nucleic acids and/or reagents are provided. For example, the system can be configured to select the flow path in the injector based in part on the type of the sample and/or reagents provided. Use of multiple flow paths often allows for flexibility in quantifying the fluid, a greater dynamic range, specifically when there are different concentrations of a target molecule.

Figure 8:
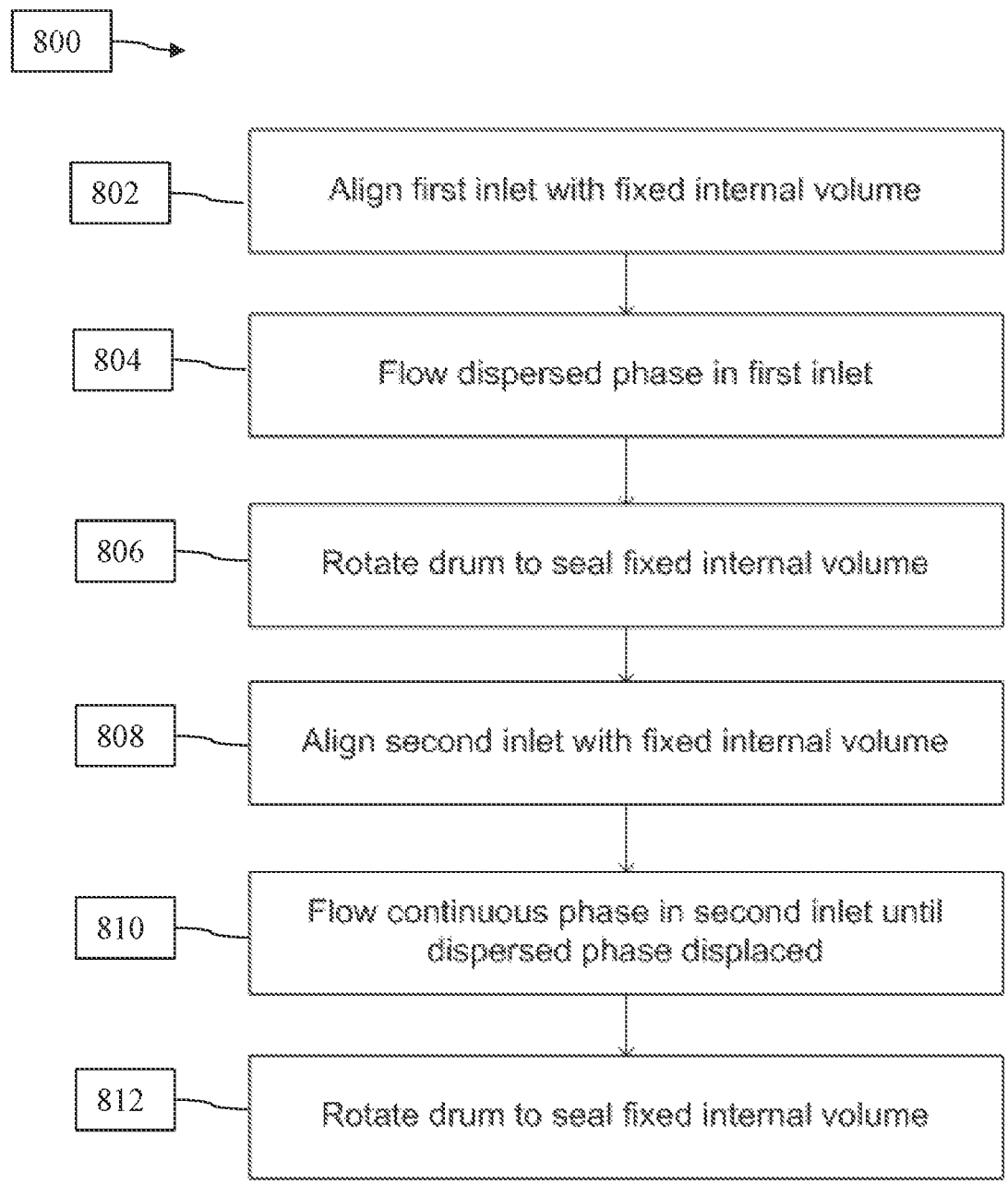
FIG. 8 depicts a process workflow for using an injector.

FIG. 8 depicts an exemplary workflow 800 for operation of an injector, according to some embodiments. In block 802, a first inlet of the injector can be aligned with a fixed internal volume of a drum of the injector. In block 804, a dispersed phase can be flowed through the first inlet of the injector. For example, the dispersed phase can be flowed through the first inlet of the injector and into the fixed internal volume until the fixed internal volume is filled by the dispersed phase. The volume of the dispersed phase in the fixed internal volume is equal to or substantially equal to that of the fixed internal volume. In block 806, the drum can be rotated to seal the fixed internal volume of the drum. In block 808, a second inlet of the injector can be aligned with the fixed internal volume. In block 810, a continuous phase can be flowed through the second inlet until the dispersed phase is displaced. For example, the second inlet can be in fluid communication with a source for a continuous phase and the fixed internal volume can be in fluid communication with an outlet configured to provide fluid flow a downstream component. The continuous phase can be flowed from the continuous phase source into the fixed internal volume, the continuous phase pushing out the dispersed phase already in the fixed internal volume. The continuous phase can be flowed until the continuous phase fills the fixed internal volume and displaces all of the dispersed phase. The volume of the continuous phase flowed to displace the dispersed phase can be equal to or substantially equal to that of the fixed internal volume. In block 812, the drum can be rotated to seal the fixed internal volume.

In some instances, an inlet tube is connected to an injector. Sometimes an injector is a rotary valve. An injector can have at least 2 interfaces. In some instances, an injection has at least 1, 2, 3, 4, 5, 6, 7, 8, or more than 8 interfaces. In some instances, an injection has at least, at most, about, or within a range spanning 1, 2, 3, 4, 5, 6, 7, or 8 interfaces. In some instances, surfaces of an injector have an affinity for a continuous phase than a dispersed phase. For example, surfaces of an injector attract can have affinity for oil and repel an aqueous phase. In some instances, surfaces of an injector are at least one of hydrophobic or fluorophilic.

Figure 9:
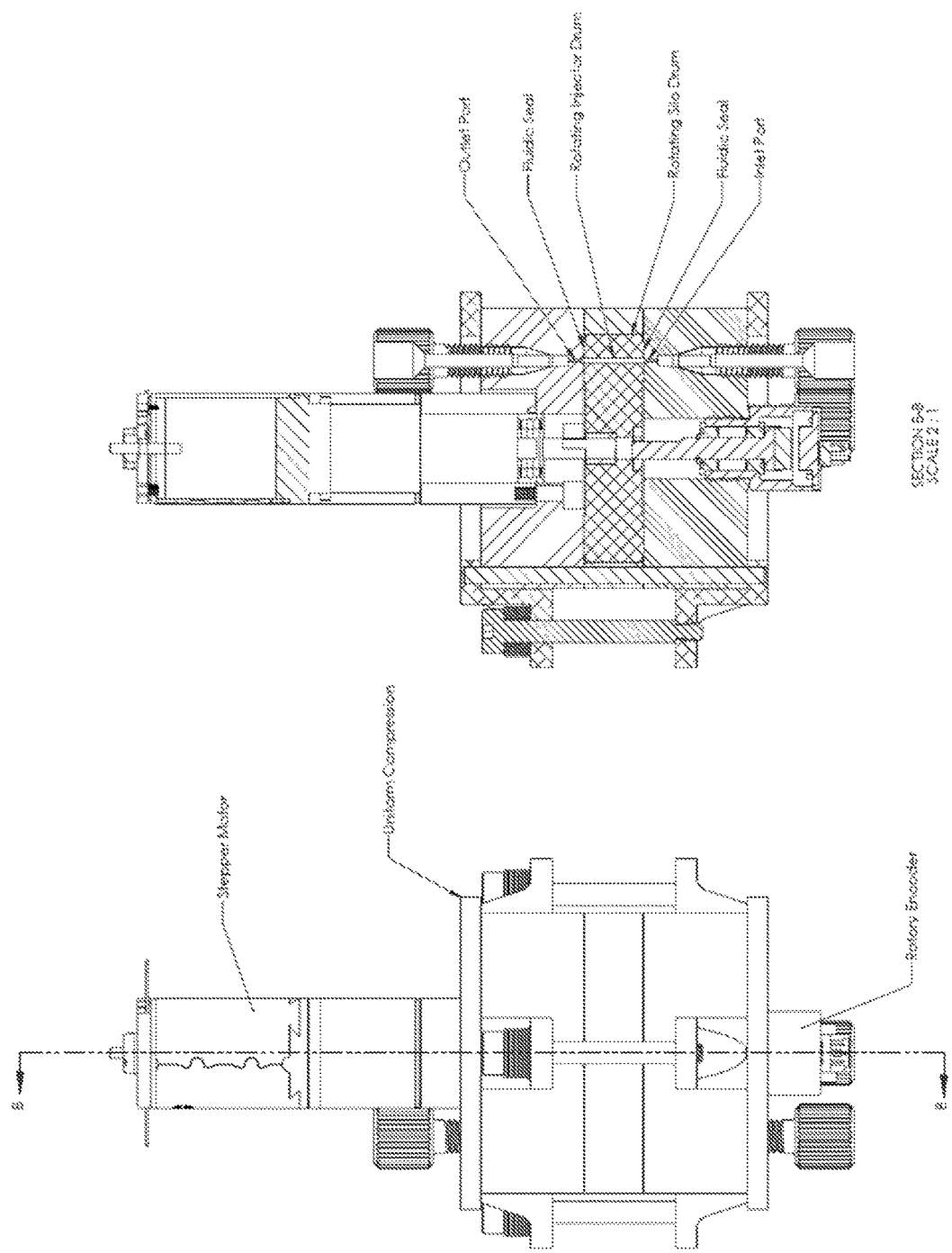
FIG. 9 depicts components of an injector.
Figure 10:
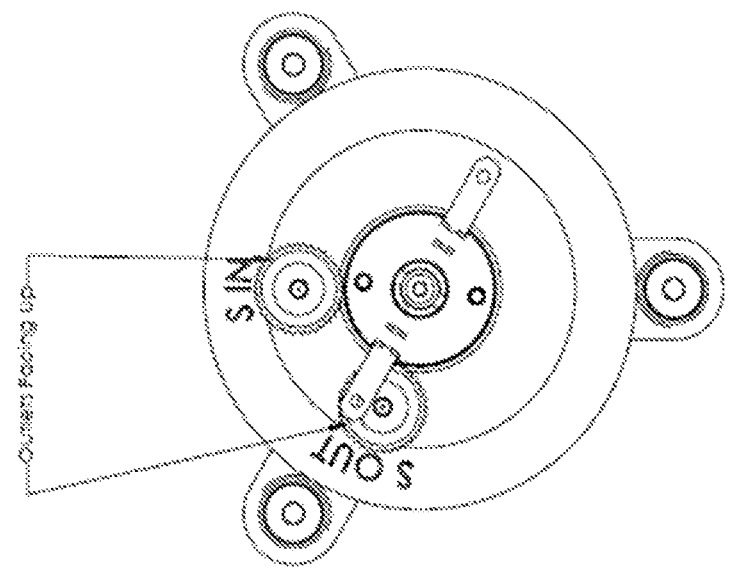
FIG. 10 depicts an arrangement of inlets and outlets of an injector.
Figure 10:
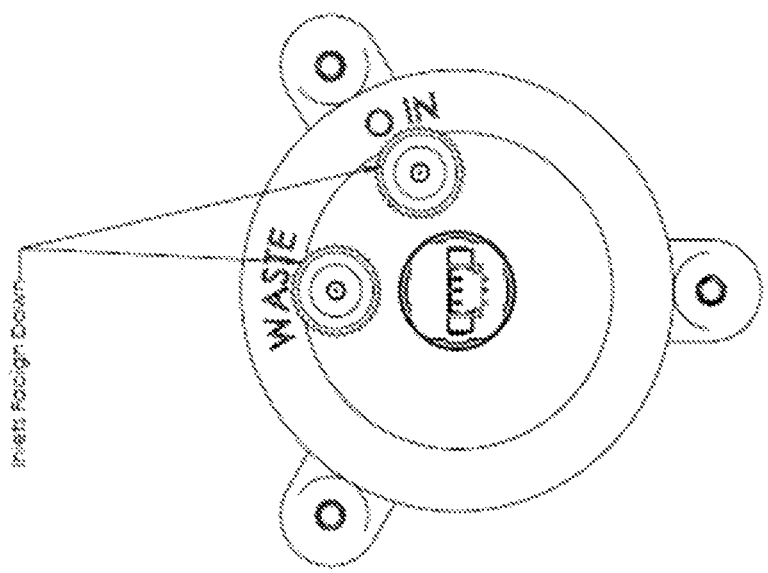
Figure 11:
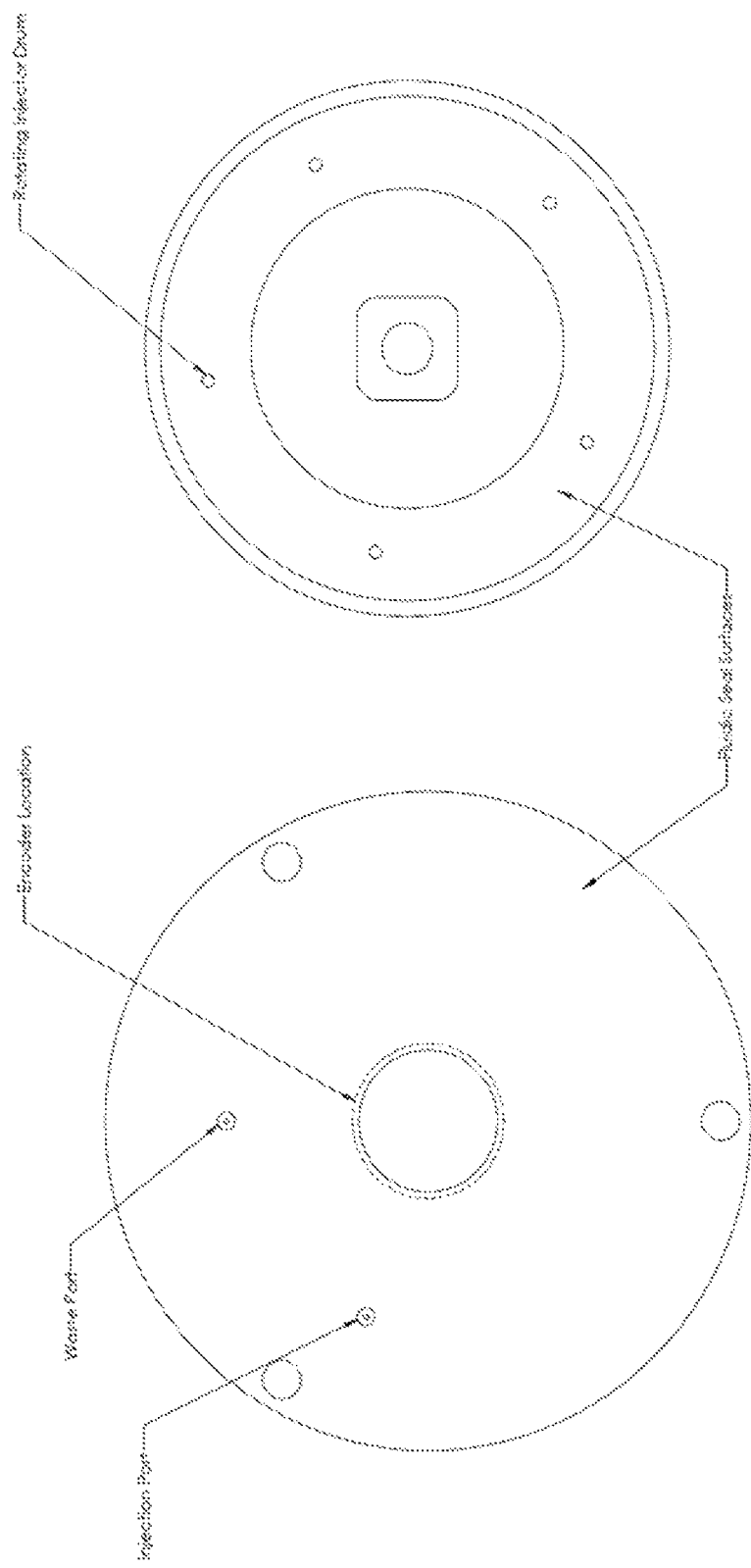
FIG. 11 depicts an arrangement of a cavity of an injector.
Figure 12:
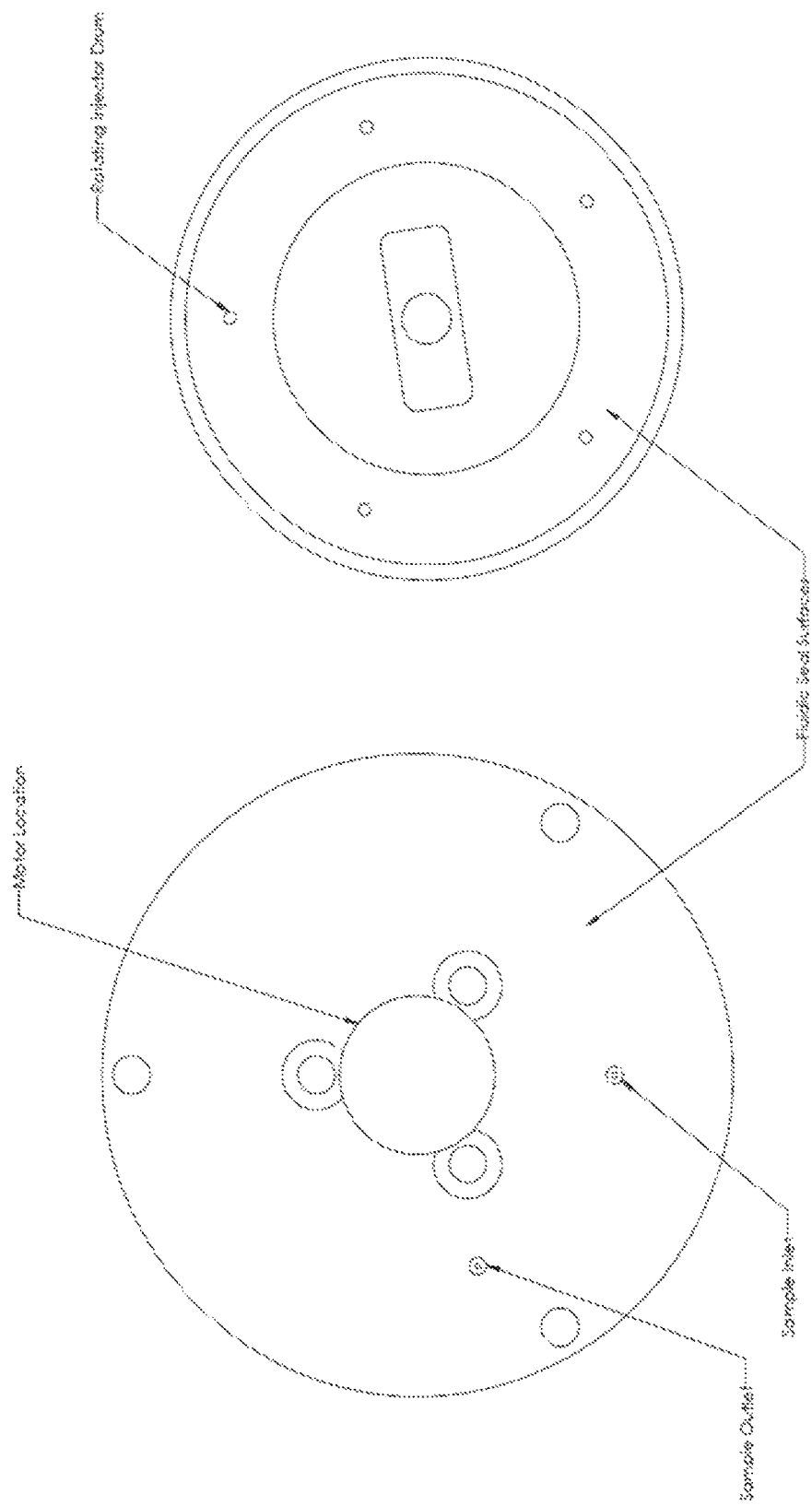
FIG. 12 depicts an alternate arrangement of a cavity of an injector.

FIG. 9 depicts components of an injector. FIG. 10 depicts an arrangement of inlets and outlets of an injector. FIG. 11 depicts an arrangement of a cavity of an injector. FIG. 12 depicts an alternate arrangement of a cavity of an injector.

Figure 13:
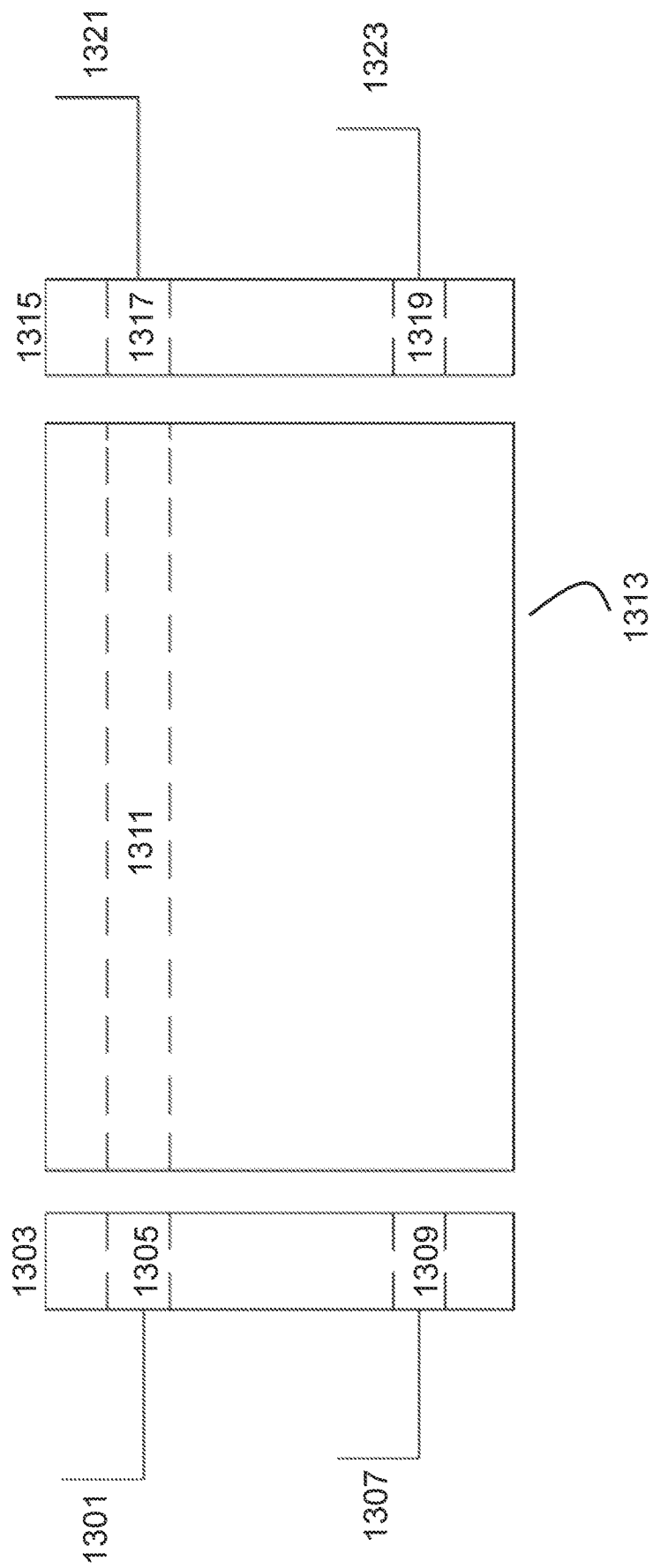
FIG. 13 depicts a cross section of a cylindrical drum comprising one channel.

In some cases, a sample enters an injector's rotating drum. A schematic cross sectional view of an exemplary cylindrical drum 1313 is depicted in FIG. 13. A cylindrical drum 1313 comprises end cap covers 1303, 1315 and an internal channel having a fixed internal volume 1311. Each cap cover 1303, 1315 comprises respective channels for fluid flow into or out of the fixed internal volume. Cap cover 1303 comprises channels 1305 and 1309, and cap cover 1315 comprises channels 1317 and 1319. In some embodiments, channel 1305 can be configured to be in alignment with inlet 1301 of the injector. In some embodiments, channel 1309 can be configured to be in alignment with inlet 1307 of the injector. The inlet channel 1301 can be connected to a supply of a dispersed phase. The inlet 1307 can be connected to a supply of a continuous phase. The channel 1317 can be configured to be in alignment with an outlet 1321 of the injector. The channel 1319 can be configured to be in alignment with an outlet 1323 of the injector. In some embodiments, all surfaces of the channels of the drum comprise a coating with affinity for the continuous phase. Sometimes all surfaces of the channels of the drum comprise a hydrophobic coating. In some embodiments, all surfaces of the channels of the drum comprise a hydrophilic coating.

Figure 14:
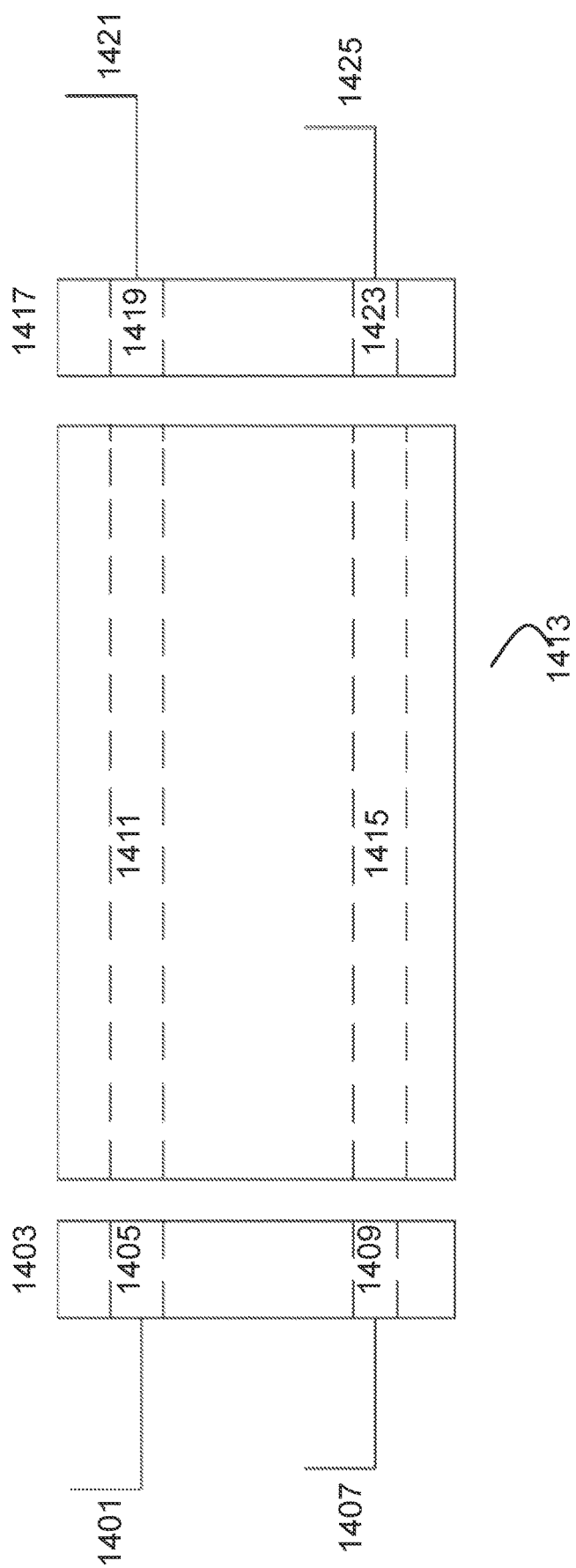
FIG. 14 depicts a cross section of a cylindrical drum comprising two channels.

A cross-sectional view of a second exemplary drum 1413, according to some embodiments, is depicted in FIG. 14. The cylindrical drum 1413 comprises end cap covers 1403, 1417, a first internal channel 1411 comprising a first fixed internal volume and a second internal channel 1415 comprising a second fixed internal volume. Each cap cover 1403, 1417 comprises channels for flowing fluid into or out of the internal channel 1411 or 1415. Channel 1405 can be configured to be aligned with a first inlet 1401 of the injector 1413. Channel 1409 can be configured to be aligned with a second inlet 1407 of the injector 1413. Channel 1419 can be configured to be aligned with a first outlet 1421 of the injector 1413. Channel 1423 can be configured to be aligned with a second outlet 1425 of the injector 1413. The first internal channel 1411 can be configured to be aligned with the channel 1405 and the channel 1421. The second internal channel 1411 can be configured to be aligned with the channel 1409 and the channel 1425. Use of two internal channels can enable filling of one channel while the other channel is emptied. For example, one of the first internal channel 1411 or second internal channel 1415 can be injected with a fluid while the other is purged. In some embodiments, all surfaces of the channels of the drum comprise a hydrophobic or fluorophilic coating. In some embodiments, all surfaces of the channels of the drum comprise a hydrophilic coating.

Figure 15:
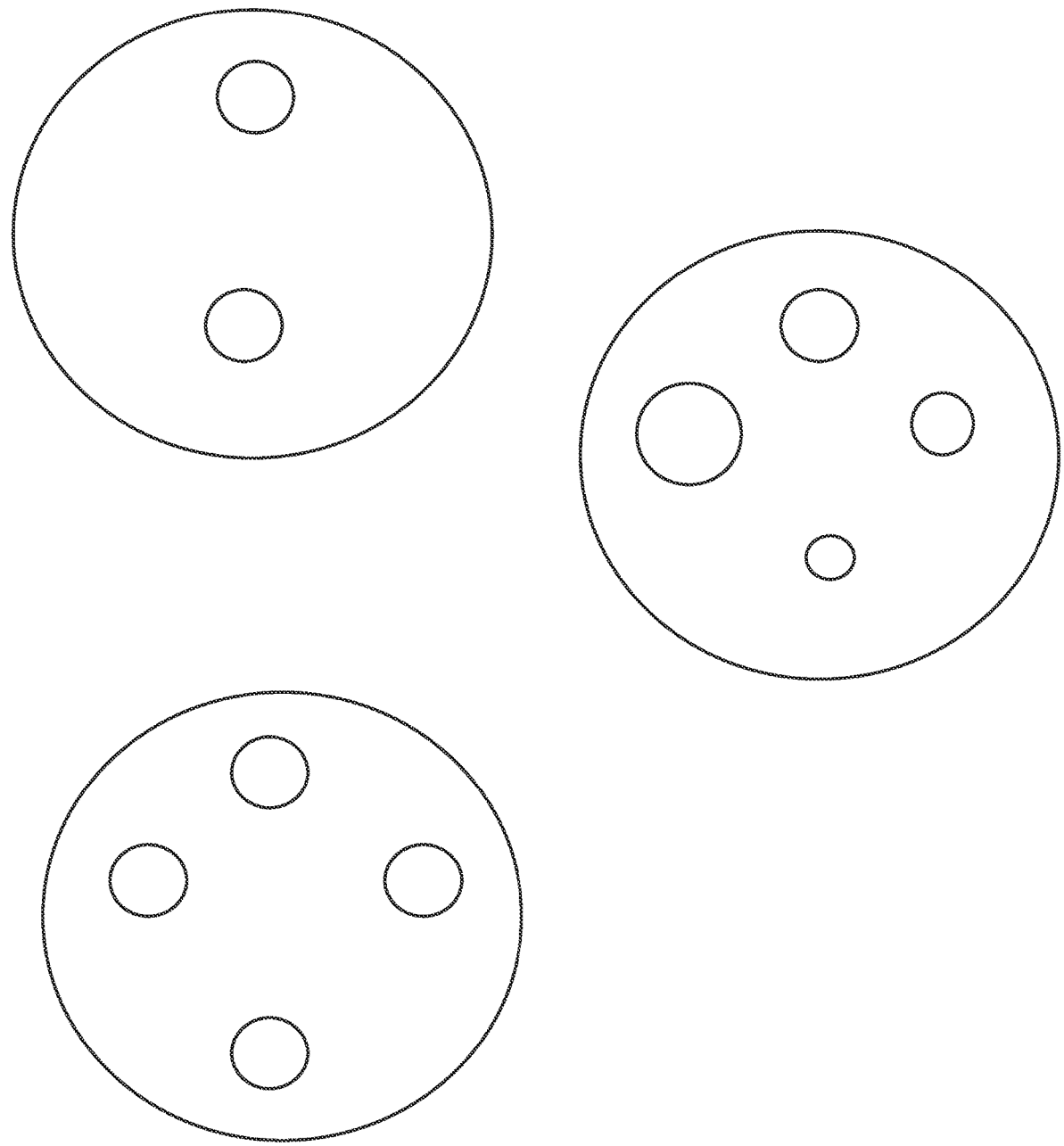
FIG. 15 depicts different arrangements of a cavity of an injector.

FIG. 15 depicts different arrangements of a cavity of an injector.

In some cases, a drum contains at least 1 fluid chamber, such as the internal channel with the fixed volume described herein. In some cases, a drum contains at least 1, 2, 3, 4, 5, 6, 7, 8, or more than 8 fluid chambers. In some cases, a drum contains at most, about, or within a range spanning 1, 2, 3, 4, 5, 6, 7, or 8 fluid chambers. Chamber volumes can range from about 1 microliter (µL) to about 50 µL. In some cases, chamber volume is at least about 1 µL, 5 µL, 10 µL, 15 µL, 20 µL, 25 µL, 30 µL, 35 µL, 40 µL, 50 µL, 75 µL, 100 µL, 250 µL, 500 µL, or more than 500 µL. In some cases, chamber volume is up to about 1 µL, 5 µL, 10 µL, 15 µL, 20 µL, 25 µL, 30 µL, 35 µL, 40 µL, 50 µL, 75 µL, 100 µL, 250 µL, 500 µL, or more than 500 µL. In some cases, chamber volume is about or within a range spanning 1 µL, 5 µL, 10 µL, 15 µL, 20 µL, 25 µL, 30 µL, 35 µL, 40 µL, 50 µL, 75 µL, 100 µL, 250 µL, or 500 µL. In some cases, chamber volume is at least 1 µL, 5 µL, 10 µL, 15 µL, 20 µL, 25 µL, 30 µL, 35 µL, 40 µL, 50 µL, 75 µL, 100 µL, 250 µL, 500 µL, or more than 500 µL. In some cases, chamber volume is at most 1 µL, 5 µL, 10 µL, 15 µL, 20 µL, 25 µL, 30 µL, 35 µL, 40 µL, 50 µL, 75 µL, 100 µL, 250 µL, 500 µL, or more than 500 µL. In some cases, chamber volume is at least, at most, about, or within a range spanning 0.01 picoliter (pL), 0.05 µL, 0.1 µL, 0.5 µL, 1 µL, 5 µL, 10 µL, 15 µL, 20 µL, 25 µL, 30 µL, 35 µL, 40 µL, 50 µL, 75 µL, 100 µL, 250 µL, 500 µL, 1000 µL, 0.01 nanoliter (nL), 0.05 nL, 0.1 nL, 0.5 nL, 1 nL, 5 nL, 10 nL, 15 nL, 20 nL, 25 nL, 30 nL, 35 nL, 40 nL, 50 nL, 75 nL, 100 nL, 250 nL, 500 nL, 1000 nL, 0.01 microliter (µL), 0.05 µL, 0.1 µL, 0.5 µL, 1 µL, 5 µL, 10 µL, 15 µL, 20 µL, 25 µL, 30 µL, 35 µL, 40 µL, 50 µL, 75 µL, 100 µL, 250 µL, 500 µL, 1000 µL, 1 milliliter (mL), 2 mL, 3 mL, 4 mL, 5 mL, 6 mL, 7 mL, 8 mL, 9 mL, or 10 mL. In some instances, a drum contains more than one chamber. In some embodiments, a drum comprises one chamber comprising a volume different from that of another chamber of the drum.

Often a proper position of a sample of nucleic acids and/or reagents in an injector drum is defined when a chamber of a drum is fully occupied by the sample of nucleic acids and/or reagents, where a sample has displaced continuous phase in a drum by overfilling a chamber of a drum with excess continuous phase and sample going to a waste stream. A volume of the sample in some cases is equal to a size of a chamber. This can automate sample handling.

Following a sample being in an injector drum, a drum is in some instances rotated and sample then passes through a downstream flow path to a coalescer. Rotation can occur by a motor. In some instances, rotation is performed using a solenoid with position switches. Sometimes a sample passes through a flow path to a coalescer using a sample injector pump. In some instances, sample not in a drum flows to a waste outlet. In some instances, sample not in a drum are in a fluid path and are loaded. Sometimes, sample not in a drum are in a fluid path and are not loaded.

Often a surface in contact with a sample that passes through a downstream path is primed with an immiscible fluid. In some cases, a surface is primed with an oil such as a fluorinated oil. In some cases, an oil prevents a target molecule in a sample from contacting a surface of an instrument.

In some instances, an injector allows for primers and probes to be selected. In some cases, primers and probes are pre-designed and pre-prepared and thus a user would not need to prepare reagents for an assay. In some instances, a system includes a selector valve connected to reservoirs of primers and probes. Reservoirs can be single-fill or refillable. In some instances, reservoirs can be disconnected.

Cassette

In addition to a sample, sometimes at least one reagent such as enzymes, dNTPs, primers, and probes are also needed for nucleic acid amplification, such as PCR. Sometimes a valve, such as a cassette, provides at least one reagent to systems described herein. In some instances, a cassette comprises at least one chamber that is pre-loaded with a set volume. In some cases, a cassette allows liquid to be stored and later be loaded. Often a cassette has at least two interfaces. In some instances, an injection valve has at least 1, 2, 3, 4, 5, 6, 7, 8, or more than 8 interfaces. In some instances, an injection valve has about, at most, or within a range spanning 1, 2, 3, 4, 5, 6, 7, or 8 interfaces. In some instances, a cassette contains 1 flow path. For example, a cassette with one flow path allows liquid to be loaded and unloaded in 1 flow path. In some instances, a cassette valve has at least 1, 2, 3, 4, 5, 6, 7, 8, or more than 8 flow paths. In some instances, a cassette valve has about, at most, or within a range spanning 1, 2, 3, 4, 5, 6, 7, or 8 flow paths. In some instances, multiple flow paths are used at the same time.

In some cases, a cassette contains a drum. A drum for example has at least 1 fluid chamber. Chamber volumes can range from about 1 µL to about 50 µL. Chamber volumes of some embodiments range from about 0.05 picoliter (µL) to about 5 milliliter (mL). In some cases, chamber volume is at least about 0.5 µL, 1 µL, 5 µL, 10 µL, 15 µL, 20 µL, 25 µL, 30 µL, 35 µL, 40 µL, 50 µL, 75 µL, 100 µL, 250 µL, or 500

μL. In some cases, chamber volume is up to about 0.5 μL, 1 μL, 5 μL, 10 μL, 15 μL, 20 μL, 25 μL, 30 μL, 35 μL, 40 μL, 50 μL, 75 μL, 100 μL, 250 μL, 500 μL, or more about 500 μL. In some cases, chamber volume is at least 0.5 μL, 1 μL, 5 μL, 10 μL, 15 μL, 20 μL, 25 μL, 30 μL, 35 μL, 40 μL, 50 μL, 75 μL, 100 μL, 250 μL, or 500 μL. In some cases, chamber volume is up to 0.5 μL, 1 μL, 5 μL, 10 μL, 15 μL, 20 μL, 25 μL, 30 μL, 35 μL, 40 μL, 50 μL, 75 μL, 100 μL, 250 μL, 500 μL, or more about 500 μL. In some cases, chamber volume is about or within a range spanning 0.5 μL, 1 μL, 5 μL, 10 μL, 15 μL, 20 μL, 25 μL, 30 μL, 35 μL, 40 μL, 50 μL, 75 μL, 100 μL, 250 μL, or 500 μL. In some cases, chamber volume is at least, at most, about, or within a range spanning 0.01 picoliter (pL), 0.05 pL, 0.1 pL, 0.5 pL, 1 pL, 5 pL, 10 pL, 15 pL, 20 pL, 25 pL, 30 pL, 35 pL, 40 pL, 50 pL, 75 pL, 100 pL, 250 pL, 500 pL, 1000 pL, 0.01 nanoliter (nL), 0.05 nL, 0.1 nL, 0.5 nL, 1 nL, 5 nL, 10 nL, 15 nL, 20 nL, 25 nL, 30 nL, 35 nL, 40 nL, 50 nL, 75 nL, 100 nL, 250 nL, 500 nL, 1000 nL, 0.01 microliter (μL), 0.05 μL, 0.1 μL, 0.5 μL, 1 μL, 5 μL, 10 μL, 15 μL, 20 μL, 25 μL, 30 μL, 35 μL, 40 μL, 50 μL, 75 μL, 100 μL, 250 μL, 500 μL, 1000 μL, 1 milliliter (mL), 2 mL, 3 mL, 4 mL, 5 mL, 6 mL, 7 mL, 8 mL, 9 mL, or 10 mL. In some instances, there are at least two chambers having different volumes.

Surfaces of a cassette are often at least one of hydrophobic and fluorophilic. In some cases, fluid passes through a cassette using a fluid introduction pump. In some instances, fluid loaded or stored in a cassette is brought into position within a valve when there is a measured amount of fluid. In some instances, a cassette is brought into position within a valve by monitoring a location of fluid within a valve. Fluid is often introduced into a cassette until a specified volume is contained in a drum of a cassette. In some cases, a second fluid is introduced into a second channel of a drum. In some cases, a drum contains at least 1, 2, 3, 4, 5, 6, 7, 8 or more than 8 fluid channels. In some cases, a drum contains at most, about, or within a range spanning 1, 2, 3, 4, 5, 6, 7, or 8 fluid channels.

In some instances, a cassette contains a reservoir for reagents. For example, a reservoir contains nucleic acid amplification reagents. In some cases, a reservoir is refillable. In some cases, reagents from a reservoir pass through a zero-dead volume valve.

Figure 16:
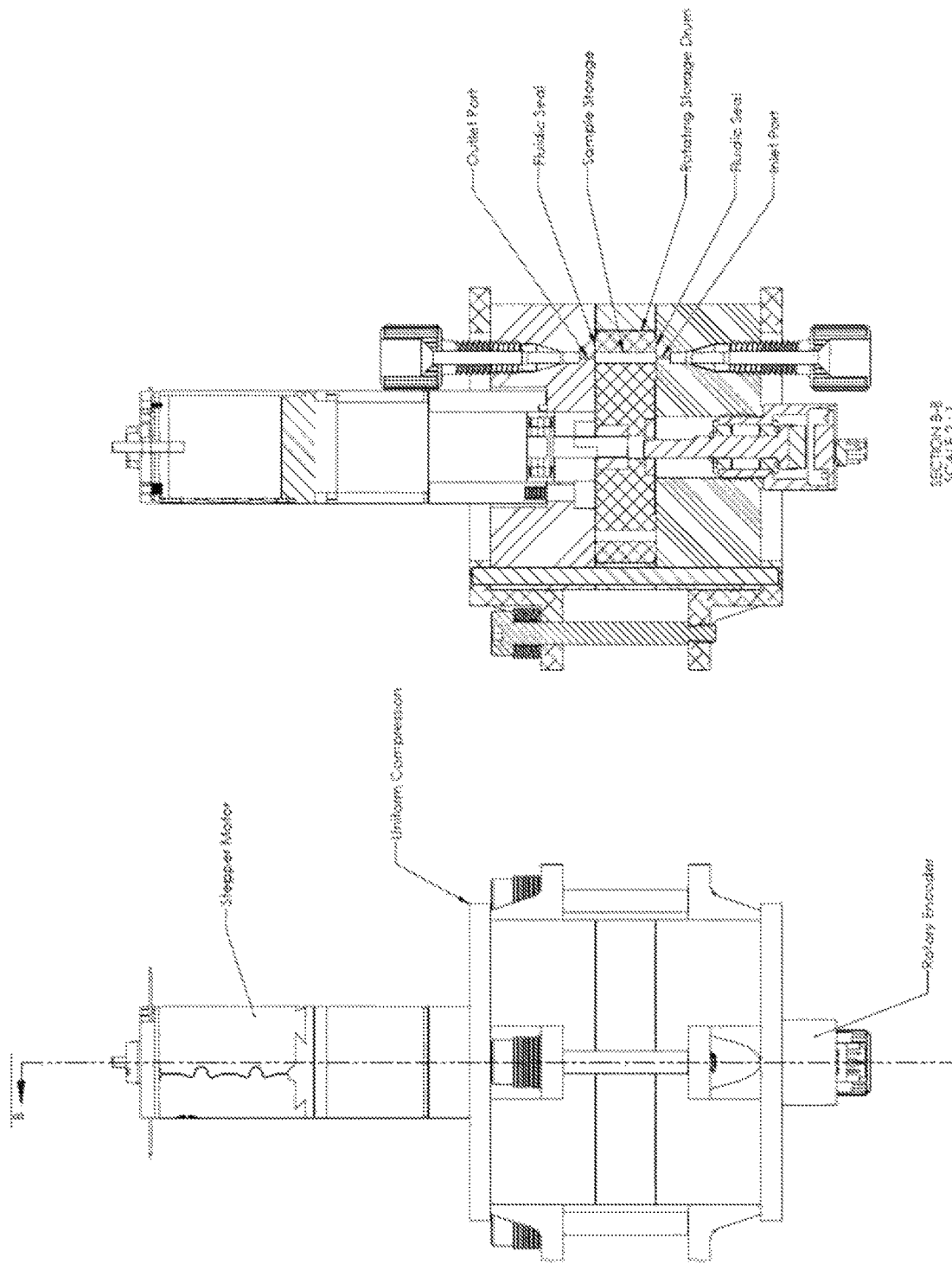
FIG. 16 depicts components of a cassette.
Figure 17:
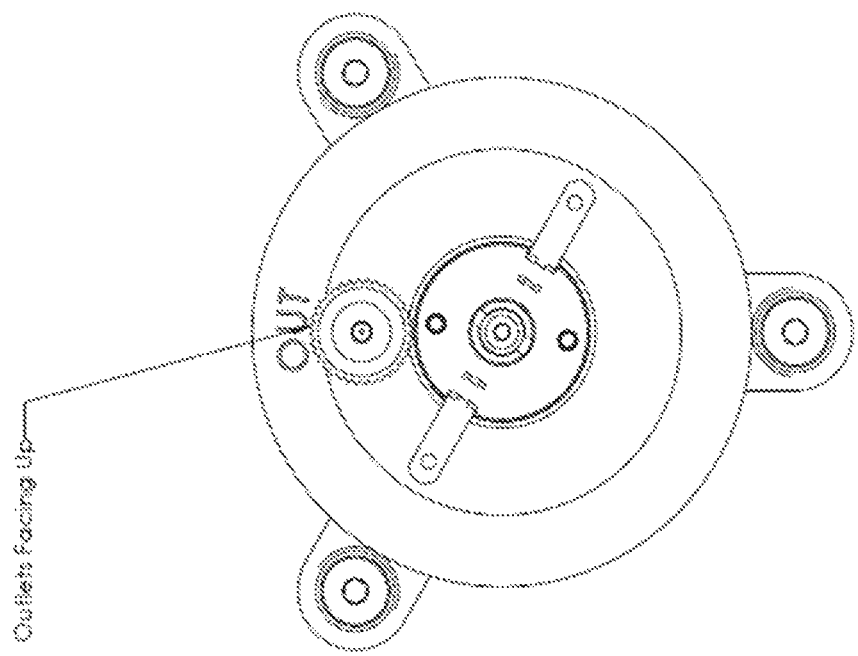
FIG. 17 depicts an arrangement of an inlet and outlet of a cassette.
Figure 17:
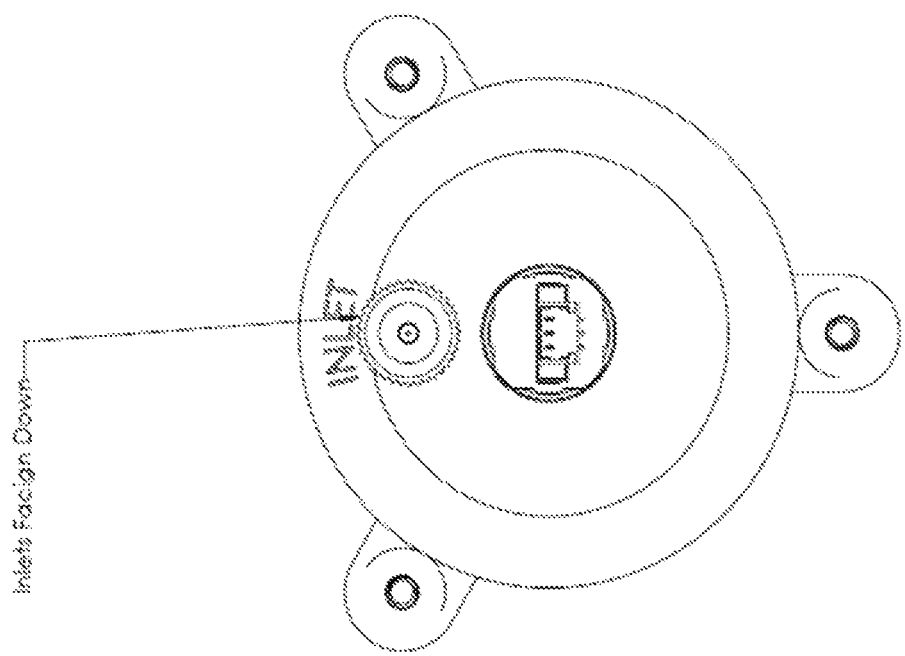
Figure 18:
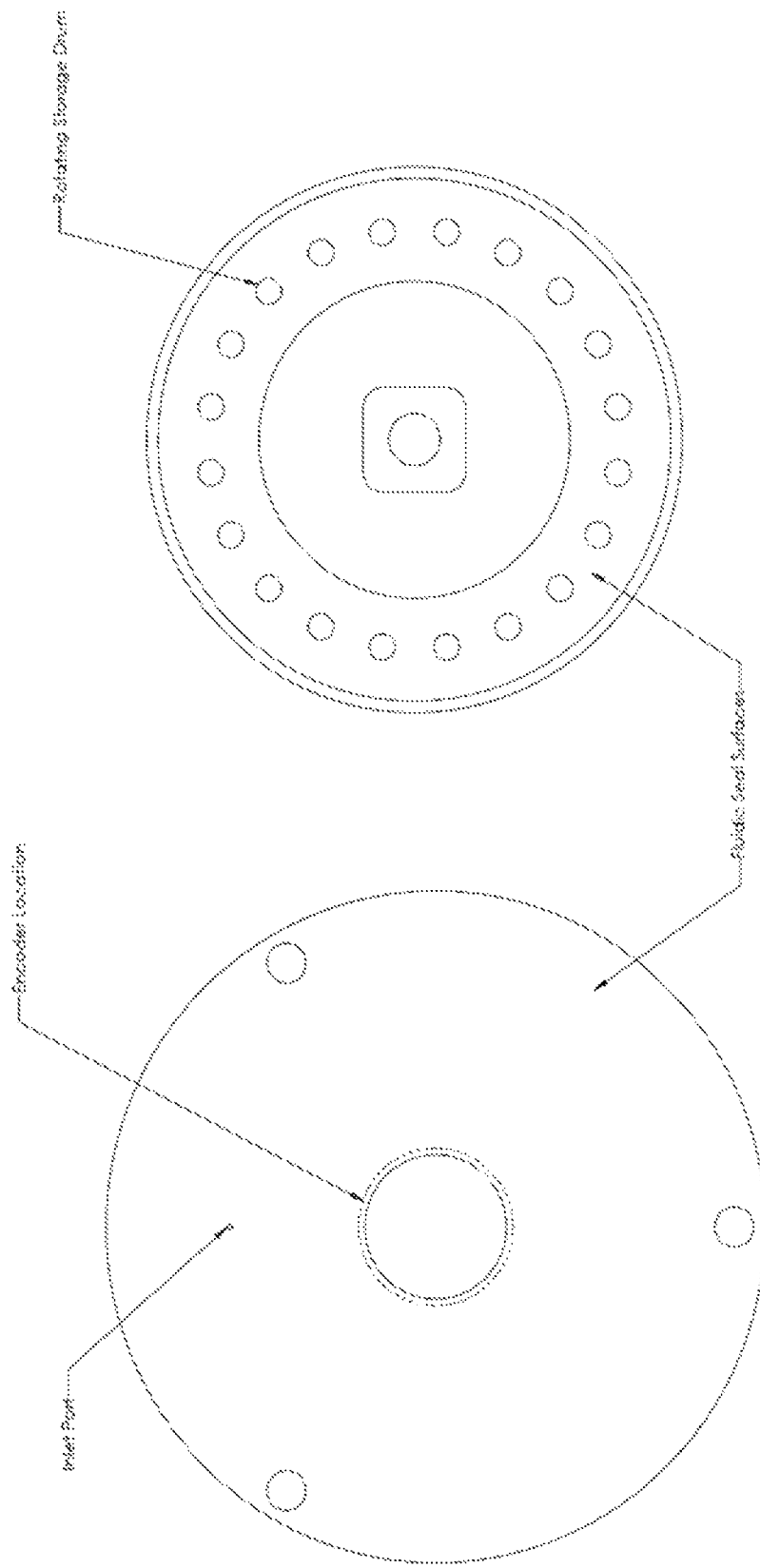
FIG. 18 depicts an arrangement of a cavity of a cassette.
Figure 19:
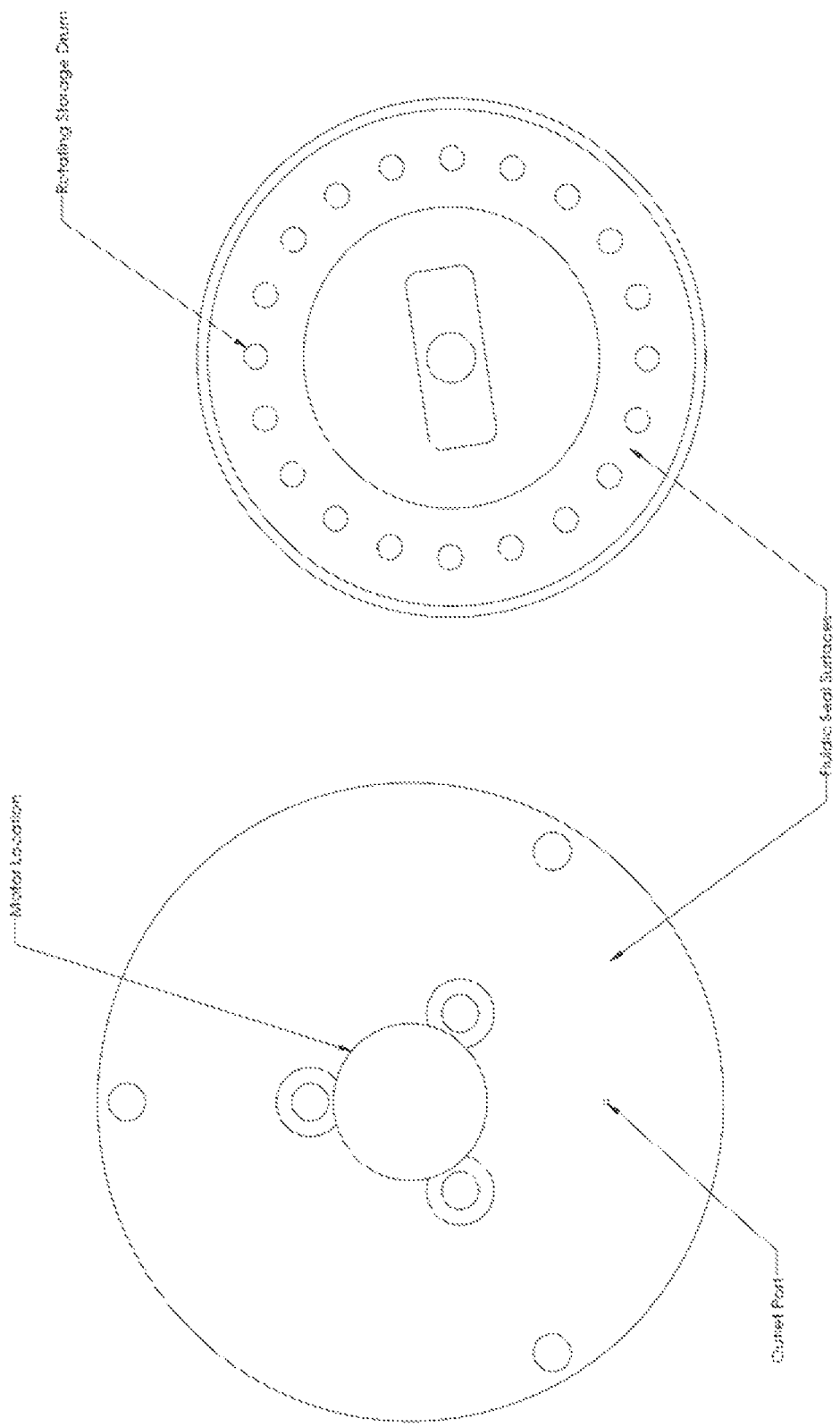
FIG. 19 depicts an alternate arrangement of a cavity of a cassette.

FIG. 16 depicts components of a cassette. FIG. 17 depicts an arrangement of an inlet and outlet of a cassette. FIG. 18 depicts an arrangement of a cavity of a cassette. FIG. 19 depicts an alternate arrangement of a cavity of a cassette.

Gravity-Trap Coalescer

In some embodiments, the gravity trap coalescer can be configured to coalesce two or more dispersed phases. In some embodiments, the gravity trap coalescer can be configured to coalesce a first dispersed phase and a second dispersed phase. For example, an emulsion comprises a first dispersed phase comprising droplets in a first continuous phase and a second dispersed phase comprising at least one droplet in a second continuous phase. The gravity trap coalescer can be configured to combine a droplet of the first dispersed phase with a droplet of the second dispersed phase to form a third droplet such that the third droplet can be further processed by one or more components of a system as described herein as a single entity, rather than as multiple dispersed entities. In some embodiments, the gravity trap coalescer can be configured to generate the third droplet in a third continuous phase. In some embodiments, the first continuous phase, the second continuous phase and the third continuous phase have the same composition. For example, the first continuous phase, the second continuous phase and the third continuous phase can comprise one or more oils and/or one or more surfactants.

In some embodiments, a droplet of a first dispersed phase comprising a reagent is combined with a droplet of a second dispersed phase comprising a target molecule (e.g. DNA or RNA) to generate a third droplet of a third dispersed phase comprising both the reagent and the target molecule. Reagents can be at least one of primers, probes, transcriptase, buffers, and dNTPs. In some instances, an amount of reagent can be determined. For example, the quantity of reagents in a droplet of the first dispersed phase can be selected based on the type and/or quantity of target molecules in a droplet of the second dispersed phase such that the droplet formed by merging the droplets of the first and second dispersed phases can contain a quantity of the reagents and target molecules suited for a desired chemical reaction there between.

As described herein, a dispersed phase can be aqueous. In some instances, a dispersed phase comprises more than about 51% (by mass or by molar concentration) of water. In some instances, a continuous phase is immiscible or substantially immiscible with the dispersed phase. For example, the continuous phase can be hydrophobic, for example comprising an oil, such as a fluorinated oil. Sometimes a reagent and/or target molecule is encapsulated in droplets of dispersed phases. In some cases, a dispersed phase is coated with a surfactant. Sometimes a surfactant is delivered by a continuous phase in an injector. A surfactant can stabilize a dispersed phase within a continuous phase and/or prevent cross-contamination between the dispersed phase and the continuous phase. Alternately or in combination, a dispersed phase is hydrophobic and a continuous phase is hydrophilic. For example, the dispersed phase may comprise an oil, such as a fluorinated oil, and the continuous phase may be aqueous.

Exemplary fluorinated oils that may be suitable are sold under the trade name Fluorinert™ (3M), including, in particular, Fluorinert™ Electronic Liquid FC-3283, FC-40, FC-43, and FC-70. Another example of an appropriate fluorinated oil is sold under the trade name Novec™ (3M), including Novec™ HFE 7500 Engineered Fluid, which is 3-ethoxy-1,1,1,2,3,4,4,5,5,6,6,6-dodecafluoro-2-trifluoromethyl-hexane. In some cases, the fluorine-containing compound is $CF_3CF_2CF_2CH_3$, sold as Novec™ HFE 7000. In some cases, the fluorine-containing compound is 2,2,3,3,4,4,4-heptafluoro-1-butanol, $CF_3CF_2CF_2CH_2OH$. In some cases, the fluorinated oil is perfluorocarbon, such as perfluorooctane or perfluorohexane. In some cases, the fluorine-containing compound is a partially fluorinated hydrocarbon, such as 1,1,1-trifluorooctane or 1,1,1,2,2-petantafluorodecane.

In some cases, a droplet from a first dispersed phase containing a first target molecule is merged with a droplet from a second dispersed phase containing a second target molecule. Sometimes a sample comprises nucleic acids from at least two dispersed phases. In an example where a first dispersed phase of target molecules is merged with a second dispersed phase of target molecules, each dispersed phase of target molecules can be identified. For example, a sequence of nucleotides is ligated onto target molecules of a dispersed phase, where the sequence can include a number of nucleotides providing specificity sufficient to identify the source of the target molecules (e.g., a barcode). Sometimes target molecules are then sequenced, and the source of the target molecules can be identified based on the sequence of nucleotides.

In some cases, a concentration such as mass or molar concentration of nucleic acids is determined. Sometimes concentration is used to evaluate whether to sequence a target molecule or not. Concentration in some cases is adjusted through dilution. For example, water is used for dilution. Alternately or in combination, a reagent is diluted. In some instances, a concentration is determined to evaluate its suitability for nucleic acid sequencing.

Figure 20:
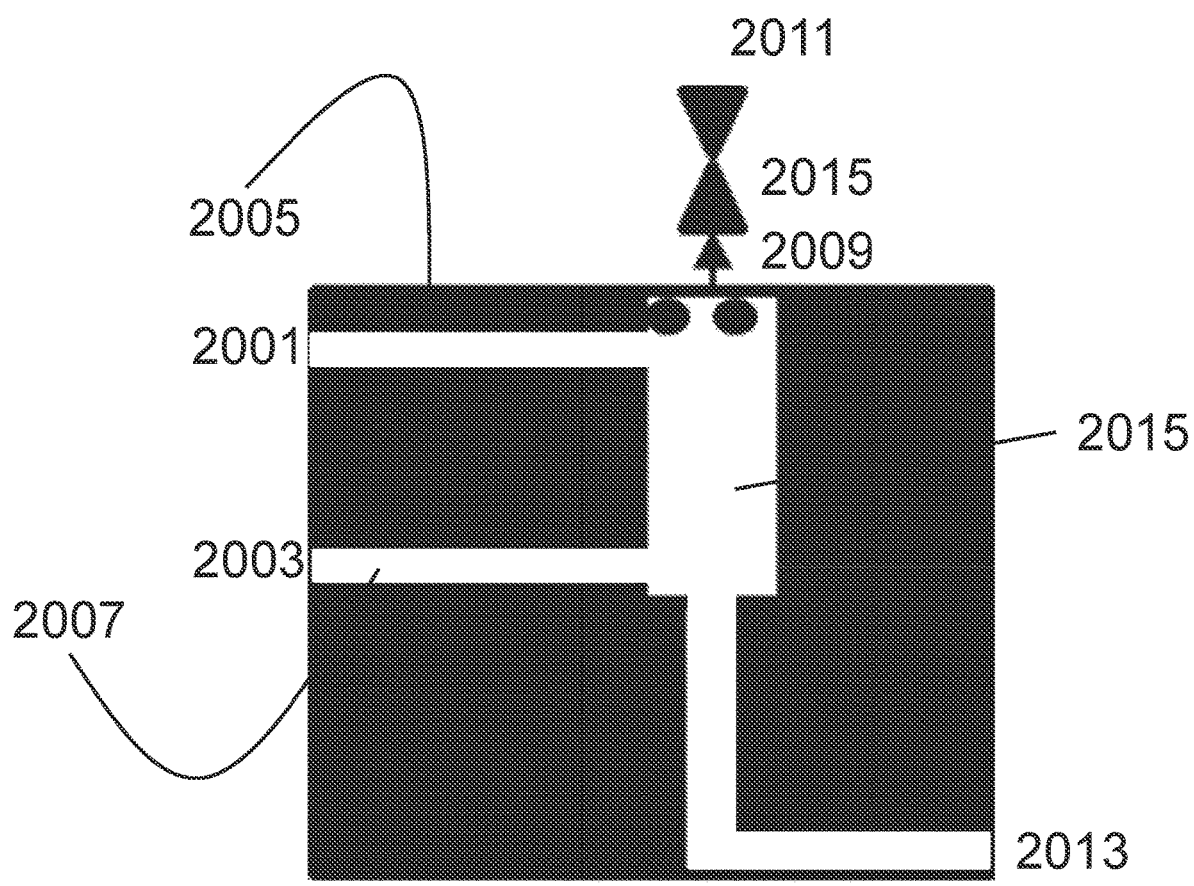
FIG. 20 depicts a coalescer arrangement with independent inlets.

An exemplary operation of a system as described herein is shown in FIG. 20. In a loading state, an inlet 2001, 2003 of a junction comprises a dispersed phase. A dispersed phase travels in a direction of a junction 2017. A removable restriction in a junction outlet is in a "closed" state if 2015 is closed, and a junction outlet is in an "open" state if 2015 is opened. Junction outlets 2013 comprise a continuous phase. No external source is provided at a junction outlet. In a "loaded" state, at least two dispersed phases are located in a junction outlet where they are trapped by gravitational forces 2009. Often at a first outlet of a junction, at least two portions of a dispersed phase have not been combined.

Figure 21:
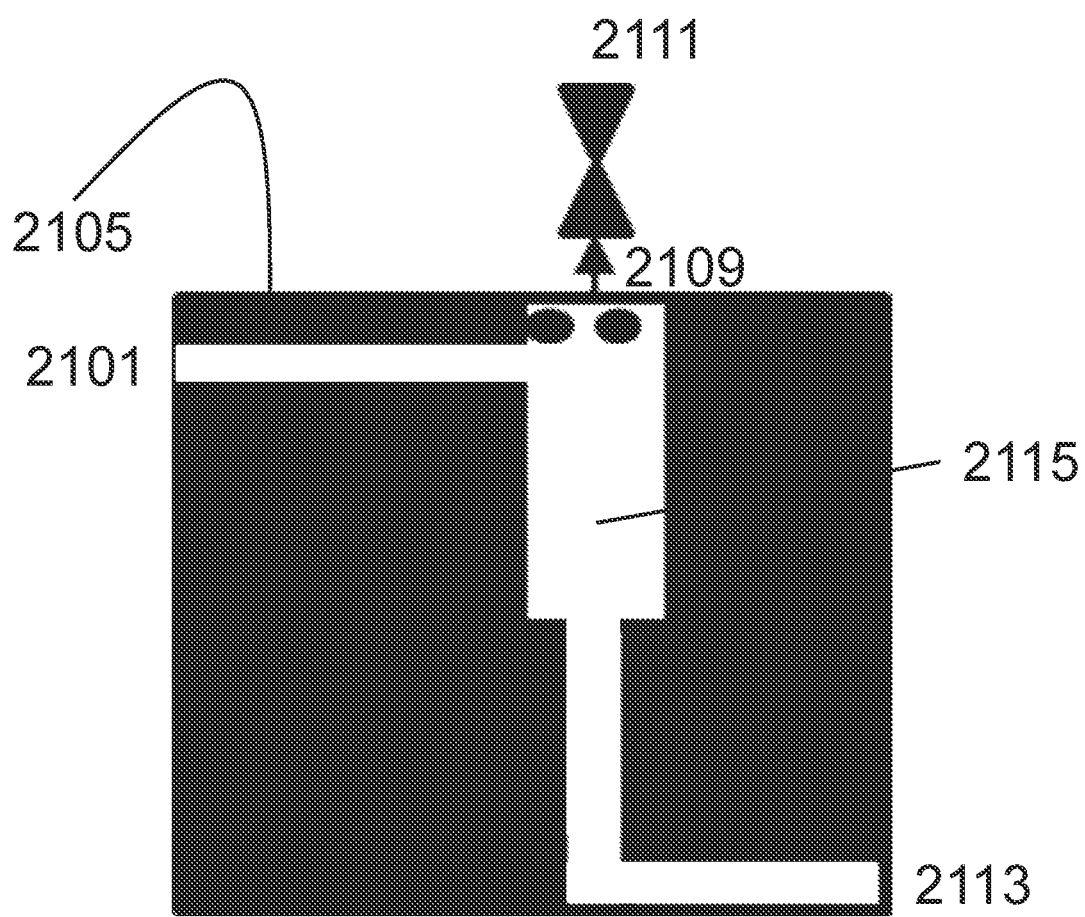
FIG. 21 depicts a coalescer arrangement with common inlets

Referring to FIG. 21, a first and second junction comprises only one inlet. In some instances, a junction comprises at least 1, 2, 3, 4, 5, 6, 7, 8, or more than 8 inlets. In some instances, a second junction comprises up to about 1, 2, 3, 4, 5, 6, 7, 8, or more than 8 inlets. In some instances, a junction comprises at most, about, or within a range spanning 1, 2, 3, 4, 5, 6, 7, or 8 inlets. Junction inlets are sometimes oriented horizontally, such that an axis of an inlet perpendicular to the cross section of an inlet is at an angle of greater than about 750 to an axis parallel to the direction of the local gravitational field. In some cases, a horizontally oriented axis is oriented such that it is normal to an axis of a first junction outlet perpendicular to a cross section of a second junction outlet. In such case, a propensity of a dispersed phase to move toward an outlet of a junction is increased. Sometimes a first junction inlet and a second junction inlet are horizontally opposed, such that central axes of horizontal components of the inlets are at an angle not less than 160° relative to each other. In such a case, an opposing flow of a continuous phase in an inlet will slow portions of a dispersed phase entering and increase the propensity that a portion of a dispersed phase will move toward a junction outlet.

Figure 22:
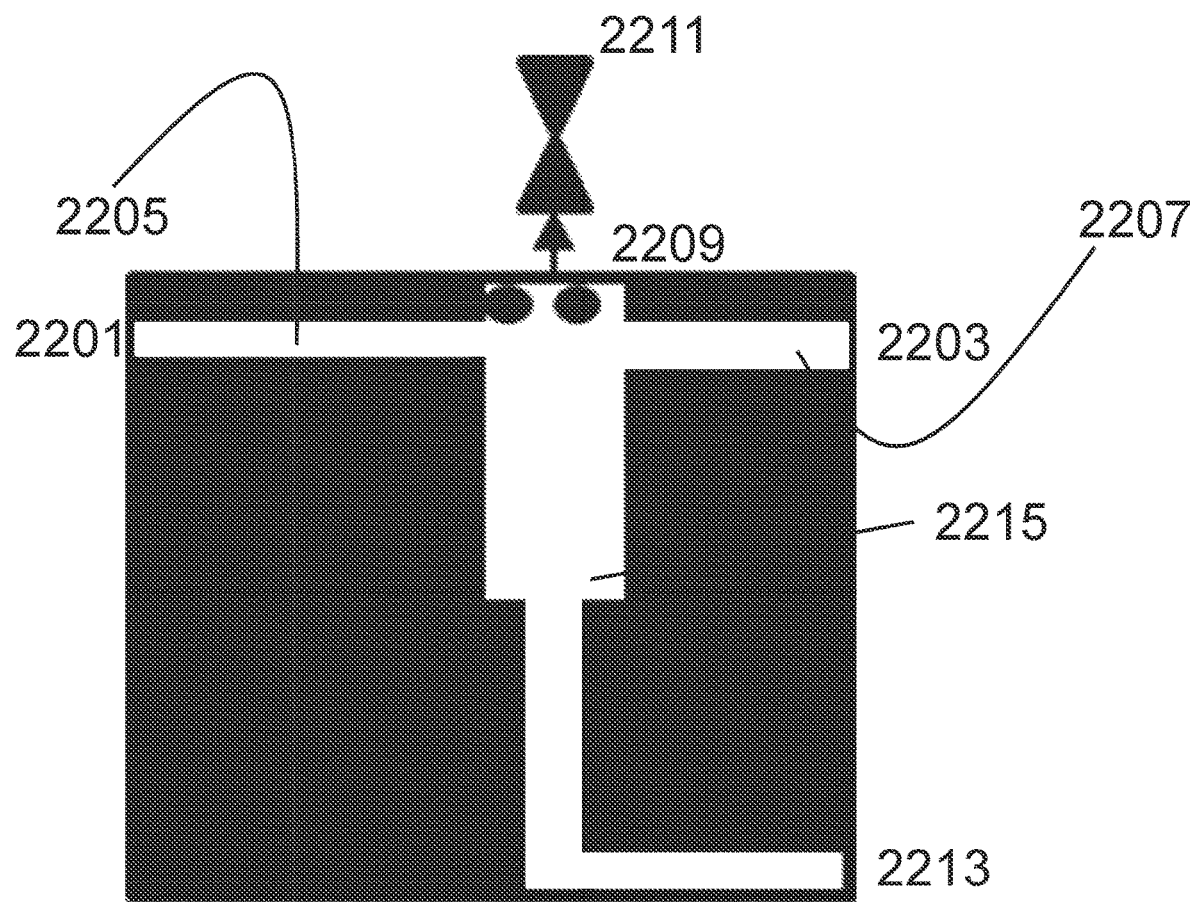
FIG. 22 depicts a coalescer arrangement with independent inlets of a same height.

As seen in FIG. 22, junction inlets 2201, 2203 join at a termination point and form a channel 2205, 2207 connected to outlet junctions 2215. In some instances, a junction inlet connects at least one point with an outlet. In some cases, a junction inlet connects at multiple points with an outlet. In some instances, a common channel is formed before joining outlet junctions. Referring to FIG. 22, outlets of a junction connect with junction inlets 2201, 2203 at separate points. This can ensure a dispersed phase is trapped in a junction outlet. As seen in FIG. 22, a junction inlet 2201, 2203 and a junction outlet 2211 connect and form a common channel.

Figure 23:
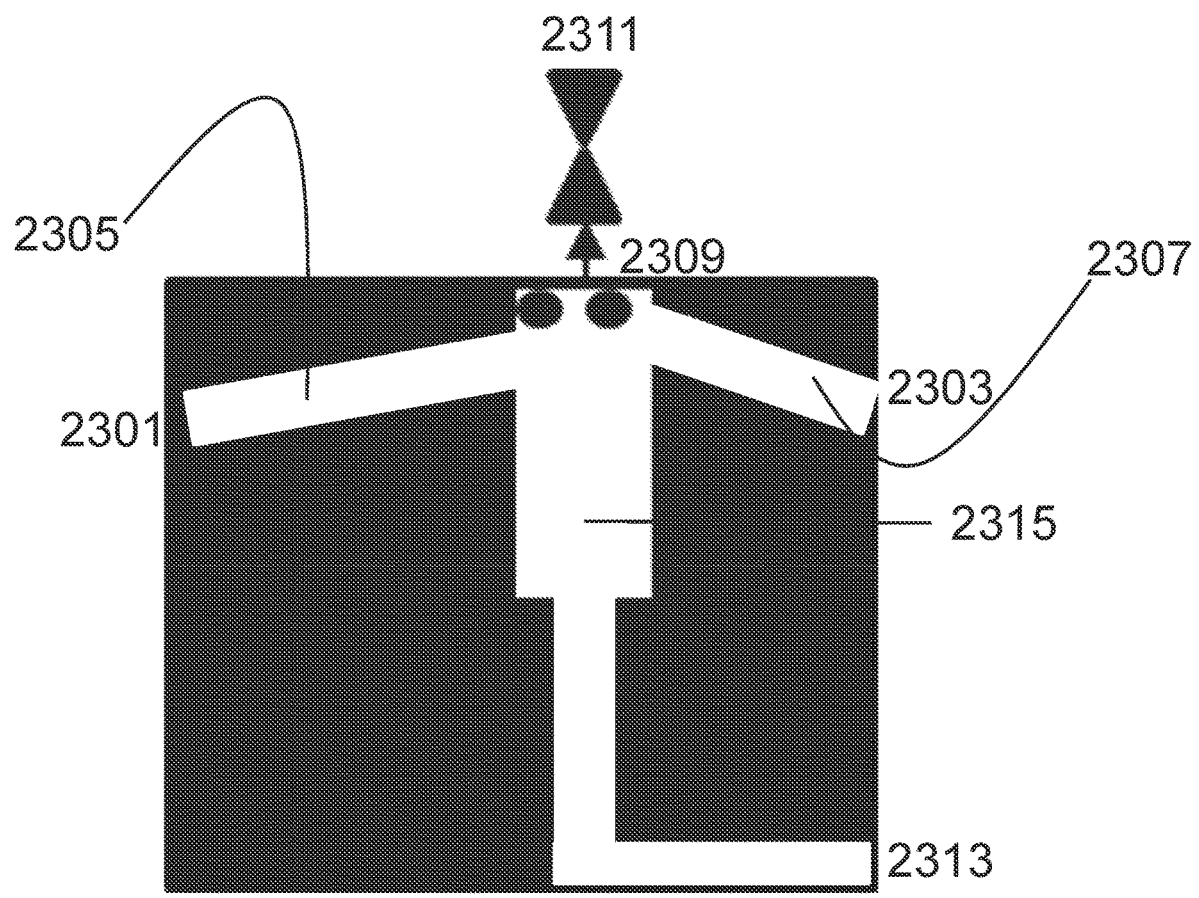
FIG. 23 depicts a coalescer arrangement with independent inlets and gravity assisted collection.

Referring to FIG. 23, an outlet has a length of a channel such that a dispersed phase does not flow to a point in a second direction of a vertical channel where a channel deviates from a vertical direction. As seen in FIG. 23, part of a channel comprising an inlet 2301, 2303 is oriented such that a central axis of an inlet 2301, 2303 deviates from a central axis of a channel 2315 by an angle less than 45°. This can allow a dispersed phase to have a vertical velocity when entering a junction aligned with a direction of its relative velocity to a continuous phase. For example, for a dispersed phase having a lower mass density than a continuous phase, the vertical velocity is in a direction of decreasing gravitational field strength. Whereas a dispersed phase has a higher mass density than a continuous phase, a vertical velocity can be in a direction of increasing gravitational field strength. In some instances, a deviation is less than 20°.

Referring to FIG. 23, inlets of a junction are vertically oriented, such that the axis perpendicular to a cross second of an inlet is oriented at an angle with an axis parallel to the direction of a gravitational field is at most about 45°. In some instances, an angle is at most about 20°. A vertical orientation is directed relative to a direction of decreasing field can increase a propensity of a dispersed phase to move toward a junction outlet. When a mass density of a dispersed phase is less than that of a continuous phase, a vertical orientation can be directed so as to make a small angle in the direction of decreasing gravitational field. When a mass density of a dispersed phase is greater than that of a continuous phase, a vertical orientation can be directed so as to make a small angle in a direction of increasing gravitational field.

Figure 24:
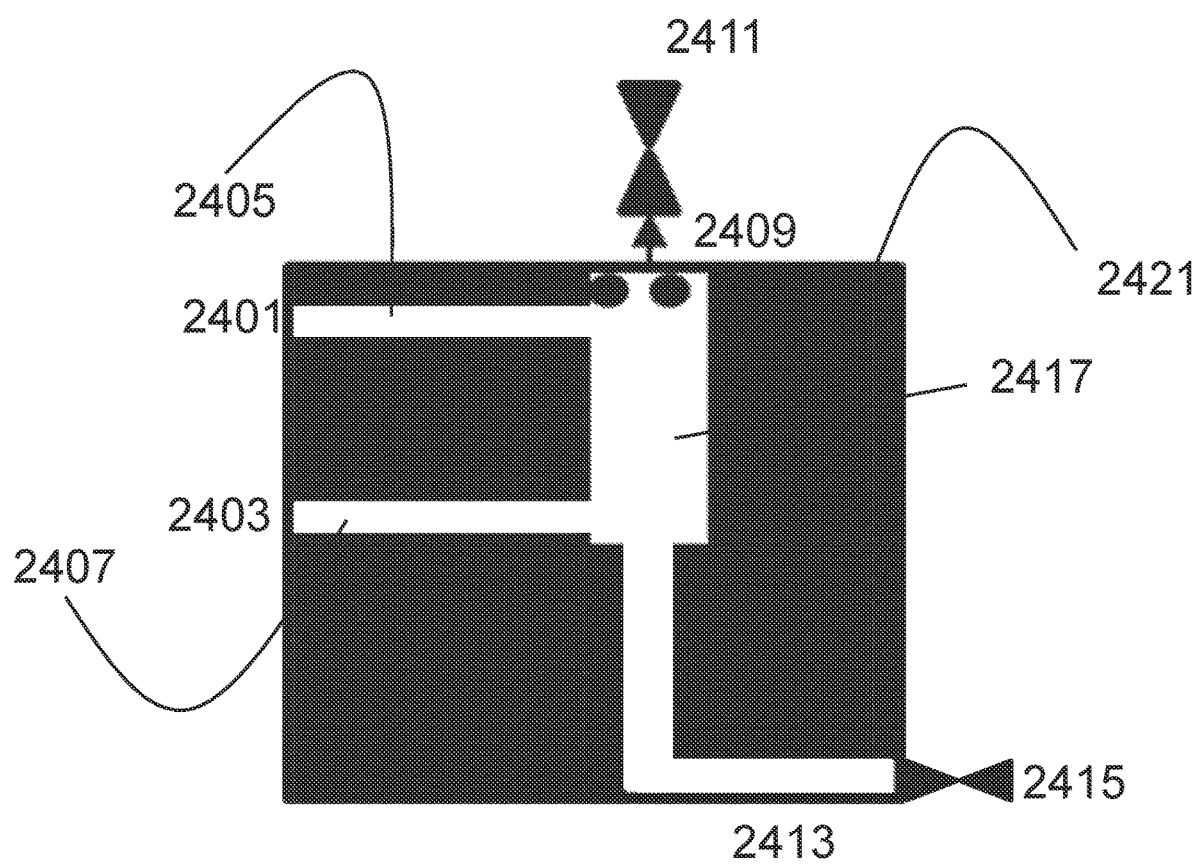
FIG. 24 depicts a coalescer arrangement with a valve on a continuous phase outlet.

Referring to FIG. 24, a valve 2415 in the flexible polymer tubing can provide a removable restriction required for a junction outlet. A junction outlet follows a path 2413 coaxial with a first axis of a monolith 2421. In some instances, junction outlet does not penetrate the lower plane of a monolith. Sometimes, a junction outlet deviates from a coaxial direction and penetrates a cylindrical side plane of the monolith. In some instances, an outlet of a junction continues through the lower plane of the monolith. In some cases, an outlet continues beyond a plane of a monolith by a channel fitted with a leak-resistant seal to monolith.

Figure 25:
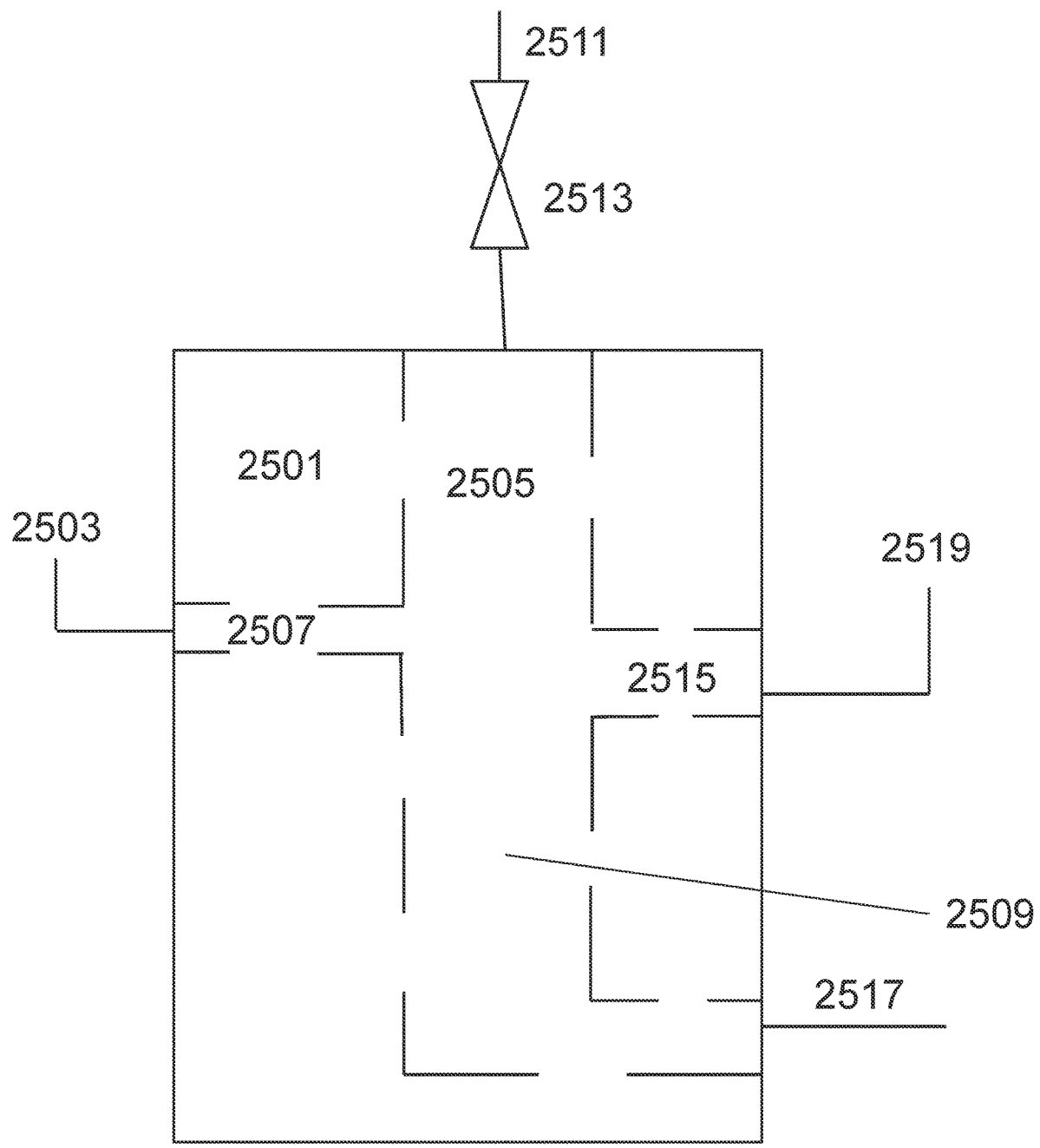
FIG. 25 depicts a cross section of a gravity-trap coalescer.

FIG. 25 depicts a schematic cross-sectional view of a gravity-trap coalescer, according to some embodiments. FIG. 25 illustrates an exemplary workflow of detection and quantification of at least one target molecule using gravity-trap coalescer as described herein. A first portion of a dispersed phase is introduced into the device at point 2503 where it flows through a first flow channel 2507. A second portion of a dispersed phase is introduced into the device at point 2519 where it flows through a second flow channel 2515. A first flow channel and a second flow channel meet at a junction 2505, and are referred to as a first inlet and a second inlet to the junction. A junction has a first outlet and a second outlet through which the continuous and dispersed phases can exit the junction. A first outlet and a second outlet share a central axis perpendicular to the cross section of the channel comprising the first outlet and the second outlet. A flow path for a fluid has a vertical or near-vertical segment (referred to as a "vertical channel"). For a first outlet, flow is impeded by a removable restriction of a vertical channel 2511 ("dead-end"). For a second outlet, flow is allowed to continue unimpeded 2509.

Referring to FIG. 25, an orientation of outlets permits at least one portion of a dispersed phase to travel towards the dead-end 2511. Sometimes a density of a dispersed phase is less than a continuous phase such that a unit vector aligned with a central axis of a first outlet pointing at a dead-end deviates from a vector aligned with a local gravitational field and pointing in a direction of decreasing gravitational field strength by an angle less than 45°. Alternately or in combination a density of a dispersed phase is greater than that of the continuous phase such that a unit vector aligned with the central axis of the first outlet pointing at the dead-end deviates from a vector aligned with the local gravitational field and pointing in a direction of increasing gravitational field strength by an angle less than about 45°. Deviation can vary. In some instances, deviation is up to about 10°, 15°, 20°, 25°, 30°, 35°, 40°, or 45°. In some instances, deviation is at least 10°, 15°, 20°, 25°, 30°, 35°, 40°, 45°, or more than 45°. In some instances, deviation is about or within a range spanning 10°, 15°, 20°, 25°, 30°, 35°, 40°, or 45°. In some instances, a deviation is less than about 10°.

In FIG. 25, at least two portions of a dispersed phase are gravitationally trapped together by a dead-end in a first outlet of the junction 2505. A continuous phase is free to flow through a second outlet of a junction 2517. At least one portion of a dispersed phase can have at least one surface energy. If, for example, a first portion of a dispersed phase with a first surface energy is combined with a second portion of a dispersed phase with a second surface energy, a combined surface energy will be lower. Often a combined surface energy is lower than a sum of a first surface energy and a second surface energy due to a reduction in total surface area occupied by a first portion of a dispersed phase and a second portion of a dispersed phase. In some instances, energy is added in order to combine a first portion of a dispersed phase and a second portion of a dispersed phase.

In some instances, at least one dispersed phase is surrounded by a surfactant. A surfactant can be electrically polarizable. In some cases where an external source is applied, at least one dispersed phase is distorted due to a polarization of a surfactant by an external source.

Figure 26:
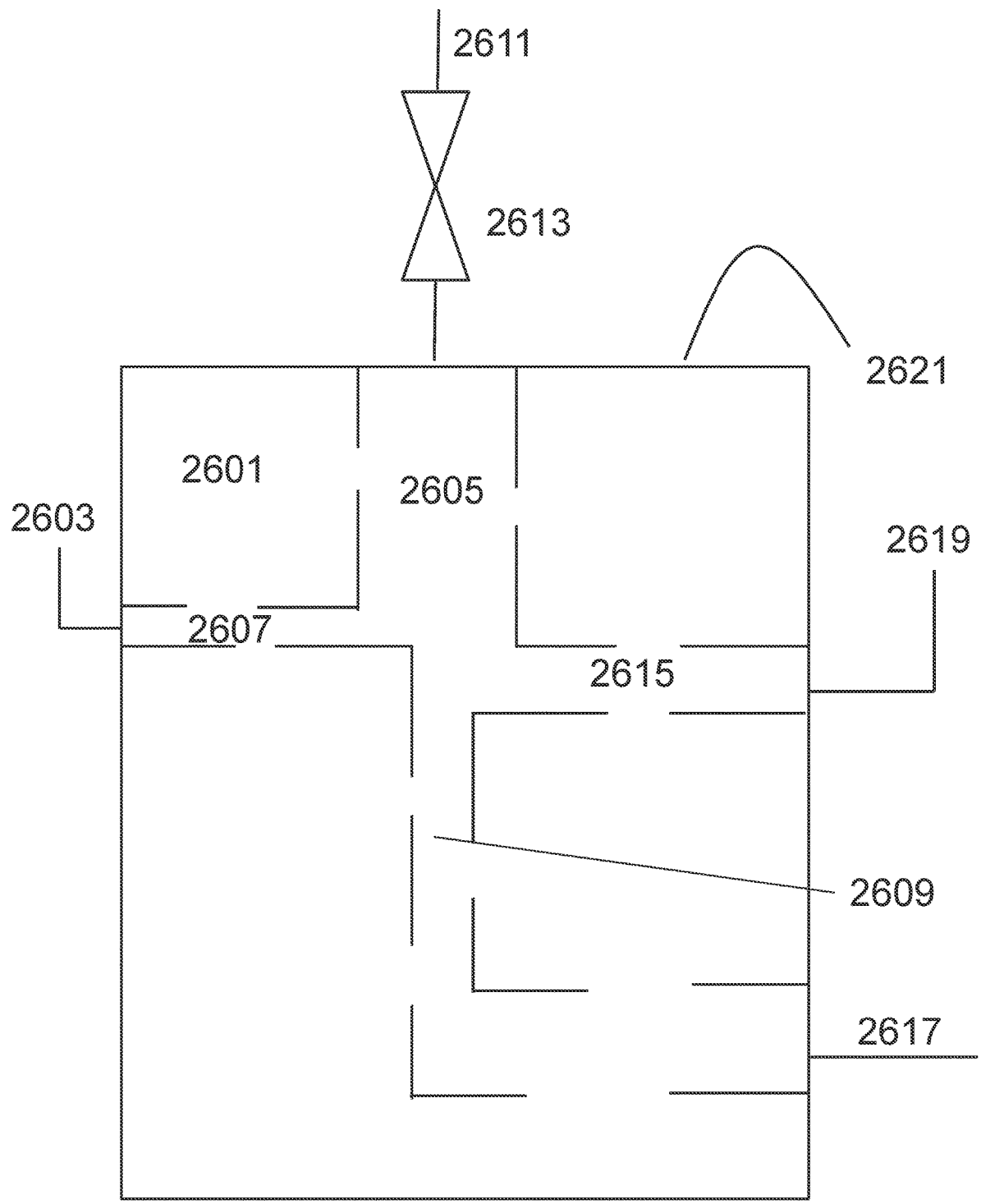
FIG. 26 depicts a cross section of a gravity-trap coalescer with smaller channel diameters.

FIG. 26 shows a junction formed from a monolith. As shown, a monolith takes an approximately cylindrical shape. There is a first axis of a monolith 2621 perpendicular to a cross section of the monolith, and a junction of the monolith contains at least one point on an axis. A monolith contains junction inlets 2603, 2619 and junction outlets 2611, 2617. In some instances, a dispersed phase has a lower mass density than a continuous phase. A junction outlet 2617 is coaxial with an axis of a monolith 2621. A junction outlet 2611 continues through an upper plane of a monolith 2621. In some instances, a junction outlet is continued by a fitted with a leak-resistant seal to an upper plane of the monolith. In some instances, a channel comprises tubing with an internal diameter that is at least 0.05, 0.10, 0.15, 0.20, 0.25, 0.50, 0.75, 1.0, 1.5, 2.0, 2.5, 3.0, or more than 3.0 mm. In some instances, a diameter of a tube is at most 0.05, 0.10, 0.15, 0.20, 0.25, 0.50, 0.75, 1.0, 1.5, 2.0, 2.5, 3.0, or more than 3.0 mm. Tubing can be fitted in a monolith by at least one of ablation, etching, molding, drilling, press-fitting, or poking. Tubing in some instances is coated with a material with a high affinity for a continuous phase. For example, if a continuous phase is a fluorinated oil, tubing is coated with a fluoropolymer.

Figure 27:
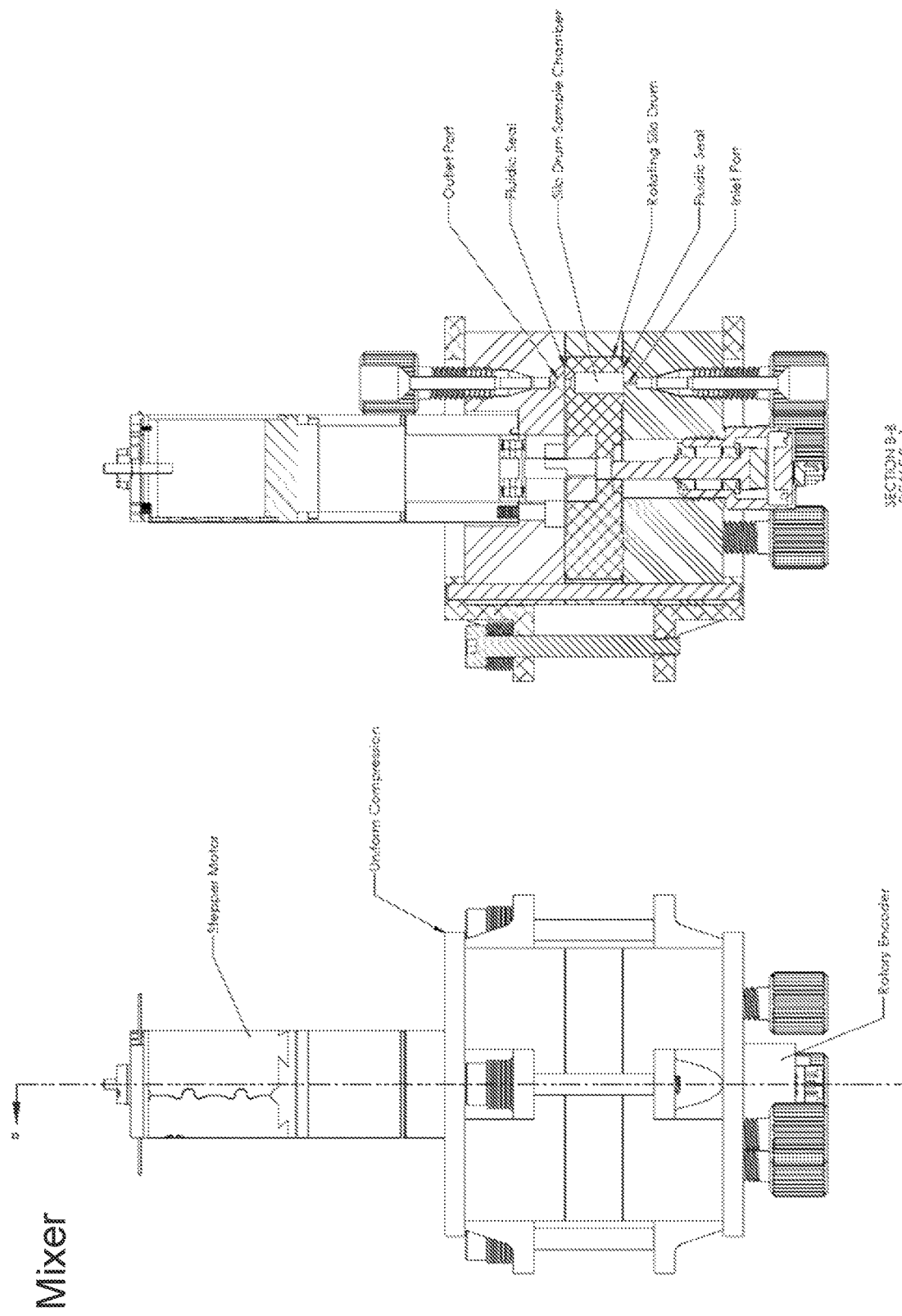
FIG. 27 depicts components of a gravity-trap coalescer with a rotating seal.
Figure 28:
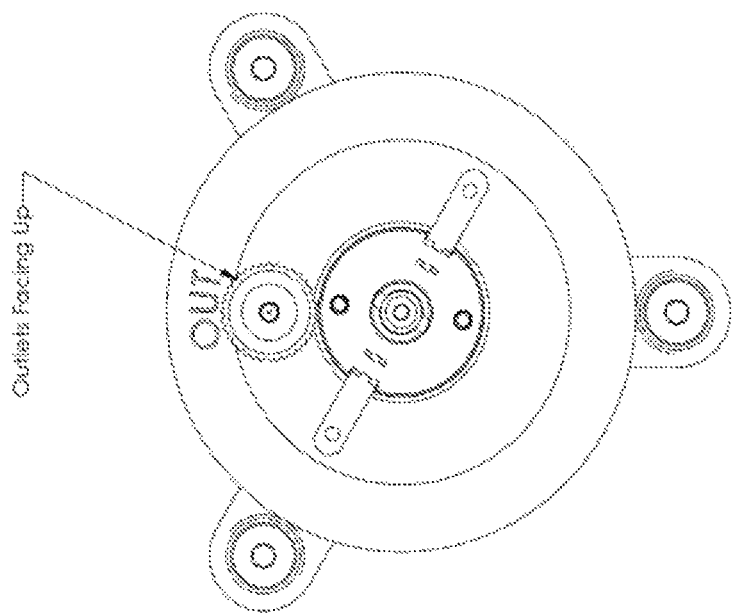
FIG. 28 depicts an arrangement of inlets and outlets of a gravity-trap coalescer.
Figure 28:
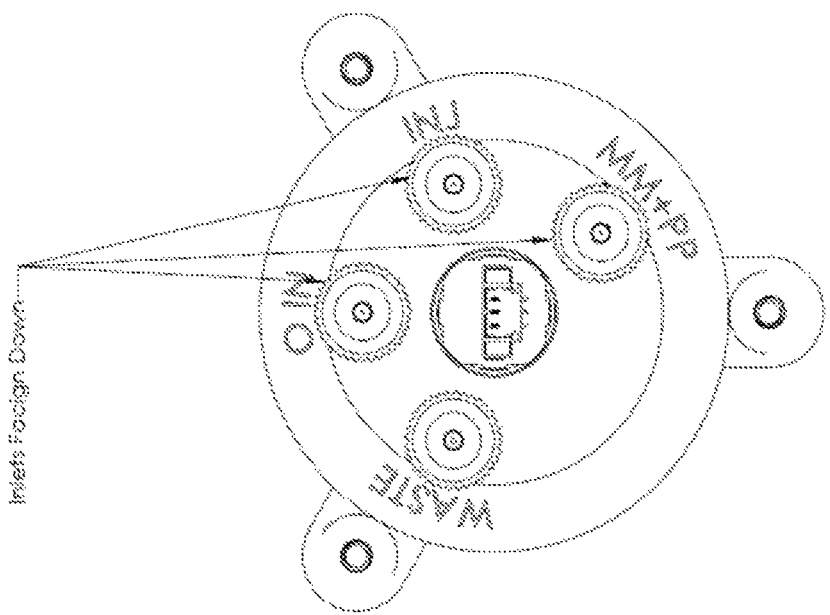
Figure 29:
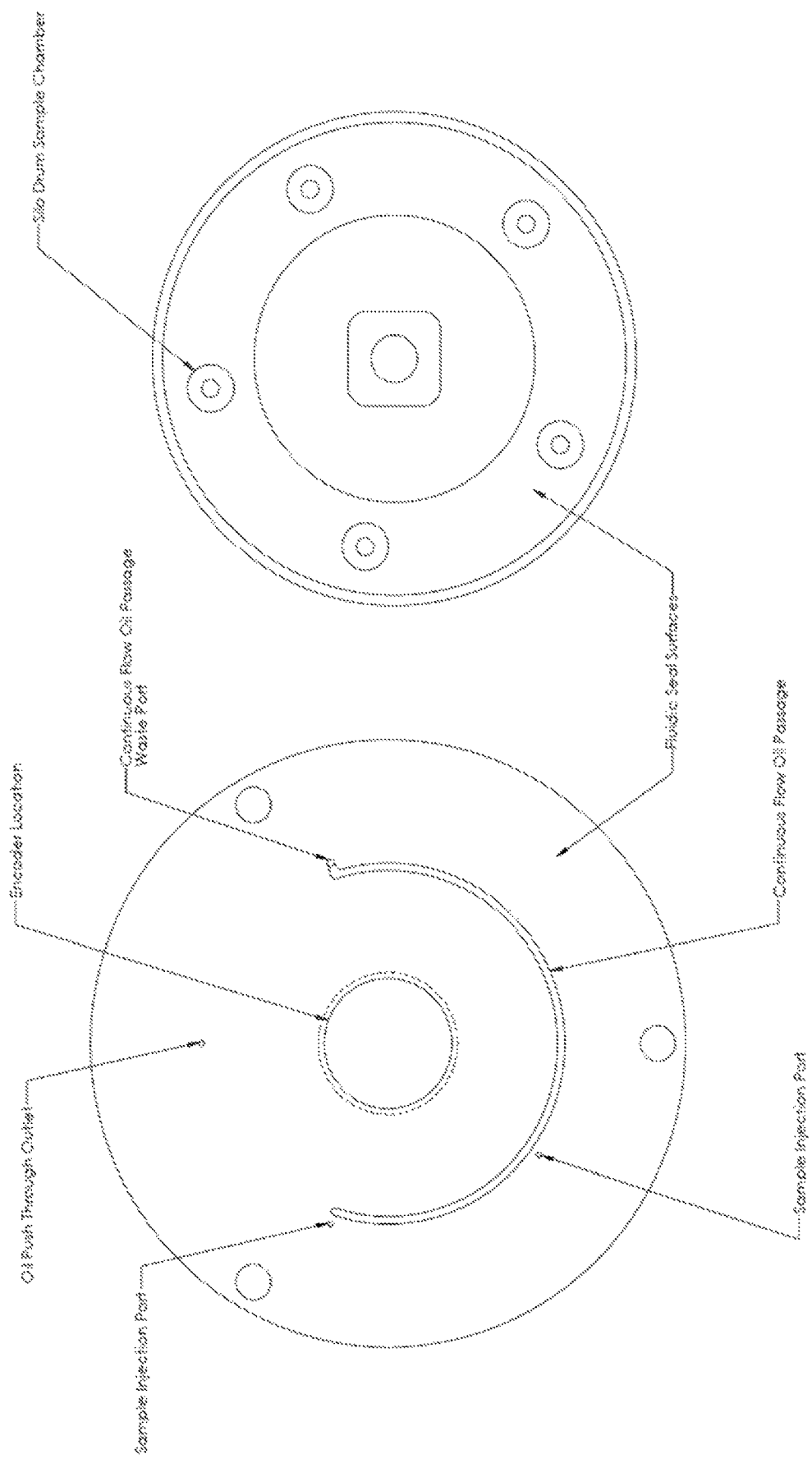
FIG. 29 depicts an arrangement of a cavity of a gravity-trap coalescer.
Figure 30:
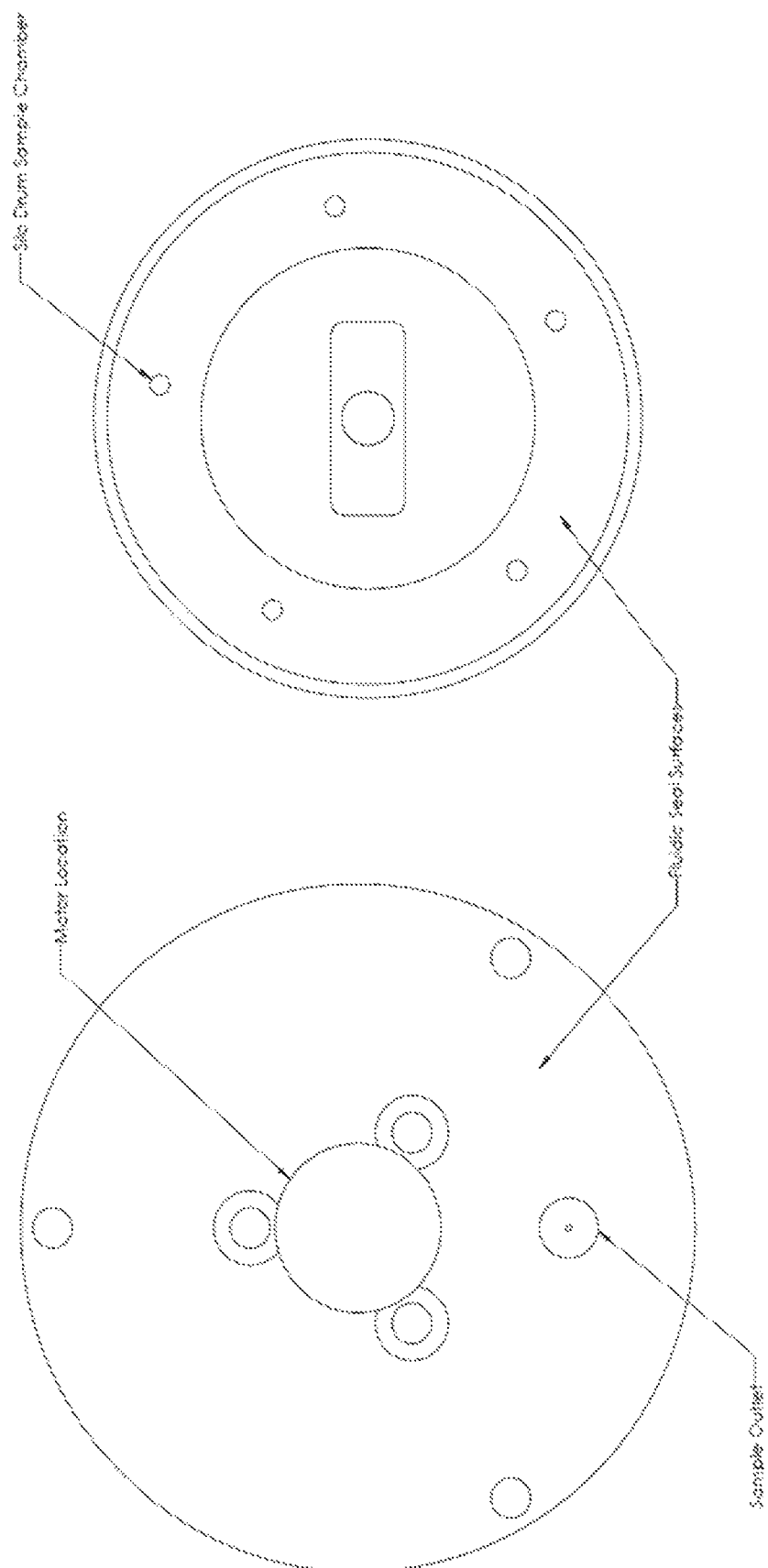
FIG. 30 depicts an alternate arrangement of a cavity of a gravity-trap coalescer.

FIG. 27 depicts components of an example of a gravity-trap coalescer. FIG. 28 depicts an arrangement of inlets and outlets of an example of a gravity-trap coalescer. FIG. 29 depicts an arrangement of a cavity of an example of a gravity-trap coalescer. FIG. 30 depicts an alternate arrangement of a cavity of an example of a gravity-trap coalescer.

In some instances, a dispersed phase has a greater mass density than a continuous phase and an orientation of junction outlets are reversed. A junction outlet passes through at least one of a lower plane of a monolith, through an upper plane of a monolith, or a cylindrical side plane of a monolith. An inlet of a junction comprises at least one point on an axis of a junction, and an inlet continues through a cylindrical side plane of a monolith. In some instances, a distance between a lower plane of the monolith and a point where a junction inlet intersects a cylindrical side plane of a monolith is not equal to a distance from the lower plane of a monolith to the point where an inlet of a junction intersects a cylindrical side plane of the monolith. Distance can be measured from a circumference point of a lower plane of a monolith perpendicular to a cross section of a lower plane of a monolith to a point on a plane perpendicular to an axis of the monolith comprising an intersection point of a cylindrical side plane of a monolith and an axis of an inlet junction. In some cases, these distances are the same. In some instances, an azimuthal position of a first inlet as measured from an azimuthal position on a circumference of a monolith is different from an azimuthal position of a second inlet of the junction. An azimuthal position of a first inlet and a second inlet can be the same. In some cases, a distance is chosen to accommodate assembly considerations. For example, if a leak-resistant seal of various junctions is created by a large connector or is low in profile, a distance such as an azimuthal position is adjusted for a size and position of a seal.

In some cases, a continuous phase is in contact with a surface of a monolith. Sometimes a continuous phase is a fluorinated oil. In some instances, a dispersed phase comprises a fluorophilic material. An exemplary fluorophilic material is a fluoropolymer. In some instances, a fluoropolymer is selected from a list of materials including, but not limited to, polyvinylfluoride (PVF), polyvinylidene fluoride (PVDF), polytetrafluoroethylene (PTFE), polychlorotrifluoroethylene (PCTFE), perfluoroalkoxy polymer, fluorinated ethylene-propylene (FEP), polyethylenetetrafluoroethylene (ETFE), polyethylenechlorotrifluoroethylene (ECTFE), Perfluorinated Elastomer, Fluorocarbon, Fluoroelastomer, Perfluoropolyether (PFPE), Perfluorosulfonic acid (PFSA), and Perfluoropolyoxetane. In some instances, an entire monolith is fabricated from a fluoropolymer so as to eliminate the need for lining or coating the fluid pathways with fluorophilic material.

A monolith as described herein can be fabricated easily. For example, junction outlets a single operation such as on a lathe or a drill press. In some cases, a monolith is composed of a metal from a list including, but not limited to, steel, aluminum, chromium, nickel, copper, or iron. Sometimes surfaces of a monolith intended to be in fluid contact with a continuous phase are lined or coated with fluorophilic material. In some instances, a lining is achieved by inserting an annular segment of fluoropolymer into the cylindrical open regions of the monolith that comprise the inlets and outlets of the junction, where the difference between the outer diameter of the fluoropolymer segment and the inner diameter of the cylindrical open regions of the monolith is in the range, with the fluoropolymer segment being of slightly larger outer diameter than the inner diameter of the cylindrical open regions of the monolith so as to compress and exert an elastic force normal to the inner diameter of the cylindrical open regions of the monolith and make a liquid-tight seal with the monolith.

Surfaces of a monolith that contact a continuous phase can be coated with fluorophilic material. In some instances, coating is achieved, but is not limited to, by chemical vapor deposition (CVD), physical vapor deposition (PVD), initiated chemical vapor deposition (i-CVD), atomic layer deposition (ALD), molecular layer deposition (MLD), atmospheric pressure CVD (APCVD), low-pressure CVD (LPCVD), ultrahigh vacuum CVD (UHVCVD), aerosol assisted CVD (AACVD), direct liquid injection CVD (DLICVD), microwave plasma-assisted CVD (MPCVD) plasma-enhanced CVD (PECVD), and combustion chemical vapor deposition (CCVD).

In some instances, a coalescer comprises a removable restriction. A removable restriction can be at least one of a gate valve, needle valve, ball valve, a rotating pin, or sliding pin. According to an example removable restriction on a junction outlet of a monolith of material, a cylindrical port extends from a point coaxial with an axis of a junction outlet perpendicular to a cross section of a junction and point. A cylindrical plug of material compatible with the monolith is inserted into the port so as substantially cover the cross section of the first outlet of the junction. A portion of the cylindrical plug extends into a junction outlet composed of a fluorophilic material. An opening in cylindrical plug permits a range of rotational positions such that an outlet is closed so no portion of a dispersed phase passes. An opening in cylindrical plug also permits a range of rotational positions such that an outlet is open and dispersed phase can exit. In some cases, a cylindrical plug has a greater outer diameter than an inner diameter of a cylindrical port. Sometimes a tight seal is provided between a cylindrical plug and a monolith. A cylindrical plug can be elastic. In some instances, a small range of rotational positions is permitted.

According to a second example of a removable restriction for a junction outlet, an outlet of the junction comprises a first cavity in a monolith and a fluid channel connected to the monolith by a leak-resistant seal. A removable restriction is created by a valve. A valve is composed of a material compatible with a continuous phase. In some instances, a continuous phase is a fluorinated oil, and the valve is composed of a fluorophilic material. A valve can be a gate valve or full-port ball valve. In some cases, a valve gate does not fully contact a valve body and allows a dispersed phase to pass. When a valve is full-port ball valve, an inner diameter of a port of a valve is the same as an inner diameter of an inlet or outlet channel. This can prevent portions of a dispersed phase from being caught or ruptured.

In some instances, dispersed phases coalesce using physical or electronic force such as electrostatic force, magnetic force, pressure force, or shear force. A force can be provided by an external source. For example, increased pressure is applied to a continuous phase such that a dispersed phase is isolated. In some instances, a coalescer uses gravity such that aqueous phases rise and oils do not. A shape of a chamber such as a conical shape can improve coalescing. In some instances, a first portion of a dispersed phase and a second portion of a dispersed phase combine spontaneously. In some instances, at least 2, 3, 4, 5, 6, 7, 8, 9, 10, or more than 10 dispersed phases are combined. In some instances, up to about 2, 3, 4, 5, 6, 7, 8, 9, 10, or more than 10 dispersed phases are combined. In some instances, at most, about, or a within a range spanning 2, 3, 4, 5, 6, 7, 8, 9, or 10 dispersed phases are combined. In some instances, following coalescing, coalesced droplets are further mixed by turbulent eddies. For example, turbulent eddies employ shear forces through fluid acceleration (e.g. through tubing bends or turbulizers) and laminar flow gradients for mixing coalesced droplets.

An external source is provided at a junction outlet during a coalescing state. Junction inlets and outlets contain only a dispersed phase. A junction outlet comprises both dispersed and continuous phase. A removable restriction in a junction outlet is in a "closed" state. A junction outlet is in an "open" state. In a "closed" condition, no portion of a dispersed phase is allowed to pass beyond the removable restriction. In some instances, a continuous phase may pass beyond the removable restriction. In a "flush" state, at least two portions of a dispersed phase have been combined. A removable restriction in a junction outlet has been opened, bringing an outlet to an "open" state and a combined dispersed phase and continuous phase to pass through a junction outlet. Junction inlets and outlets comprise a continuous phase. A junction outlet is in an "open" state. No external source is applied to an outlet. In some instances, an outlet such as comprises a removable restriction. During a "flush" state a junction outlet is closed such that a continuous phase exits through a junction outlet. In a "ready" state, junction inlets and outlets comprise a continuous phase. A junction outlet is in a "closed" state, and a junction outlet is in an "open" state. No portions of dispersed phase are in a system. There is no external source applied at an outlet of a junction. At least two dispersed phases flow through a junction inlet.

According to an embodiment, an electric source provided at a junction outlet can include a first electrode and a second electrode positioned on opposing sides of junction outlet. A potential difference is created between electrodes as across a junction outlet. An electric field polarizes a surfactant surrounding a dispersed phase in a junction outlet and provides energy to combine at least two dispersed phases. In some instances, an electrode is shaped as a sharp point so as to increase electrical field intensity across junction outlets. In some instances, a first electrode is inserted in a first port of a monolith and a second electrode is inserted in a second port in the monolith. In some instances, a potential difference between electrodes is at least 100 V. In some instances, an electric potential is at least 100, 200, 500, 750, 1000, 2000, 3000, 4000, 5000, 6000, 7000, 8000, 9000, 10000, 15000, 20000, 25000, 30000, or 40000, 50000, 60000, 70000, 80000, 90000, or more than 100000 V. In some instances, a potential difference is up to about 100, 200, 500, 750, 1000, 2000, 3000, 4000, 5000, 6000, 7000, 8000, 9000, 10000, 15000, 20000, 25000, 40000, 50000, 60000, 70000, 80000, 90000, or more than 100000 V. In some instances, a potential difference is at least, at most, about, or within a range spanning 100, 200, 500, 750, 1000, 2000, 3000, 4000, 5000, 6000, 7000, 8000, 9000, 10000, 15000, 20000, 25000, 30000, 40000, 50000, 60000, 70000, 80000, 90000, or 100000 V. Electric potential can be in a range of about 50-3000, 100-25000, 200-20000, 300-18000, 400-17000, 500-16000, 600-15000, 700-14000, 800-13000, 900-12000, 1000-10000, 1200-8000, 1400-7000, 1600-6000, 1800-5000, and 2000-4000 V. In some cases, an electric potential is in a range of about 1000 V to about 10000 V. Sometimes a current is direct. In some instances, a current is alternating in a range of about 10 kHz to 100 kHz. In some cases, an alternating current is at least 5, 10, 20, 30, 40, 50, 60, 60, 70, 80, 90, 100, 110, 120, 130, 140, 150, or more than 150 kHz. In some instances, an alternating current is up to about 5, 10, 20, 30, 40, 50, 60, 60, 70, 80, 90, 100, 110, 120, 130, 140, 150, or more than 150 kHz. In some cases, an alternating current is at most, about, or within a range spanning 5, 10, 20, 30, 40, 50, 60, 60, 70, 80, 90, 100, 110, 120, 130, 140, or 150 kHz.

In some instances, a dispersed phase has an electrical conductivity greater than an electrical conductivity of a continuous phase. The difference in conductivities can cause movement of charges or ions so as to partially or wholly cancel an electric field. In some instances, surfaces of a dispersed phase have a non-zero surface charge where different volumes of dispersed phases have opposing charges and attract each other. A continuous phase can then be displaced. In some cases, a necessary energy is provided to disrupt surfaces and coalesces the volumes of dispersed phases.

According to an additional example of adding external source to the first outlet of the junction, removable restrictions can prevent passage of a continuous and a dispersed phase. An inlet port is between a junction outlet and removable restrictions. An inlet port can be filled with continuous phase and is connected to a means of increasing the pressure in the continuous phase. During a loading state, a first removable restriction is open while a second removable restriction is closed such that portions of dispersed phases are collected at by gravity trapping. Once all portions of a dispersed phase are collected at a first removable restriction is closed. Coalescing can begin where a pressure of a continuous phase is increased at an inlet port in order for portions of dispersed phases to combine. Pressure can be increased by at least one of a pump such as a reciprocating pump or a peristaltic pump. Alternately or in combination, increasing temperature is used to coalesce dispersed phases.

Droplet Generator

In some embodiments, a merged droplet formed by coalescing a first droplet comprising sample of nucleic acids and a second droplet comprising reagents can be supplied to a droplet generator. For example, a merged droplet generated by a coalescer as described herein can be flowed to the droplet generator. The droplet generator can be configured to fractionate a merged droplet into multiple droplets. In some embodiments, each of the multiple droplets formed by fractionating the merged droplet comprises sufficient nucleic acids and reagents to perform a desired chemical reaction.

In some instances, the droplet generator comprises a T-junction type fractionator configured to fractionate fluids, such as the merged droplets. Alternately or in combination, droplets are generated by fluid agitation, microfluidic flow junctions, and/or spontaneously. A merged droplet is often transported to a droplet generator in an immiscible fluid, such as one or more oils described herein. Surfaces of a droplet generator can be at least one of fluorophilic and hydrophobic.

In some cases, a droplet generator further divides a droplet into multiple droplets. In some embodiments, the droplet generator can be configured to generate at least about 1000, 2000, 4000, 6000, 8000, 10000, 12000, 14000, 16000, 18000, 20000, 25000, 30000, 40000, 50000, 100000, 200000, 500000, 1 million, 2 million, 3 million, 4 million, 5 million, 10 million droplets. In some cases, the droplet generator can be configured to generate up to about 1000, 2000, 4000, 6000, 8000, 10000, 12000, 14000, 16000, 18000, 20000, 25000, 30000, 40000, 50000, 100000, 200000, 500000, 1 million, 2 million, 3 million, 4 million, 5 million, 10 million droplets. In some embodiments, the droplet generator is configured to generate at least, at most, about, or within a range spanning 1000, 2000, 4000, 6000, 8000, 10000, 12000, 14000, 16000, 18000, 20000, 25000, 30000, 40000, 50000, 100000, 200000, 500000, 1 million, 2 million, 3 million, 4 million, 5 million, or 10 million droplets.

In some instances, droplets generated by the droplet generator have a diameter of at least about 10, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, or more than 1000 microns (μm). In some cases, droplets have a diameter of at most about 10, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 μm. In some cases, droplets have a diameter of at least, at most, about, or within a range spanning 10, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 μm.

Reactor

Described herein are systems for detecting and quantifying at least one target molecule. In some instances, a chemical reaction is induced by a reactor. The reactor may comprise at least one of a temperature, electric field, magnetic field, acoustic energy, and electromagnetic radiation source configured to induce the chemical reaction.

In some instances, a reactor comprises a thermocycler. Traditional thermocyclers operate in which a reaction is fixed and a temperature within a thermocycler is raised or lowered according to a determined thermal profile. A thermal cycler as described herein can include at least two temperature zones that are at fixed respective temperatures. The temperatures can be selected based on the chemical reaction for which the reactor is configured to induce. A droplet comprising a quantity of sample nucleic acids and reagents for a desired chemical reaction, or a reaction droplet, is often brought into thermal contact with the at least two temperature zones. In some cases, a reaction droplet is flowed through a channel such that alternate thermal contact between zones of different temperatures can be achieved. As a result, often a thermocycler configured this way is more efficient.

In some instances, a reaction droplet passes through a reactor or a thermocycler to achieve a predetermined thermal profile. The thermal profile can be selected to induce the desired chemical reaction. In some embodiments, the thermal profile can be selected to induce nucleic acid amplification reaction. The reaction droplet can be flowed through the reactor or thermocycler to achieve nucleic acid amplification in the reaction droplet. For example, a reaction droplet can be held at a first temperature for a first specified duration of time and a second temperature for a second specified duration of time. In some embodiments, thermal contact between a reaction droplet and at least two temperature zones can be oscillated to achieve the desired thermal profile. A reactor thermocycler can have at least 1, 2, 3, 4, 5, 6, 7, 8, or more than 8 zones or sources. In some instances, a reactor or thermocycler has up to about 1, 2, 3, 4, 5, 6, 7, or 8 zones or sources. A reactor or thermocycler can have at most, about, or within a range spanning 1, 2, 3, 4, 5, 6, 7, or 8 zones or sources. In some cases, a zone comprises a specific temperature. A zone temperature or temperature source can be at least about 10° C., 20° C., 30° C., 40° C., 50° C., 60° C., 70° C., 80° C., 90° C., or 95° C. A zone temperature or temperature source can be at least, at most, about, or within a range spanning 10° C., 20° C., 30° C., 40° C., 50° C., 60° C., 70° C., 80° C., 90° C., or 95° C. or greater. For example, a zone or source has a temperature of 95° C. such as for activation of nucleic acid amplification enzymes. In some cases, a first temperature zone or first temperature source has a temperature in a range of 85° C. or less to 95° C. or greater. A second temperature zone or second temperature source can be in a range of 55° C. or less to 70° C. or greater. In some instances, a second zone or second temperature source has a temperature of, less than, greater than, about or within no more than one degree of 60° C. Temperature for a temperature zone or temperature source can be selected to enable at least one of a nucleic acid denaturing, a nucleic acid annealing, and a nucleic acid extension stage of a nucleic acid amplification reaction.

A thermocycler often comprises tubing wound around one or more components configured to be maintained at different temperatures. Reaction droplets can be flowed through the tubing such that the reaction droplets to achieve desired thermal profile for the reaction droplets. In some instances, tubing winds around a heating block. In some embodiments, the thermocycler comprises tubing wound around two heating blocks, each heating block being configured to be maintained at a particular temperature. In some cases, tubing is wound in a serpentine manner. Tubing can have an internal hydraulic diameter in a range of about 0.000001 inch (") and about 0.25." Tubing can have an internal hydraulic diameter in a range of about or less than 0.000001 inch (") to about or greater than 5.0." In some cases, an internal diameter is at least about 0.000001", 0.000005", 0.00001", 0.00005", 0.0001", 0.0005", 0.001", 0.005", 0.01", 0.05", 0.1", 0.5", or 1.0". In some cases, an internal diameter is at most about 0.000001", 0.000005", 0.00001", 0.00005", 0.0001", 0.0005", 0.001", 0.005", 0.01", 0.05", 0.1", 0.5", 1.0", or more than 1.0." In some cases, an internal diameter is at least, at most, about, or within a range spanning 0.000001", 0.000005", 0.00001", 0.00005", 0.0001", 0.0005", 0.001", 0.005", 0.01", 0.05", 0.1", 0.5", 1.0", 1.5", 2.0", 2.5", 3.0", 3.5", 4.0", 4.5", or 5.0". A thermocycler in some instances comprises microfluidic channels on a chip.

In some instances, reaction time is determined by flow velocity within a tubing and/or channel. In some cases, reaction time is determined by a length of a tubing and/or channel. Often reaction time is varied by varying at least one of the flow velocity and the length. In some cases, a reaction droplet is passed through tubing and/or channels in contact with at least two heating blocks more than once. For example, a number of times a reaction droplet is passed through tubing and/or channels in contact with at least two heating blocks allows for a corresponding number of nucleic acid amplification cycles.

In traditional thermocyclers, to accommodate multiple wraps around a heating block, an axis of a channel is oriented such that there are buoyancy issues. Specifically, droplets of dispersed phase could not completely fill the channel diameter and droplets of different sizes could potentially move at different speeds due to buoyancy. This potentially leads to axial dispersion of droplets, droplet collisions, and potential coalescence, breakage, and contamination.

Thermocyclers as described herein can resolve buoyancy issues by constraining flow to a planar or substantially planar arrangement. In some embodiments, the thermocycler comprises one or more heating blocks comprising a slab configuration. A heating block can be a heating card. In some embodiments, a thermocycler can comprise a heating block for each temperature zone. In some instances, a tubing and/or channel is placed into heat transfer communication with each heating block and passes within each zone in a serpentine fashion. A thermocycler can comprise tubing on the exterior of each heating block configured to wrap around each heating block where the tubing travels along a direction that is perpendicular to the longest dimension of each heating block.

Alternately, a thermocycler comprises a block without tubing. For example, the thermocycler comprises one or more blocks comprising channels within each of the one or more blocks. The channels can wrap around a heating block and travel in a direction perpendicular to its longest dimension. Exemplary channels include a microfluidic channel created within a heating block or a part of a microfluidic channel created into a heating block. In some cases, a channel contains a capping layer. Sometimes a capping layer has high thermal conductivity.

In some embodiments, a thermocycler comprises both tubing and channels in thermal contact with one or more heating blocks. In some embodiments, the thermocycler comprises self-contained flexible tube adhered to a heating block. In some cases, a flexible tube is adjusted to match a desired surface pattern on a heating block. In some cases, a flexible tub fits in a heating block within a pre-cut channel on a surface of a block.

In some cases, a thermocycler is configured as to improve at least one of conductive heat transfer and temperature uniformity. For example, this is done through use of a high thermal conductivity paste to eliminate air gaps within the thermocycler, such as between the tubing and one or more surfaces of the heating block.

In some instances, a thermocycler induces one or more chemical reactions for reverse transcription prior to amplification. In some cases, this is achieved by a separate heating block set at a temperature configured to induce reverse transcription. The heating block may comprise a rectangular shape. In some cases, a system comprises a set of selector valves to allow a user to choose whether to flow reaction droplets through a heating block configured to induce reverse transcription. In some instances, a separate heating block is set at a temperature configured for nucleic acid amplification which includes a "hot-start" step for enzyme activation, such as for polymerase activation. In some embodiments, the "hot-start" step can be performed at a temperature of about 95° C. to activate a polymerase.

Alternately or in combination to temperature, a reaction is induced by application of electromagnetic radiation. Electromagnetic radiation is in some instances provided outside of a reaction flow pathway where a reactional flow pathway is partially transparent to electromagnetic radiation of at least one frequency. In some instances, a reaction flow pathways comprises tubing of at least one of glass, ceramic, or polymeric material. In some cases, a reaction flow pathway is a channel in a material that is transparent to at least one frequency of electromagnetic radiation. Wavelengths of electromagnetic radiation is in some cases at least about 10, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, or more than 1000 nm. In some instances, wavelengths of electromagnetic radiation is at most about 10, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 nm. In some instances, wavelengths of electromagnetic radiation is at least, at most, about, or within a range spanning from less than 10, 10, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000 nm, or greater than 1000 nm.

Droplet Detection

After passing a reaction through a reactor such as a thermocycler, droplets are often individually analyzed. As described herein, in some embodiments, a system comprises a detector downstream of a reactor. In some instances, the system comprises a device configured to introduce fluid, such as through a fluid junction, into a droplet stream to further separate droplets from one another prior to flowing the droplets to the detector. Once droplets are separated, a detector is often set to acquire at least 1 data point per passing droplet. In some instances, at least 1, 5, 10, 15, 20, 25, 30, 40, 50, 60, 70, 80, 90, 100, 125, 150, 175, 200, 225, 250, 275, 300, 325, 350, 375, 400, 425, 450, 475, 500 or more than 500 data points are collected per droplet. In some cases, up to about 1, 5, 10, 15, 20, 25, 30, 40, 50, 60, 70, 80, 90, 100, 125, 150, 175, 200, 225, 250, 275, 300, 325, 350, 375, 400, 425, 450, 475, 500 or more than 500 data points are collected per droplet. In some cases, at least, at most, about, or within a range spanning 1, 5, 10, 15, 20, 25, 30, 40, 50, 60, 70, 80, 90, 100, 125, 150, 175, 200, 225, 250, 275, 300, 325, 350, 375, 400, 425, 450, 475, or 500 data points are collected per droplet.

Droplets in some cases then flow through a droplet detector and a signal is detected. Often a droplet is measured at least one of optically, electrically, mechanically, and magnetically. A signal can be, but is not limited to at least one of intensity of electromagnetic radiation, frequency of electromagnetic radiation, strength of an electric or magnetic field, or orientation of an electric or magnetic field. In some cases, a droplet is compared against a background. Alternately or in combination, a droplet is compared against another droplet. For example, a concentration is quantified by determining a number of droplets comprising at least one target nucleic acid molecule compared to droplets that did not. In some instances, a ratio of a number of droplets with a target molecule and a number of droplets that did not comprise a target molecule is calculated to determine a concentration per droplet.

Often a mathematical operational principal of one or more systems described herein apply to target molecules which follow a Poisson distribution model. The Poisson distribution models the number of times an event occurs in an interval of time when those events occur under certain conditions. For example, an event is a number of times a droplet containing a concentration of target molecules occurs per droplet. The Poisson distribution is an appropriate model since the following assumptions are true for the way in which the droplets are formed:

k is the number of target molecules that might be found in a single droplet. k can take values 0, 1, 2, etc.

The occurrence of a droplet with some value k does not affect the probability that other droplets will occur with any other value k. That is, droplet occupancy by target molecules occurs independently in every droplet.

The rate at which droplets are generated with some value k is constant. The rate cannot be higher in some intervals and lower in other intervals.

The probability that a droplet with concentration k will occur in some interval is proportional to the length of the interval.

When these conditions are met, k is said to be a Poisson random variable, and the distribution of k is a Poisson distribution. Thus, the distribution of molecule targets in the droplets takes on the form, $$P[k] = \frac{e^{-\mu}\mu^k}{k!}.$$

Where P[k] is the Poisson distribution, which may be interpreted as the probability that a droplet selected at random in an interval will contain k copies of a target molecule when $\mu$ is the average concentration of the molecule per droplet in that interval. While k is an integer, $\mu$ is a some real number between 0 and the maximum value of k in the interval. For an assay measuring the concentration of a target component, units or molecules of the target component will be distributed across the droplets by a Poisson distribution, and the probability that a given droplet will contain k units or molecules of the target component is given by P[k]. The detector in the system cannot distinguish between 1 and more than 1 components, but it can distinguish between 0 and 1 or more copies. The probability of achieving zero copies can be estimated by P[0]=N[0]/(N[0]+N[1+]), where N[0] is the number of droplets with zero copies and N[1+] is the number of copies with one or more copies. For this system, N[0] can be determined by counting the number of droplets with an emission intensity falling below a threshold intensity of emission and N[1] can determined by counting the number of droplets with an emission intensity exceeding a threshold intensity. Using the equation for P[k], with k=0, we get that p=−ln(N[0]/(N[0]+N[1])), where ln is the natural logarithm.

Thus, the ratio of the number of droplets in the population with zero units or molecules of targets to the total number of droplets in the population provides a direct measurement of the average concentration $\mu$. This is true for any continuous interval in the droplet stream. By multiplying this measured value by the sum total volume of all reaction droplets in an interval, the absolute concentration of the target molecule contained in the interval is measured as $$C = \mu \sum V_d,$$

where C is the target molecule concentration in the sample, $V_d$ is the droplet volume and $\Sigma V_d$ is the total reaction volume contained in the interval. This straightforward approach to target concentration quantification is made possible by the highly precise and repeatable nature of the sample injector, coalescer and droplet generator. Specifically, the droplet volume is known ahead of time by controlling the total volume injected. Competing approaches multiply the predicted droplet volume by the total number of droplets, requiring that the droplet size be precisely controlled and droplets that do not conform to this size be rejected. This introduces significant complexity into their hardware design and software analysis and it degrades their accuracy, precision, and sensitivity (because some droplets have to be rejected). It is the design of the injector and mixer in conjunction with the droplet generator that allows for our precise and repeatable aliquoting. By allowing for flexibility in generated droplet numbers and size, and by obviating the need to exclude outlier droplets in the measurement to obtain values for N[0] and N[1], this instrument is able quantify target molecule concentrations with a lower theoretical limit of detection, over arbitrary dynamic range, and with more accuracy than other currently used commercial approaches.

A droplet detector comprises at least one of an optical excitation source, a collimating optic, a dichroic filter, an objective optic, an emission filter, a detector, an excitation filter, and a pinhole filter. Exemplary optical excitation sources are a laser, light emitting diode, a photodiode, a photomultiplier tube, and a filtered broadband source. In some instances, an excitation source is power gated or is continuously powered. In some instances, a pinhole filter is located in front of a detector to occlude adjacent droplets and fluids from a central droplet that is analyzed. Alternately or in combination, a pinhole when positioned at a back focal plane of an objective acts as a confocal aperture. A confocal aperture in some cases excludes auto-emission and scattering from outside a focal volume. In some cases, a droplet detector contains a fluid channel. A fluid channel can be constricted to allow an individual droplet to pass in an axis perpendicular to an optical axis. A sliding focuser can be used to position a fluid channel in three orthogonal directions about a focal volume.

In some instances, a detector measures emitted electromagnetic radiation following exposure to an excitation source such as electromagnetic radiation. Sometimes a detector comprises at least 1, 2, 3, 4, 5, 6, 7, 8, 9, 10 or more than 10 excitation sources. In some cases, a detector comprises 3 excitation sources. In some cases, a detector comprises at least, at most, about, or within a range spanning 1, 2, 3, 4, 5, 6, 7, 8, 9, or 10 excitation sources. In some instances, excitation is in a range of about 300 to about 900 nm. Excitation can be at least about 300, 350, 400,450, 500, 550, 600, 650, 700, 750, 800, 850, or 900 nm. Sometimes excitation is at most about 300, 350, 400,450, 500, 550, 600, 650, 700, 750, 800, 850, 900, or more than 900 nm. In some instances, excitation is at least, at most, about, or within a range spanning 300, 350, 400,450, 500, 550, 600, 650, 700, 750, 800, 850, or 900 nm. A detector can measure at least 1, 2, 3, 4, 5, 6, 7, 8, 9, 10 or more than 10 frequency ranges emitted by a dispersed phase. A detector can measure at most, about, or within a range spanning 1, 2, 3, 4, 5, 6, 7, 8, 9, or 10 frequency ranges emitted by a dispersed phase. Sometimes a detector measures 3 frequency ranges. Emission can be at least about 300, 350, 400,450, 500, 550, 600, 650, 700, 750, 800, 850, 900, or more than 900 nm. Sometimes emission is at most about 300, 350, 400,450, 500, 550, 600, 650, 700, 750, 800, 850, 900, or more than 900 nm. Emission can be at least, at most, about, or within a range spanning 300, 350, 400,450, 500, 550, 600, 650, 700, 750, 800, 850, or 900 nm. In some instances, an optical filter is used. An optical filter can be used to block electromagnetic radiation outside of a desired frequency range or a set of desired frequency ranges. Sometimes an optical pinhole is used to prevent electromagnetic radiation emitted by a dispersed phase from reaching a photodetector.

Figure 31:
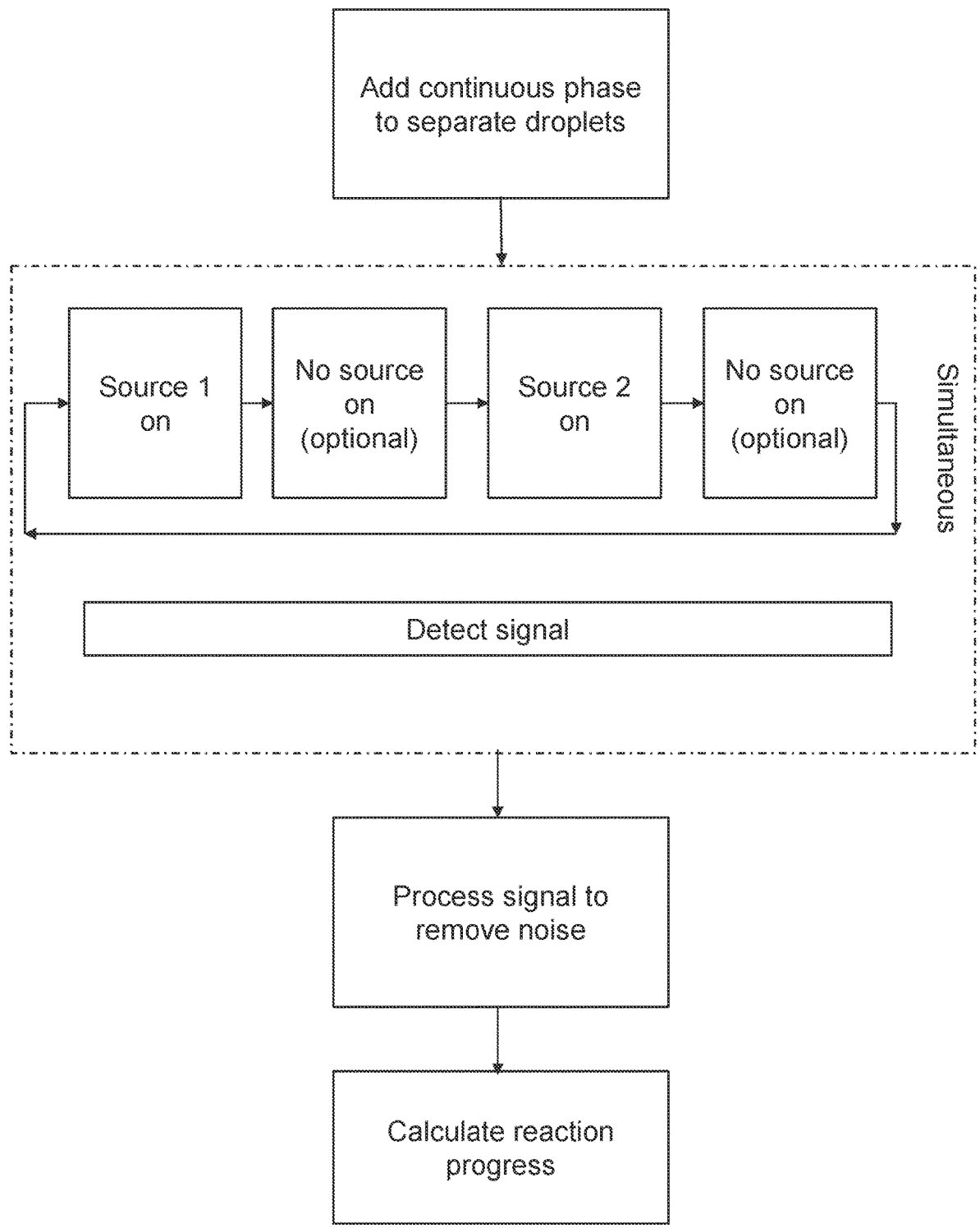
FIG. 31 depicts a process workflow for a detector.

FIG. 31 shows an example of a process workflow for a detector comprising modulated excitation to perform multiplexing. In some instances, a detector workflow comprises an excitation source and detection. As shown in FIG. 31, a continuous phase can be added to the flow pathway to increase distance between adjacent droplets prior to introducing the droplets to the detector. The droplets can be exposed to one or more excitation sources such that signals generated by the droplets due to the stimulation can be detected. The detected signals can be processed to remove any noise present in the system, and used to make various measurements such as to determine the progress of the reaction.

Figure 32:
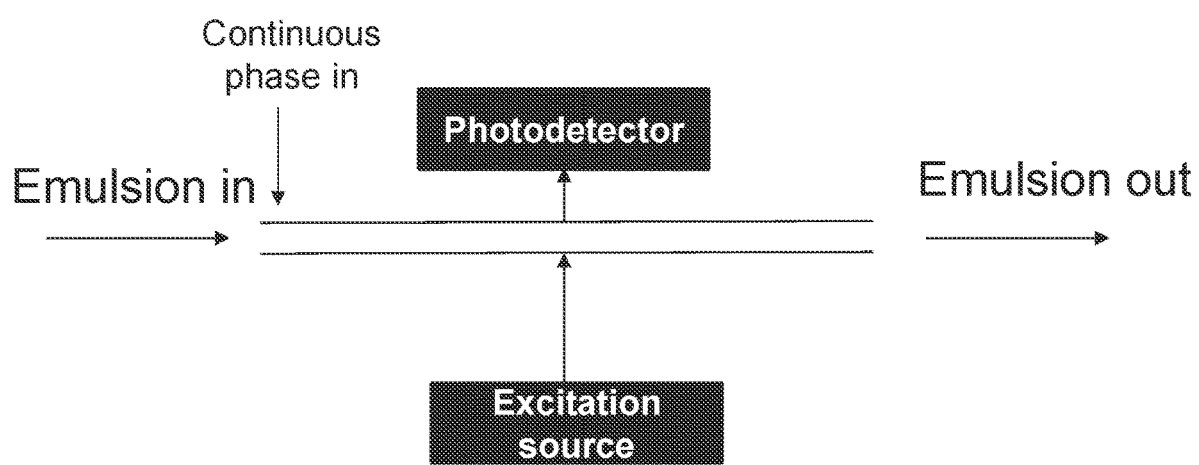
FIG. 32 depicts a configuration of a detector comprising a photodetector and an excitation source not co-located with the photodetector.

Referring to FIG. 32, a detector comprises a source of continuous phase and inlet for a continuous phase that is upstream of where a dispersed phase is illuminated by electromagnetic radiation. A continuous phase is injected to spatially separate volumes of dispersed phase (FIG. 32).

Figure 33:
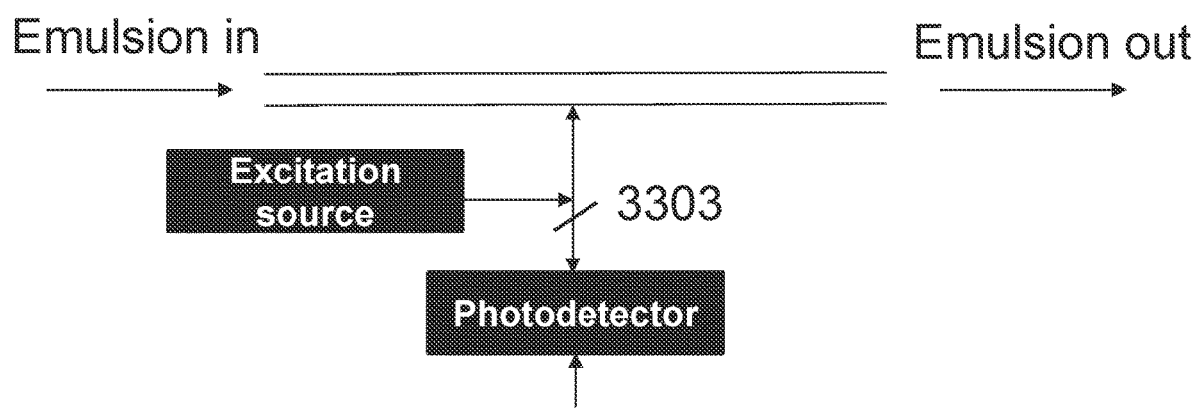
FIG. 33 depicts a configuration of a detector comprising a photodetector, an excitation source, and a dichroic turning mirror.
Figure 34:
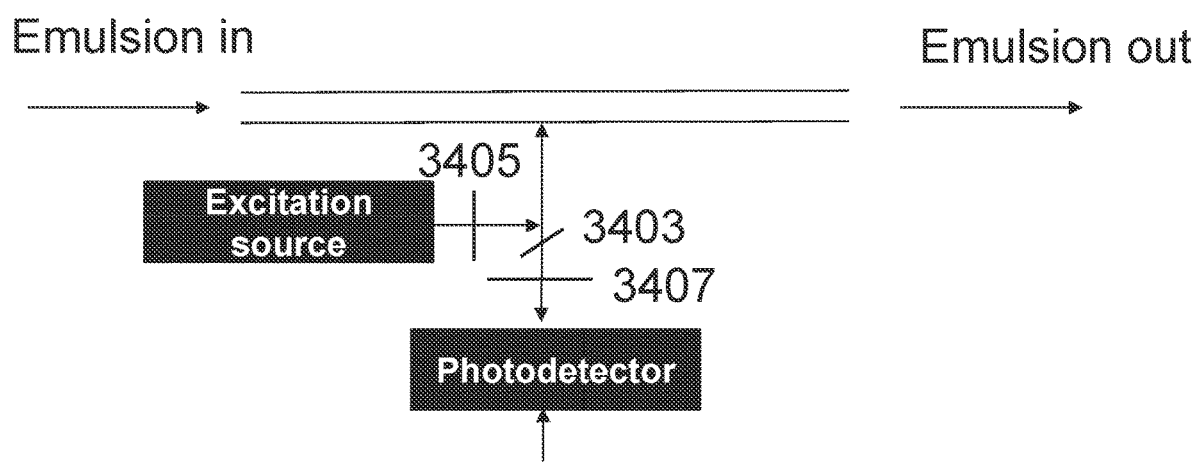
FIG. 34 depicts a configuration of a detector comprising a photodetector, an excitation source, a dichroic turning mirror, and filters.
Figure 35:
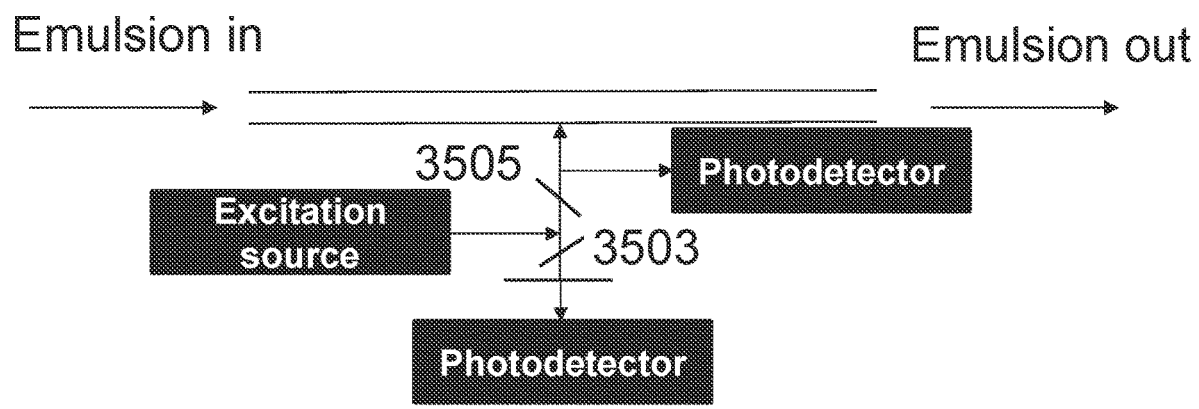
FIG. 35 depicts a configuration of a detector comprising two photodetectors, an excitation source, and two dichroic mirrors.
Figure 36:
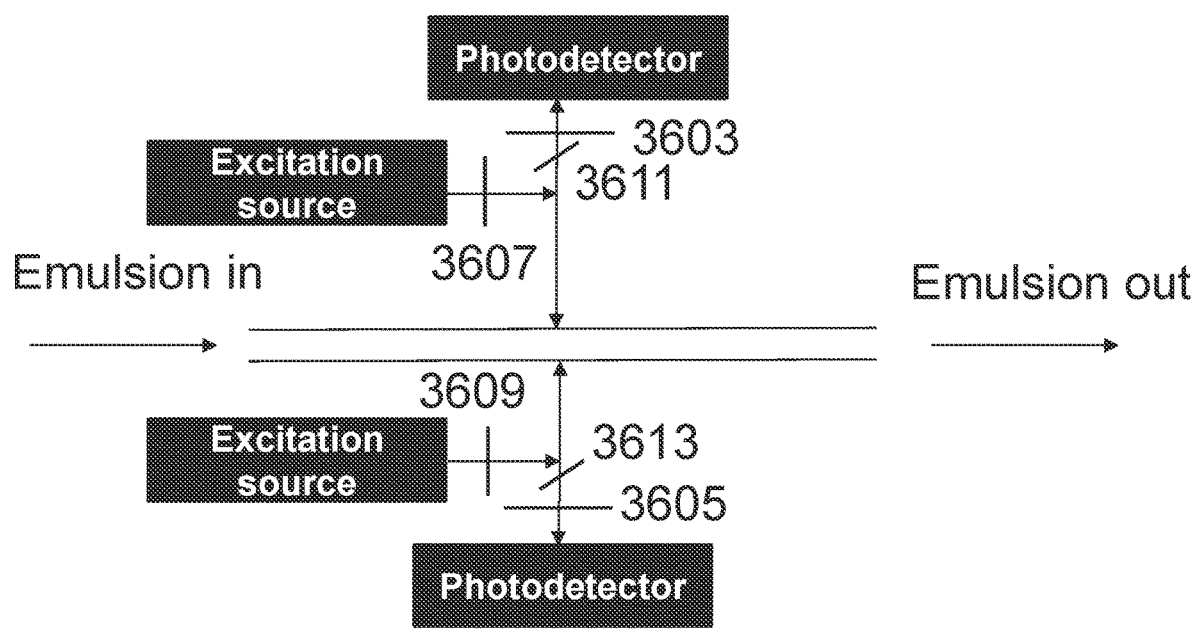
FIG. 36 depicts a configuration of a detector comprising two photodetectors, two excitation sources, filters, and dichroic mirrors.

Referring to FIG. 33 and FIG. 34, a detector comprises an excitation source, a photodetector, at least one dichroic mirror 3303, 3403, and at least one filter 3405, 3407. In some instances, a detector comprises at least 1, 2, 3, 4, 5, 6, 7, 8, 9, 10, or more than 10 dichroic mirrors. In some instances, a detector comprises at most, about, or a number within a range spanning 1, 2, 3, 4, 5, 6, 7, 8, 9, or 10 dichroic mirrors. In some instances, a detector comprises at least 1, 2, 3, 4, 5, 6, 7, 8, 9, 10, or more than 10 filters. In some instances, a detector comprises at most, about, or a number within a range spanning 1, 2, 3, 4, 5, 6, 7, 8, 9, or 10 filters. In some instances, a detector comprises 2 dichroic mirrors 3503, 3505 (e.g. FIG. 35). Referring to FIG. 36, a detector comprises at least one excitation source and at least one photodetector. Each photodetector comprises at least one filter 3603, 3605 that is positioned between a reaction flow pathway and a photodetector. Referring to FIG. 36, a detector comprises at least one filter 3607, 3609 and at least one dichroic mirror 3611, 3613 (FIG. 36).

Figure 37:
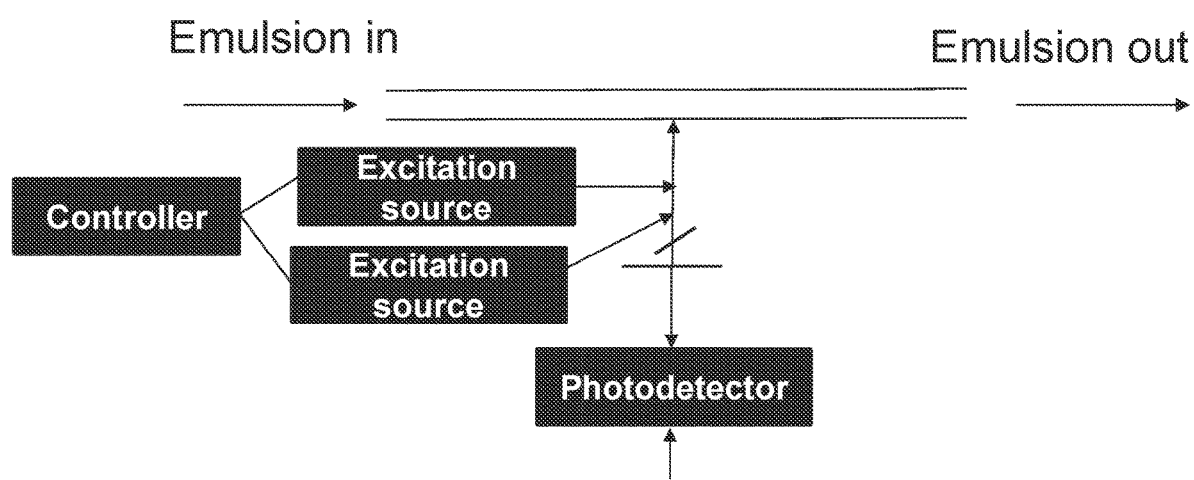
FIG. 37 depicts a configuration of a detector comprising a photodetector, two excitation sources, and a controller.

In some instances, a detector comprises a controller. A controller can be used to alternate between on and off states for excitation sources (e.g. FIG. 37). For example, a controller alternates between an off state of a first excitation source and an on state of a second excitation source. In some instances, a controller applies signal filtering to increase a signal-to-noise ratio. An exemplary signal filtering is a lock-in amplifier. In some instances, a portion of a reaction flow pathway is transparent. A controller can synchronize data from a detector to assign a signal to a volume of a dispersed phase.

Figure 38:
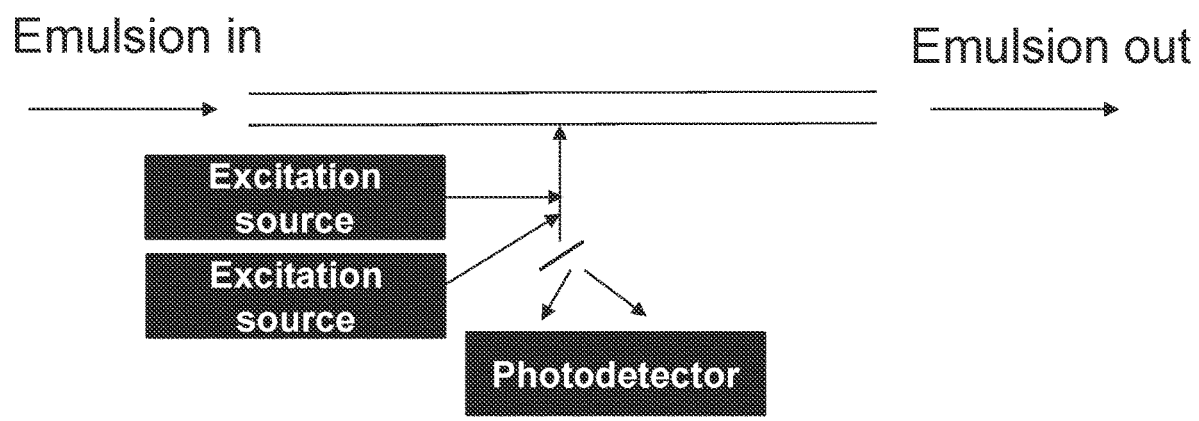
FIG. 38 depicts a configuration of a detector comprising two excitation sources and a photodetector.
Figure 39:
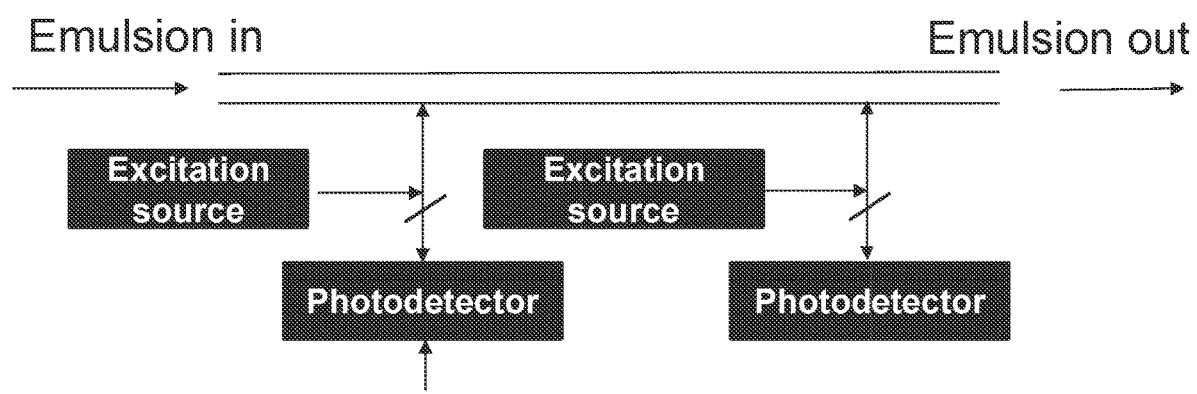
FIG. 39 depicts a configuration of a detector to allow for multiplexing.

In some instances, progress of a reaction is followed simultaneously. For example, a system comprises multiple excitation sources and multiple photodetectors that can detect said multiple excitation sources. In some instances, a portion of a reaction flow pathway is transparent. A reaction flow pathway can be transparent to an excitation source such that a dispersed phase can be excited by electromagnetic radiation and intensity of radiation can be correlated to a progress of a reaction. Sometimes a detector comprises a dispersive grating to spatially differentiate an electromagnetic radiation emitted by one source from a second source (e.g. FIG. 38). FIG. 39 depicts a configuration of a detector to allow for multiplexing. For example, as shown in FIG. 39, the detector can comprise two detection regions, comprising a first excitation source and photodetector spaced apart from a second excitation source and photodetector.

A photodetector can comprise multiple detection regions. In some instances, a signal is generated from the activity of an optically-responsive species such as, a dye or fluorescent probe. Examples of dyes include SYBR green I, SYBR green II, SYBR gold, ethidium bromide, methylene blue, Pyronin Y, DAPI, acridine orange, Blue View or phycoerythrin. A wide variety of reactive fluorescent probes can also be used. The fluorophore can be an aromatic or heteroaromatic compound. The fluorophore can be, for example, a pyrene, anthracene, naphthalene, acridine, stilbene, benzoxaazole, indole, benzindole, oxazole, thiazole, benzothiazole, canine, carbocyanine, salicylate, anthranilate, xanthenes dye, coumarin. Exemplary xanthene dyes include, e.g., fluorescein and rhodamine dyes. Fluorescein and rhodamine dyes include, but are not limited to 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N; N'-tetramethyl-6-carboxyrhodamine (TAMRA), 6-carboxy-X-rhodamine (ROX). Suitable fluorescent probes also include the naphthylamine dyes that have an amino group in the alpha or beta position. For example, naphthylamino compounds include 1-dimethylaminonaphthyl-5-sulfonate, 1-anilino-8-naphthalene sulfonate and 2-p-toluidinyl-6-naphthalene sulfonate, 5-(2'-aminoethyl)aminonaphthalene-1-sulfonic acid (EDANS). Exemplary coumarins include, e.g., 3-phenyl-7-isocyanatocoumarin; acridines, such as 9-isothiocyanatoacridine and acridine orange; N-(p-(2-benzoxazolyl)phenyl) maleimide; cyanines, such as, e.g., indodicarbocyanine 3 (Cy3), indodicarbocyanine 5 (Cy5), indodicarbocyanine 5.5 (Cy5.5), 3-(-carboxy-pentyl)-3'-ethyl-5,5'-dimethyloxacarbocyanine (CyA); 1H, 5H, 11H, 15H-Xantheno[2,3, 4-ij: 5,6, 7-i'j']diquinolizin-18-ium, 9-[2 (or 4)-[[[6-[2,5-dioxo-1-pyrrolidinyl)oxy]-6-oxohexyl]amino]sulfonyl]-4 (or 2)-sulfophenyl]-2,3, 6,7, 12,13, 16,17-octahydro-inner salt (TR or Texas Red); or BODIPY™ dyes.

Multi fluorophore signals can be measured simultaneously. For example, multiple target sequences in a nucleic acid amplification reaction is analyzed by using multiple sequence specific probes conjugated to reporting dyes that emit different frequencies. In some instances, at least 1, 2, 3, 4, 5, 6, 7, 8, 9, 10, 11, 12, 13, 14, 15, 16, 17, 18, 19, 20, or more than 20 multiple sequence specific probes are used. In some cases, up to about 1, 2, 3, 4, 5, 6, 7, 8, 9, 10, 11, 12, 13, 14, 15, 16, 17, 18, 19, 20, or more than 20 multiple sequence specific probes are used. In some instances, at most, about, or a number within a range spanning 1, 2, 3, 4, 5, 6, 7, 8, 9, 10, 11, 12, 13, 14, 15, 16, 17, 18, 19, or 20 multiple sequence specific probes are used. Rather than use multiple detectors, described herein are methods of multiplexing that can be performed using a single photodetector and multiple excitation sources. In some cases, multipass filters are used to send a light from each excitation source onto a sample and back to a detector. Such cycling between excitation source and detector can allow for multiplexing to be accomplished. In some cases, multiple reads per droplet at each wavelength is measured, which can be used to cancel out background. Sometimes cycling is used to amplify low-level signal, for example, in single molecule detection (e.g., antigens and other proteins). In some cases, serial multiplexing is performed.

In some instances, the systems and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular data types. For example, a sequence of instructions on a computer program is used for serial multiplexing to identify sequence targets to test. Identification of target sequences to test can be automated or chosen by a user.

In some instances, a computer program includes a stand-alone application, which is a program that is run as an independent computer process, not an add-on to an existing process, e.g., not a plug-in. For example, a user would select from an onboard touchscreen tests to be performed on a system.

In some cases, a computer comprises external devices. In some instances, communication between a computer and an external device occurs through at least one of physical cable, a storage device, a memory device, and a wireless connection. In some cases, a system interfaces with software system on a personal computer, tablet, or mobile device For example, a system includes a storage and/or memory device. The storage and/or memory device is one or more physical apparatuses used to store data or programs on a temporary or permanent basis. In some cases, the device is volatile memory and requires power to maintain stored information. Alternately or in combination, a device is non-volatile memory and retains stored information when the digital processing device is not powered. For example, non-volatile memory comprises at least one of flash memory, dynamic random-access memory (DRAM), ferro-electric random access memory (FRAM), phase-change random access memory (PRAM). In some cases, a device is a storage device including, by way of non-limiting examples, CD-ROMs, DVDs, flash memory devices, magnetic disk drives, magnetic tapes drives, optical disk drives, and cloud computing based storage. In some instances, the storage and/or memory device is a combination of devices such as those disclosed herein. Alternately or in combination, data could be stored in a database that can be accessed at a later point or analyzed by third-party applications.

Definitions

Unless otherwise defined, all technical terms used herein have the same meaning as commonly understood by one of ordinary skill in the art to which this invention belongs. 10.1641 As used herein, the term "comprising" and its grammatical equivalents specifies the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

As used herein, the singular form "a", "an" and "the" include plural references unless the context clearly dictates otherwise.

As used herein, the terms "amplifying" and "amplification" are used interchangeably and generally refer to producing one or more copies of a nucleic acid.

As used herein, the terms "nucleic acid" and "nucleic acid molecule" are used interchangeably and generally refer to a polymeric form of nucleotides of any length, either deoxyribonucleotides (dNTPs) or ribonucleotides (rNTPs), or analogs thereof. Nucleic acids may have any three dimensional structure, and may perform any function, known or unknown. Non-limiting examples of nucleic acids include deoxyribonucleic acid (DNA), ribonucleic acid (RNA), a peptide nucleic acid (PNA), coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs such as, for example, locked nucleic acids (LNA), fluorinated nucleic acids (FNA), bridged nucleic acids and thio-nucleotides. If present, modifications to the nucleotide structure may be made before or after assembly of the nucleic acid. The sequence of nucleotides of a nucleic acid may be interrupted by non-nucleotide components, such as, for example a linker or other type of spacer. A nucleic acid may be further modified after polymerization, such as by conjugation or binding with a detectable species. In some instances, a nucleic acid may be a primer that, in some embodiments, can be used to amplify another nucleic acid molecule.

As used herein, the term "primer" generally refers to a nucleic acid molecule that is capable of hybridizing with a template nucleic acid molecule and capable of being extended in a template-directed manner via the template nucleic acid molecule.

As used herein, the terms "target nucleic acid" and "target nucleic acid molecule" are used interchangeably and generally refer to a nucleic acid molecule in a starting population of nucleic acid molecules having a target sequence whose presence, amount, and/or nucleotide sequence, or changes in one or more of these, are desired to be determined. In some instances, a target nucleic acid molecule may be double-stranded. In some instances, a target nucleic acid molecule may be single-stranded. In general, the term "target nucleic acid strand" refers to a single-stranded target nucleic acid molecule. In general, the term "target nucleic acid sequence" refers to a nucleic acid sequence on a strand of target nucleic acid. A target nucleic acid molecule or target nucleic acid sequence can be a portion of a gene, a regulatory sequence, genomic DNA, cDNA, RNA including mRNA, miRNA, rRNA, or others. The target nucleic acid sequence or target nucleic acid molecule can be a target nucleic acid sequence or target nucleic acid molecule from a sample or a secondary target such as a product of an amplification reaction.

As used herein, the term "cylindrical" or its grammatical equivalents refers to a three-dimensional shape comprising a surface created by projecting a closed two-dimensional curve along an axis intersecting the plane of the curve. The curve may be, but is not in all cases limited to, a circle, a rectangle, or an oval. In some instances, the term "cylindrical" refers to a circular cylinder.

NUMBERED EMBODIMENTS

Numbered embodiment 1 comprises a system for automatically conducting an assay in a continuous flow, the system comprising: (a) a flow pathway comprising a first inlet for a continuous phase and a first outlet; (b) a first zero-dead volume injector, wherein the injector is configured to supply a first dispersed phase; (c) a second zero-dead volume injector, wherein the injector is configured to supply a second dispersed phase; (d) a coalescer; (e) a reactor; (f) a detector; and (g) a controller. Numbered embodiment 2 comprises the system of numbered embodiment 1, wherein the reactor is configured to induce a chemical reaction. Numbered embodiment 3 comprises the system of numbered embodiments 1-2, wherein the reactor comprises an external source of energy. Numbered embodiment 4 comprises the system of numbered embodiments 1-3, wherein the reactor is a thermocycler. Numbered embodiment 5 comprises the system of numbered embodiments 1-4, wherein the continuous phase comprises hydrophobic fluorinated oil. Numbered embodiment 6 comprises the system of numbered embodiments 1-5, wherein at least one of the first dispersed phase and the second disperse phase comprises water. Numbered embodiment 7 comprises the system of numbered embodiments 1-6, wherein a surface of the flow pathway comprises a fluoropolymer, and wherein at least one of the first dispersed phase and the second disperse phase does not contaminate the flow pathway. Numbered embodiment 8 comprises the system of numbered embodiments 1-7, wherein the fluorinated oil is at least one of FC-3283, FC-40, FC-43, FC-70, 3-ethoxy-1,1,1,2,3,4,4,5,5,6,6,6-dodecafluoro-2-trifluoromethyl-hexane, 2,2,3,3,4,4,4-heptafluoro-1-butanol, CF3CF2CF2CH2OH, perfluorooctane, perfluorohexane, 1,1,1-trifluorooctane, and 1,1,1,2,2-petantafluorodecane. Numbered embodiment 9 comprises the system of numbered embodiments 1-8 wherein the fluoropolymer is at least one of polyvinylfluoride (PVF), polyvinylidene fluoride (PVDF), polytetrafluoroethylene (PTFE), polychlorotrifluoroethylene (PCTFE), perfluoroalkoxy polymer, fluorinated ethylene-propylene (FEP), polyethylenetetrafluoroethylene (ETFE), polyethylenechlorotrifluoroethylene (ECTFE), perfluorinated elastomer, fluorocarbon, fluoroelastomer, perfluoropolyether (PFPE), perfluorosulfonic acid (PFSA), and perfluoropolyoxetane. Numbered embodiment 10 comprises the system of numbered embodiments 1-9, further comprising a surfactant. Numbered embodiment 11 comprises the system of numbered embodiments 1-10, wherein the surfactant is at least one of fluorocarbon, a hydrocarbon, and a silicone. Numbered embodiment 12 comprises the system of numbered embodiments 1-11, wherein a volume of at least one of the first dispersed phase and the second disperse phase is in a range of about 1 picoliter to about 1 milliliter. Numbered embodiment 13 comprises the system of numbered embodiments 1-12, wherein the flow pathway comprises an internal hydraulic diameter in a range of about 0.001" to about 0.5". Numbered embodiment 14 comprises the system of numbered embodiments 1-13, wherein the system performs a nucleic acid amplification reaction. Numbered embodiment 15 comprises the system of numbered embodiments 1-14, wherein the first dispersed phase comprises at least one nucleic acid molecule and wherein the second dispersed phase comprises a nucleic acid amplification reagent. Numbered embodiment 16 comprises the system of numbered embodiments 1-15, wherein a nucleic acid amplification reagent is at least one of a primer, a probe, mastermix, a dNTP, a buffer, and an enzyme. Numbered embodiment 17 comprises the system of numbered embodiments 1-16, wherein the flow pathway cycles from a first temperature zone to a second temperature zone to perform nucleic acid amplification. Numbered embodiment 18 comprises the system of numbered embodiments 1-17, wherein the detector measures a fluorescent signal. Numbered embodiment 19 comprises the system of numbered embodiments 1-18, wherein the coalescer comprises an external source of energy. Numbered embodiment 20 comprises the system of numbered embodiments 1-19, wherein the external source of energy is provided by an electric field between at least two electrodes. Numbered embodiment 21 comprises the system of numbered embodiments 1-20, wherein an electric potential between the at least two electrodes is in a range of about 100 V to about 25000 V. Numbered embodiment 22 comprises the system of numbered embodiments 1-21, wherein the external source is at least one of pressure source and mechanical source. Numbered embodiment 23 comprises the system of numbered embodiments 1-22, wherein the pressure source is supplied by a pump. Numbered embodiment 24 comprises the system of numbered embodiments 1-23, wherein the reactor comprises a fixed temperature zone. Numbered embodiment 25 comprises the system of numbered embodiments 1-24, wherein the reactor comprises at least two fixed temperature zones. Numbered embodiment 26 comprises the system of numbered embodiments 1-25, wherein a flow pathway cycles between the at least two fixed temperature zones. Numbered embodiment 27 comprises the system of numbered embodiments 1-26, wherein the reaction pathway cycles along at least one of a specified length and a rate. Numbered embodiment 28 comprises the system of numbered embodiments 1-27, wherein the first dispersed phase comprises a biological sample, and wherein the second dispersed phase comprises a lysis reagent. Numbered embodiment 29 comprises the system of numbered embodiments 1-28, wherein the first dispersed phase comprises a first drug precursor, and wherein the second dispersed phase comprises a second drug precursor. Numbered embodiment 30 comprises a system for automatically conducting an assay in a continuous flow, the system comprising: (a) a flow pathway comprising a first inlet for continuous phase and a first outlet; (b) a first zero-dead volume injector, wherein the injector supplies a first dispersed phase; (c) a second zero-dead volume injector, wherein the injector supplies a second dispersed phase; (d) a coalescer; (e) a reactor; (f) a droplet generator; (g) a detector; and (h) a controller, wherein a surface of the flow pathway has an increased affinity for the continuous phase, and wherein at least one of the first dispersed phase and the second dispersed phase is coated with a surfactant. Numbered embodiment 31 comprises the system of numbered embodiments 1-30, wherein a Poisson distribution is used to analyze an aggregate of droplets. Numbered embodiment 32 comprises the system of numbered embodiments 1-31, wherein the droplet generator creates a number of droplets in a range of about 2000 and about 1000000. Numbered embodiment 33 comprises the system of numbered embodiments 1-32, wherein the droplet generator creates a number of droplets in a range about 3000 and 30000. Numbered embodiment 34 comprises the system of numbered embodiments 1-33, wherein the system performs an emulsion-based digital nucleic acid amplification. Numbered embodiment 35 comprises the system of numbered embodiments 1-34, wherein the first dispersed phase comprises at least one target nucleic acid molecule, and wherein the second dispersed phase comprises a nucleic acid amplification reagent. Numbered embodiment 36 comprises the system of numbered embodiments 1-35, wherein the nucleic acid amplification reagent is at least one of a primer, a probe, mastermix, a dNTP, a buffer, and an enzyme. Numbered embodiment 37 comprises the system of numbered embodiments 1-36, wherein the detector measures a fluorescent signal. Numbered embodiment 38 comprises the system of numbered embodiments 1-37, wherein the fluorescent signal is at least one of a dye, fluorescent probe, molecular beacon, hybridization probe, and scorpion probe. Numbered embodiment 39 comprises the system of numbered embodiments 1-38, wherein the emulsion-based digital nucleic acid amplification is serially multiplexed. Numbered embodiment 40 comprises the system of numbered embodiments 1-39, wherein the emulsion-based digital nucleic acid amplification is parallely multiplexed. Numbered embodiment 41 comprises the system of numbered embodiments 1-40, wherein the controller automatically determines a threshold signal using automatic clustering algorithm. Numbered embodiment 42 comprises the system of numbered embodiments 1-41, where the automatic clustering algorithm is at least one of k-means clustering, single-linkage clustering, complete-linkage clustering, Gaussian mixture model, and density based clustering. Numbered embodiment 43 comprises the system of numbered embodiments 1-42, wherein the continuous phase comprises hydrophobic fluorinated oil. Numbered embodiment 44 comprises the system of numbered embodiments 1-43, wherein at least one of the first dispersed phase and the second dispersed phase comprises water. Numbered embodiment 45 comprises the system of numbered embodiments 1-44, wherein a surface of the flow pathway comprises a fluoropolymer, and wherein at least one of the first dispersed phase and a second dispersed phase does not contaminate the flow pathway. Numbered embodiment 46 comprises the system of numbered embodiments 1-45, wherein the fluorinated oil is at least one of FC-3283, FC-40, FC-43, FC-70, 3-ethoxy-1,1,1,2,3,4,4,5,5,6,6,6-dodecafluoro-2-trifluoromethyl-hexane, 2,2,3,3,4,4,4-heptafluoro-1-butanol, CF3CF2CF2CH2OH, perfluorooctane, perfluorohexane, 1,1,1-trifluorooctane, and 1,1,1,2,2-petantafluorodecane. Numbered embodiment 47 comprises the system of numbered embodiments 1-46, wherein the fluoropolymer is at least one of polyvinylfluoride (PVF), polyvinylidene fluoride (PVDF), polytetrafluoroethylene (PTFE), polychlorotrifluoroethylene (PCTFE), perfluoroalkoxy polymer, fluorinated ethylene-propylene (FEP), polyethylenetetrafluoroethylene (ETFE), polyethylenechlorotrifluoroethylene (ECTFE), perfluorinated elastomer, fluorocarbon, fluoroelastomer, perfluoropolyether (PFPE), perfluorosulfonic acid (PFSA), and perfluoropolyoxetane. Numbered embodiment 48 comprises the system of numbered embodiments 1-47, wherein the surfactant is at least one of a fluorocarbon, a hydrocarbon, and a silicone. Numbered embodiment 49 comprises the system of numbered embodiments 1-48, wherein the reactor cycles from a first temperature zone to a second temperature zone to perform nucleic acid amplification. Numbered embodiment 50 comprises the system of numbered embodiments 1-49, wherein the first temperature zone is in a range of about 85° C. to about 95° C. Numbered embodiment 51 comprises the system of numbered embodiments 1-50, wherein denaturation of DNA occurs in the first temperature zone. Numbered embodiment 52 comprises the system of numbered embodiments 1-51, wherein the second temperature zone is in a range of about 55° C. to about 70° C. Numbered embodiment 53 comprises the system of numbered embodiments 1-52, wherein at least one of annealing and extension occurs in the second temperature zone. Numbered embodiment 54 comprises the system of numbered embodiments 1-53, wherein a number of cycles in a range of about 25 to about 45. Numbered embodiment 55 comprises the system of numbered embodiments 1-54, further comprising a third temperature zone. Numbered embodiment 56 comprises the system of numbered embodiments 1-55, wherein reverse transcription occurs in the third temperature zone. Numbered embodiment 57 comprises the system of numbered embodiments 1-56, wherein a "hot-start" step of a nucleic acid amplification occurs in the third temperature zone. Numbered embodiment 58 comprises the system of numbered embodiments 1-57, wherein the first dispersed phase comprises at least one of RNA, DNA, and a protein. Numbered embodiment 59 comprises the system of numbered embodiments 1-58, wherein the second dispersed phase comprises at least one of an antigen, reporter molecule, a primer, a probe, mastermix, a buffer, and an enzyme. Numbered embodiment 60 comprises a method for automatically conducting an assay in a continuous flow, the method comprising: (a) preparing a sample comprising at least one target molecule in a first dispersed phase; (b) automatically injecting an desired quantity of the first dispersed phase into a flow pathway comprising the continuous phase of an emulsion; (c) automatically injecting a desired quantity of a second dispersed phase; (d) collecting the first dispersed phase and the second dispersed phase in a proximity to each other; (e) coalescing the first dispersed phase and the second dispersed phase; (f) generating a droplet from the combined first dispersed phase and second dispersed phase; (g) inducing a reaction in a droplet; (h) detecting the reaction; and (i) determining a quantity of target molecule in the sample by comparing the number of droplets with a detected final progress of the at least one chemical reaction in each droplet above a critical threshold with the number of droplets with a detected final progress of the at least one chemical reaction below the critical threshold. Numbered embodiment 61 comprises any one of numbered embodiments 1-60, further comprising adjusting automatically a parameter of a second assay determined by a feedback loop. Numbered embodiment 62 comprises any one of numbered embodiments 1-61, wherein a target molecule is at least one of DNA, RNA, and a protein. Numbered embodiment 63 comprises any one of numbered embodiments 1-62, wherein the reaction is nucleic acid amplification. Numbered embodiment 64 comprises any one of numbered embodiments 1-63, wherein a nucleic acid amplification reagent is at least one of a primer, a probe, mastermix, a dNTP, a buffer, and an enzyme. Numbered embodiment 65 comprises any one of numbered embodiments 1-64, further comprising lysing the sample. Numbered embodiment 66 comprises any one of numbered embodiments 1-65, wherein a volume of water is automatically injected following a result of a first assay. Numbered embodiment 67 comprises any one of numbered embodiments 1-66, wherein the sample is at least one of cells, viruses, microbes, and fluids. Numbered embodiment 68 comprises any one of numbered embodiments 1-67, wherein the sample is from a subject. Numbered embodiment 69 comprises a system for metering a volume of a dispersed phase of an emulsion, the system comprising: (a) a rotating drum comprising a monolith with a fixed internal open volume; (b) a first cap cover for the drum comprising a channel for an inlet; (c) a second cap cover for the drum comprising a channel for an outlet; (d) a means of inducing flow of dispersed phase through the first inlet to the first flow pathway; (e) a means of inducing flow of continuous phase through the second inlet to the second flow pathway, such that any dispersed phase contained in the fixed internal volume flows into the second flow pathway. Numbered embodiment 70 comprises any one of numbered embodiments 1-69, further comprising a plurality of inlets. Numbered embodiment 71 comprises any one of numbered embodiments 1-70, further comprising a plurality of outlets. Numbered embodiment 72 comprises any one of numbered embodiments 1-71, further comprising a plurality of ports for injection. Numbered embodiment 73 comprises any one of numbered embodiments 1-72, wherein a volume to be injected is in a range of about 1 uL to about 500 uL. Numbered embodiment 74 comprises any one of numbered embodiments 1-73, further comprising a cassette. Numbered embodiment 75 comprises any one of numbered embodiments 1-74, wherein the cassette is a reservoir for emulsion-based digital nucleic acid amplification reagents. Numbered embodiment 76 comprises a system for coalescing at least one volume of a dispersed phase in a continuous phase of an emulsion, the system comprising: (a) a first flow channel comprising a first inlet connected to a first source of dispersed phase and continuous phase of an emulsion; (b) a second flow channel comprising a second inlet connected to a second source of dispersed phase and continuous phase of an emulsion; (c) a third flow channel comprising a first outlet connected to a flow pathway, wherein a first axis is perpendicular to a cross section of the channel, and wherein the first axis forming an angle less than 450 with a second axis aligned with the direction of increasing gravitational field; (d) a removable restriction; (e) a fourth flow channel comprising a second outlet connected to a continuous phase outlet and wherein a third axis is at an angle less than 45° with the second axis for at least a portion of the length of the fourth flow channel; (f) a junction of the first flow channel, the second flow channel, the third flow channel, and the fourth flow channel; (g) an external source; and (h) a controller to perform coalescing automatically. Numbered embodiment 77 comprises any one of numbered embodiments 1-76, wherein the external source is applied to the third flow channel. Numbered embodiment 78 comprises any one of numbered embodiments 1-77, wherein at least one of the first flow channel, the second flow channel, the third flow channel, and the fourth flow channel is a cavity in a monolith. Numbered embodiment 79 comprises any one of numbered embodiments 1-78, wherein a cavity has a diameter in a range of about $\frac{1}{32}$" to about $\frac{1}{2}$". Numbered embodiment 80 comprises any one of numbered embodiments 1-79, wherein a length of the third flow channel and the fourth flow channel is in a range of about $\frac{1}{16}$" to about 6". Numbered embodiment 81 comprises any one of numbered embodiments 1-80, wherein at least one of the first flow channel, the second flow channel, the third flow channel, and the fourth flow channel comprises tubing. Numbered embodiment 82 comprises any one of numbered embodiments 1-81, wherein at least one of the first flow channel, the second flow channel, the third flow channel, and the fourth flow channel is arranged to increase coalescence. Numbered embodiment 83 comprises any one of numbered embodiments 1-82, wherein the removable restriction is at least one of a gate valve, needle valve, ball valve, a rotating pin, and a sliding pin. Numbered embodiment 84 comprises any one of numbered embodiments 1-83, wherein the external source is an electric field between at least two electrodes. Numbered embodiment 85 comprises any one of numbered embodiments 1-84, wherein an electric potential between the at least two electrodes is in a range of about 100 V to about 10000 V. Numbered embodiment 86 comprises any one of numbered embodiments 1-85, wherein an electric potential between the at least two electrodes is in a range of about 500 V to about 2000 V. Numbered embodiment 87 comprises any one of numbered embodiments 1-86, wherein the electric field has an alternating current in the range of about 10 kHz to about 100 kHz. Numbered embodiment 88 comprises any one of numbered embodiments 1-87, wherein the external source is at least one of pressure source and mechanical source. Numbered embodiment 89 comprises any one of numbered embodiments 1-88, wherein the pressure source is supplied by a pump. Numbered embodiment 90 comprises any one of numbered embodiments 1-89, wherein the controller controls a timing of coalescing. Numbered embodiment 91 comprises any one of numbered embodiments 1-90, wherein the at least one volume of the dispersed phase comprises a target molecule. Numbered embodiment 92 comprises any one of numbered embodiments 1-91, wherein the at least volume of the dispersed phase comprises an enzyme. Numbered embodiment 93 comprises any one of numbered embodiments 1-92, wherein the at least one volume of the dispersed phase comprises at least one of a primer, a probe, mastermix, a buffer, and a dNTP. Numbered embodiment 94 comprises a system for coalescing at least one volume of a dispersed phase in a continuous phase of an emulsion, the system comprising: (a) a first flow channel comprising a first inlet connected to a first source of a first dispersed phase and a first continuous phase of an emulsion; (b) a second flow channel comprising a second inlet connected to a second source of a second dispersed phase and a second continuous phase of an emulsion; (c) a third flow channel comprising a first outlet connected to a flow pathway, wherein a first axis is perpendicular to a cross section of the channel, and wherein the first axis forming an angle less than 450 with a second axis aligned with the direction of increasing gravitational field; (d) a removable restriction; (e) a fourth flow channel comprising a second outlet connected to a continuous phase outlet and wherein a third axis is at an angle less than 45° with the second axis for at least a portion of the length of the fourth flow channel; (f) a junction of the first flow channel, the second flow channel, the third flow channel, and the fourth flow channel; (g) an external source; (h) a controller to perform coalescing automatically; wherein a surface of at least one of the first flow channel, the second flow channel, the third flow channel, and the fourth flow channel has an increased affinity for at least one of the first continuous phase and second continuous phase, and wherein at least one of the first dispersed phase and the second dispersed phase is coated with a surfactant. Numbered embodiment 95 comprises a system for coalescing at least one volume of a dispersed phase in a continuous phase of an emulsion, the system comprising: (a) a flow channel connected to an input for a plurality of sources of a dispersed phase and a continuous phase in an emulsion; (b) a removable restriction; (c) an external source; and (d) a controller to perform coalescing automatically. Numbered embodiment 96 comprises any one of numbered embodiments 1-95, wherein a surface of a flow channel has an increased affinity for the continuous phase, and wherein the dispersed phase is coated with a surfactant. Numbered embodiment 97 comprises a system for automatically combining a known amount of at least one volume of a dispersed phase, the system comprising: (a) a first zero-dead volume injector, wherein the injector supplies a first dispersed phase; (b) a second zero-dead volume injector, wherein the injector supplies a second dispersed phase; and (c) a coalescer. Numbered embodiment 98 comprises any one of numbered embodiments 1-97, further comprising a source of a continuous phase and a second coalescer. Numbered embodiment 99 comprises any one of numbered embodiments 1-98, further comprising a droplet generator. Numbered embodiment 100 comprises any one of numbered embodiments 1-99, wherein the coalescer is connected to a plurality of injectors that provide a reagent to the coalescer. Numbered embodiment 101 comprises any one of numbered embodiments 1-100, wherein at least one injector of the plurality of injectors provides water. Numbered embodiment 102 comprises a method of coalescing at least one volume of a dispersed phase, the method comprising: (a) injecting a known volume of a first dispersed phase; (b) injecting a known volume of a second dispersed phase; (c) trapping the first dispersed phase and the second dispersed phase in a coalescer; (d) applying an external source; and (e) opening a removable restriction to a downstream flow pathway. Numbered embodiment 103 comprises any one of numbered embodiments 1-102, wherein the removable restriction is at least one of a gate valve, needle valve, ball valve, a rotating pin, and a sliding pin. Numbered embodiment 104 comprises any one of numbered embodiments 1-103, wherein the external source is an electric field between at least two electrodes. Numbered embodiment 105 comprises any one of numbered embodiments 1-104, wherein an electric potential between the at least two electrodes is in a range of about 100 V to about 10000 V. Numbered embodiment 106 comprises any one of numbered embodiments 1-105, wherein an electric potential between the at least two electrodes is in a range of about 500 V to about 2000 V. Numbered embodiment 107 comprises any one of numbered embodiments 1-106, wherein the electric field has a current in the range of about 10 kHz to about 100 kHz. Numbered embodiment 108 comprises any one of numbered embodiments 1-107, wherein the external source is at least one of pressure source or mechanical source. Numbered embodiment 109 comprises any one of numbered embodiments 1-108, wherein the pressure source is supplied by a pump. Numbered embodiment 110 comprises a system for quantifying an analyte in a sample, comprising a premeasured reagent cassette, a continuous reagent stream track, a sample input port, an injector, a coalescer, at least one temperature-controlled body, and a detector, wherein the system quantifies the analyte without requiring measured delivery of the sample to the sample input port. Numbered embodiment 111 comprises any one of numbered embodiments 1-110, further comprising a droplet generator. Numbered embodiment 112 comprises any one of numbered embodiments 1-111, wherein no step of operating the system requires measured aliquotting of a sample or reagent by a system operator. Numbered embodiment 113 comprises any one of numbered embodiments 1-112, wherein the analyte in the sample is quantified no more than 1 hour after the sample is introduced into the system. Numbered embodiment 114 comprises any one of numbered embodiments 1-113, wherein the analyte in the sample is quantified no more than 30 minutes after the sample is introduced into the system. Numbered embodiment 115 comprises any one of numbered embodiments 1-114, wherein the analyte in the sample is quantified no more than 20 minutes after the sample is introduced into the system. Numbered embodiment 116 comprises any one of numbered embodiments 1-115, wherein the system measures analyte presence in individual droplets of an emulsion. Numbered embodiment 117 comprises any one of numbered embodiments 1-116, wherein the system compares a measurement of analyte presence in individual droplets of an emulsion to a threshold value of frequency of analyte presence in individual droplets of an emulsion. Numbered embodiment 118 comprises any one of numbered embodiments 1-117, wherein when the measurement of analyte presence in individual droplets of an emulsion is above the threshold value, the system dilutes a remaining aliquot of the sample. Numbered embodiment 119 comprises any one of numbered embodiments 1-118, wherein the system measures analyte presence in individual droplets of an emulsion generated from a diluted remaining aliquot of the sample. Numbered embodiment 120 comprises any one of numbered embodiments 1-119, wherein when the measurement of analyte presence in individual droplets of an emulsion is below the threshold value, the system concentrates a remaining aliquot of the sample. Numbered embodiment 121 comprises any one of numbered embodiments 1-120, wherein the system measures analyte presence in individual droplets of an emulsion generated from a concentrated remaining aliquot of the sample. Numbered embodiment 122 comprises any one of numbered embodiments 1-121, wherein operation of the system does not require measured delivery of any reagent during measurement of an analyte in a sample. Numbered embodiment 123 comprises any one of numbered embodiments 1-122, wherein operation of the system does not require measured delivery of any reagent during measurement of a plurality of analytes in a sample. Numbered embodiment 124 comprises any one of numbered embodiments 1-123, wherein operation of the system does not require measured delivery of any reagent during measurement of a plurality of analytes in a plurality of samples. Numbered embodiment 125 comprises any one of numbered embodiments 1-124, wherein the analyte is a first analyte, and wherein the system quantifies a second analyte in the sample in a single sample run. Numbered embodiment 126 comprises any one of numbered embodiments 1-125, wherein the system quantifies a first sample in no more than 20 minutes. Numbered embodiment 127 comprises any one of numbered embodiments 1-126, wherein the system quantifies a second sample in no more than 5 minutes following quantification of the first sample Numbered embodiment 128 comprises any one of numbered embodiments 1-127, wherein the system quantifies a second sample in no more than 5 minutes following quantification of the first sample. Numbered embodiment 129 comprises any one of numbered embodiments 1-128, wherein the sample quantifies at least 20 samples. Numbered embodiment 130 comprises any one of numbered embodiments 1-129, wherein the sample quantifies at least 50 samples. Numbered embodiment 131 comprises any one of numbered embodiments 1-130, wherein the premeasured reagent cassette comprises reagents sufficient to analyze at least 10 samples. Numbered embodiment 132 comprises any one of numbered embodiments 1-131, wherein the premeasured reagent cassette comprises reagents sufficient to analyze at least 20 samples. Numbered embodiment 133 comprises any one of numbered embodiments 1-132, wherein the premeasured reagent cassette comprises reagents sufficient to analyze at least 50 samples. Numbered embodiment 134 comprises any one of numbered embodiments 1-133, wherein the premeasured reagent cassette comprises reagents sufficient to analyze at least 100 samples. Numbered embodiment 135 comprises any one of numbered embodiments 1-134, wherein the premeasured reagent cassette comprises reagents sufficient to analyze at least 1000 samples. Numbered embodiment 136 comprises any one of numbered embodiments 1-135, wherein the premeasured reagent cassette comprises a heat-activated reagent. Numbered embodiment 137 comprises any one of numbered embodiments 1-136, wherein the premeasured reagent cassette comprises a reverse-transcription reagent. Numbered embodiment 138 comprises any one of numbered embodiments 1-137, wherein the premeasured reagent cassette comprises a nucleic acid amplification reagent. Numbered embodiment 139 comprises any one of numbered embodiments 1-138, wherein the premeasured reagent cassette comprises a thermostable nucleic acid. Numbered embodiment 140 comprises a system for conducting an assay in a continuous flow, the system comprising: (a) flow pathway for a continuous phase comprising a first inlet and a first outlet; (b) a first zero-dead volume injector configured to supply a first dispersed phase; (c) a second zero-dead volume injector configured to supply a second dispersed phase; (d) a coalescer; (e) a reactor; (f) a detector; and (g) a controller. Numbered embodiment 141 comprises any one of numbered embodiments 1-140, wherein the continuous phase comprises a hydrophobic reagent. Numbered embodiment 142 comprises any one of numbered embodiments 1-141, wherein the continuous phase comprises an oil. Numbered embodiment 143 comprises any one of numbered embodiments 1-142, wherein the continuous phase comprises a hydrophobic fluorinated oil. Numbered embodiment 144 comprises any one of numbered embodiments 1-143, wherein the hydrophobic fluorinated oil comprises a reagent selected from a group consisting of FC-3283, FC-40, FC-43, FC-70, 3-ethoxy-1,1,1,2,3,4,4,5,5,6,6,6-dodecafluoro-2-trifluoromethyl-hexane, 2,2,3,3,4,4,4-heptafluoro-1-butanol, CF3CF2CF2CH2OH, perfluorooctane, perfluorohexane, 1,1,1-trifluorooctane, and 1,1,1,2,2-petantafluorodecane. Numbered embodiment 145 comprises any one of numbered embodiments 1-144, wherein at least one of the first dispersed phase and the second dispersed phase comprises a hydrophilic reagent. Numbered embodiment 146 comprises any one of numbered embodiments 1-145, wherein at least one of the first dispersed phase and the second dispersed phase comprises an aqueous reagent. Numbered embodiment 147 comprises any one of numbered embodiments 1-146, wherein at least one of the first dispersed phase and the second dispersed phase comprises water. Numbered embodiment 148 comprises any one of numbered embodiments 1-147, wherein a surface of the flow pathway comprises a polymer coating. Numbered embodiment 149 comprises any one of numbered embodiments 1-148, wherein a surface of the flow pathway comprises a fluorophilic coating. Numbered embodiment 150 comprises any one of numbered embodiments 1-149, wherein a surface of the flow pathway comprises a fluoropolymer coating. Numbered embodiment 151 comprises any one of numbered embodiments 1-150, wherein the fluoropolymer comprises a reagent selected from a group consisting of polyvinylfluoride (PVF), polyvinylidene fluoride (PVDF), polytetrafluoroethylene (PTFE), polychlorotrifluoroethylene (PCTFE), perfluoroalkoxy polymer, fluorinated ethylene-propylene (FEP), polyethylenetetrafluoroethylene (ETFE), polyethylenechlorotrifluoroethylene (ECTFE), perfluorinated elastomer, fluorocarbon, fluoroelastomer, perfluoropolyether (PFPE), perfluorosulfonic acid (PFSA), and perfluoropolyoxetane. Numbered embodiment 152 comprises any one of numbered embodiments 1-151, comprising a surfactant. Numbered embodiment 153 comprises any one of numbered embodiments 1-152, wherein the surfactant comprises a reagent selected from a group consisting of fluorocarbon, a hydrocarbon, and a silicone. Numbered embodiment 154 comprises any one of numbered embodiments 1-153, wherein a volume of at least one of the first dispersed phase and the second dispersed phase is in a range of about 1 picoliter to about 1 milliliter. Numbered embodiment 155 comprises any one of numbered embodiments 1-154, wherein the flow pathway comprises an internal hydraulic diameter in a range of about 0.001" to about 0.5". Numbered embodiment 156 comprises any one of numbered embodiments 1-155, wherein the system comprises a plurality of copies of a segment of nucleic acid. Numbered embodiment 157 comprises any one of numbered embodiments 1-156, wherein the first dispersed phase comprises at least one substrate, and wherein the second dispersed phase comprises at least one reagent. Numbered embodiment 158 comprises any one of numbered embodiments 1-157, wherein the first dispersed phase comprises a biological sample or a first drug precursor. Numbered embodiment 159 comprises any one of numbered embodiments 1-158, wherein the second dispersed phase comprises a lysis reagent or a second drug precursor. Numbered embodiment 160 comprises any one of numbered embodiments 1-159, wherein the first dispersed phase comprises at least one nucleic acid molecule, and wherein the second dispersed phase comprises a nucleic acid amplification reagent. Numbered embodiment 161 comprises any one of numbered embodiments 1-160, wherein the nucleic acid amplification reagent comprises a reagent selected from a group consisting of a primer, a probe, mastermix, a dNTP, a buffer, and an enzyme. Numbered embodiment 162 comprises any one of numbered embodiments 1-161, wherein the detector is configured to measure a fluorescent signal. Numbered embodiment 163 comprises any one of numbered embodiments 1-162, wherein the coalescer comprises an external source of energy. Numbered embodiment 164 comprises any one of numbered embodiments 1-163, wherein the external source of energy comprises an electric field between at least two electrodes. Numbered embodiment 165 comprises any one of numbered embodiments 1-164, wherein an electric potential between the at least two electrodes is in a range of about 100 V to about 25000 V. Numbered embodiment 166 comprises any one of numbered embodiments 1-165, wherein the external source comprises at least one of a pressure source and a mechanical source. Numbered embodiment 167 comprises any one of numbered embodiments 1-166, wherein the pressure source is a pump. Numbered embodiment 168 comprises any one of numbered embodiments 1-167, wherein the reactor is configured to induce a chemical reaction. Numbered embodiment 169 comprises any one of numbered embodiments 1-168, wherein the reactor is in communication with an external source of energy. Numbered embodiment 170 comprises any one of numbered embodiments 1-169, wherein the reactor comprises at least one heat source. Numbered embodiment 171 comprises any one of numbered embodiments 1-170, wherein the reactor comprises a plurality of heat sources. Numbered embodiment 172 comprises any one of numbered embodiments 1-171, wherein the reactor comprises a first heat source and a second heat source. Numbered embodiment 173 comprises any one of numbered embodiments 1-172, wherein the first heat source is maintained at a temperature in a range of 85° C. to 95° C. Numbered embodiment 174 comprises any one of numbered embodiments 1-173, wherein the first heat source is maintained at a temperature of about 90° C. Numbered embodiment 175 comprises any one of numbered embodiments 1-174, wherein the second heat source is maintained at a temperature in a range of 55° C. to 70° C. Numbered embodiment 176 comprises any one of numbered embodiments 1-175, wherein the flow pathway is in thermal communication with at least one of the first heat source and the second heat source. Numbered embodiment 177 comprises any one of numbered embodiments 1-176, wherein a reagent of the flow pathway passes through iteratively in communication with the first heat source and the second heat source. Numbered embodiment 178 comprises any one of numbered embodiments 1-177, wherein the reagent is subject to a plurality of iterations. Numbered embodiment 179 comprises any one of numbered embodiments 1-178, wherein the plurality of iterations is at least 30 iterations. Numbered embodiment 180 comprises any one of numbered embodiments 1-179, wherein the plurality of iterations is at least 60 iterations. Numbered embodiment 181 comprises any one of numbered embodiments 1-180, wherein the flow pathway passes through the first heat source and the second heat source in a figure eight. Numbered embodiment 182 comprises any one of numbered embodiments 1-181, wherein the reactor is a thermocycler. Numbered embodiment 183 comprises any one of numbered embodiments 1-182, wherein the controller is configured to specify at least one of a duration and a timing of mixing a first dispersed phase and a second dispersed phase. Numbered embodiment 184 comprises any one of numbered embodiments 1-183, wherein the system is automatically operated.

What is claimed is:

1. A method for conducting an assay on a biological sample, comprising:
    (a) providing a first injector comprising a first dispersed phase and a first continuous phase, and a second injector comprising a second dispersed phase and a second continuous phase, wherein said first dispersed phase comprises said biological sample and said second dispersed phase comprises one or more reagents for a reaction;
    (b) directing (i) the first dispersed phase from said first injector to a coalescer, and (ii) the second dispersed phase from said second injector to said coalescer, wherein said coalescer coalesces said first dispersed phase and said second dispersed phase to yield a fluid comprising said biological sample;
    (c) directing said fluid from said coalescer to a reactor downstream of said coalescer;
    (d) in said reactor, subjecting said fluid to conditions sufficient to conduct said reaction on the biological sample; and
    (e) using a detector that is in fluid communication with the reactor to detect said biological sample or a derivative thereof.

2. The method of claim 1, wherein said first injector, said second injector, or both said first injector and said second injector, have a zero dead volume.

3. The method of claim 1, wherein (b) further comprises using an external source of energy to apply energy to said first dispersed phase, said second dispersed phase, or both said first dispersed phase and said second dispersed phase.

4. The method of claim 3, wherein said external source of energy provides an electric field between a first electrode and a second electrode positioned on opposing sides of a junction outlet of said coalescer.

5. The method of claim 3, wherein said energy causes said first dispersed phase and said second dispersed phase to coalesce.

6. The method of claim 1, further comprising providing a controller.

7. The method of claim 6, wherein the controller controls a duration of coalescing, a timing of coalescing, or both, of the first dispersed phase and the second dispersed phase.

8. The method of claim 1, wherein said detector is an optical detector, and wherein (e) comprises detecting an optical signal from said biological sample or derivative thereof.

9. The method of claim 1, wherein said biological sample comprises a nucleic acid sample.

10. The method of claim 9, wherein the biological sample comprises DNA, RNA, or both DNA and RNA.

11. The method of claim 1, wherein the first dispersed phase comprises at least one nucleic acid molecule.

12. The method of claim 9, wherein the second dispersed phase comprises nucleic acid amplification reagents.

13. The method of claim 12, wherein (d) comprises using said nucleic acid amplification reagents to conduct said reaction on said nucleic acid sample to yield an amplification product of said nucleic acid sample, and wherein (e) comprises using said detector to detect said amplification product.

14. The method of claim 1, wherein said reactor comprises a heat source or a thermocycler.

15. The method of claim 1, wherein (d) comprises conducting said reaction in droplets, and (e) comprises detecting said biological sample or derivative thereof in droplets.

16. The method of claim 1, wherein: (a) the first injector is in fluid communication with (i) a reservoir for the first dispersed phase and (ii) a reservoir for the first continuous phase; (b) the second injector is in fluid communication with (i) a reservoir for the second dispersed phase and (ii) a reservoir for the second continuous phase; or both (a) and (b).

17. The method of claim 1, wherein the first continuous phase, the second continuous phase, or both the first continuous phase and the second continuous phase, comprise an oil.

18. The method of claim 1, wherein said reaction is a nucleic acid amplification reaction.

19. The method of claim 18, wherein said nucleic acid amplification reaction is a PCR, digital PCR, or RT-PCR reaction.

20. The method of claim 17, wherein the oil comprises a fluorinated oil, a silicone oil, a hydrocarbon oil, a mineral oil, or any combination thereof.

* * * * *